US007811583B2

(12) United States Patent
Kirke et al.

(10) Patent No.: US 7,811,583 B2
(45) Date of Patent: Oct. 12, 2010

(54) **ANTIGENS AND VACCINES AGAINST *PISCIRICKETTSIA SALMONIS***

(75) Inventors: David Francis Kirke, Slough (GB); Michael James Francis, Amersham (GB)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 12/338,192

(22) Filed: Dec. 18, 2008

(65) Prior Publication Data

US 2009/0162391 A1 Jun. 25, 2009

Related U.S. Application Data

(60) Provisional application No. 61/014,782, filed on Dec. 19, 2007.

(51) Int. Cl.
*A61K 39/02* (2006.01)

(52) U.S. Cl. .............. 424/234.1; 424/185.1; 424/190.1; 424/192.1; 424/201.1; 424/203.1

(58) Field of Classification Search ....................... None
See application file for complete search history.

(56) References Cited

U.S. PATENT DOCUMENTS

| | | | |
|---|---|---|---|
| 5,165,925 | A | 11/1992 | Leong |
| 6,887,989 | B2 | 5/2005 | Simard et al. |
| 6,936,256 | B2 | 8/2005 | Vakharia |
| 7,302,913 | B2 | 12/2007 | Salonius et al. |
| 2003/0147909 | A1 | 8/2003 | Gonzalez |
| 2003/0166526 | A1 | 9/2003 | Challita-Eid et al. |
| 2004/0086524 | A1 | 5/2004 | Kuzyk et al. |
| 2005/0002946 | A1 | 1/2005 | Kuzyk et al. |
| 2007/0207165 | A1 | 9/2007 | Thiry et al. |

FOREIGN PATENT DOCUMENTS

| | | |
|---|---|---|
| CL | 2086-2001 | 8/2001 |
| CL | 3110-2001 | 12/2001 |
| CL | 3111-2001 | 12/2001 |
| CL | 3112-2001 | 12/2001 |
| CL | 3113-2001 | 12/2001 |
| CL | 1047-2003 | 5/2003 |
| CL | 1048-2003 | 5/2003 |
| CL | 1049-2003 | 5/2003 |
| EP | 0712926 | 5/1996 |
| GB | 2 356 632 | 5/2001 |
| WO | WO 01/49712 | 7/2001 |
| WO | WO 01/68865 | 9/2001 |
| WO | WO 02/38770 | 5/2002 |
| WO | WO 2005/035558 | 4/2005 |
| WO | WO 2006/037383 | 4/2006 |

OTHER PUBLICATIONS

Mikayama et al. (Nov. 1993. Proc.Natl.Acad.Sci. USA, vol. 90 : 10056-10060).*

Rudinger et al. (Jun. 1976. Peptide Hormones. Biol.Council. pp. 5-7).*

Chothia et al (The EMBO Journal, 1986, 5/4:823-26).*

Greenspan et al (Nature Biotechnology 7: 936-937, 1999).*

Bravo, S., et al., "Coho Salmon Syndrome in Chile," FHS/AFS Newsletter, vol. 17, No. 2, p. 3 (1989).

Havarstein, L.S., et al., "Sequence of the large double-stranded RNA segment of the N1 strain of infectious pancreatic necrosis virus: a comparison with other *Birnaviridae*", Journal of General Virology, vol. 71, pp. 299-308 (1990).

Mauel, M., et al., "Piscirickettsiosis and piscirickettsiosis-like infections in fish: a review", Veterinary Microbiology, vol. 87, pp. 279-289 (2002).

Smith, P.A., et al., "Routes of entry of *Piscirickettsia salmonis* in rainbow trout Oncorhynchus *mykiss*", Diseases of Aquatic Organisms, vol. 37, pp. 165-172 (1999).

Pryde, W.T., "Nucleotide sequence analysis of the serotype-specific epitope of infectious pancreatic necrosis virus", Arch Virol, vol. 129, pp. 287-293 (1993).

Leong, J.C., et. al., "Fish Vaccine Antigens Produced or Delivered by Recombinant DNA Technologies", Dev. Biol. Stand. Basel, Karger, vol. 90 pp. 267-277 (1997).

Kuzyk, M.A., et al., "Antigenic Characterization of the Salmonid Pathogen *Piscirickettsia salmonis*", Infection and Immunity, vol. 64, No. 12, pp. 5205-5210 (1996).

Russmann, H., et al., "Attenuated Yersinia pseudotuberculosis Carrier Vaccine for Simultaneous Antigen-Specific CD4 and CD8 T-Cell Induction", Infection and Immunity, vol. 71, No. 6, pp. 3463-3472 (2003).

Henriquez, V., et al., "An Alternative Efficient Procedure for Purification of the Obligate Intracellular Fish Bacterial Pathogen *Piscirickettsia salmonis*", Applied and Environmental Microbiology, vol. 69, No. 10, pp. 6268-6271 (2003).

Valenzuela, P., et al., "Sequence and Applications of the *Piscirickttsia salmonis* Genome", Biological Research, vol. 34, No. 3-4 (2001).

Henriquez, V.B., et al., "Improved Purification of The Obligate Intracelluar", 102$^{nd}$ General Meeting of the American Society for Microbiology, (Abstract).

Miquel, A., et al., "Immunoresponse of Coho salmon immunized with a gene expression library from *Piscirickettsia salmonis*", Biol. Res., vol. 36, pp. 313-323 (2003).

Wilhelm, V., "The complete sequence of the mitochondrial genome of the Chinook salmon, Oncorhynchus tshawytsche", Biol. Res., vol. 36, pp. 223-231 (2003).

Hyung, J., et al., "A gene cluster encoding malonyl-CoA decarboxylase (MatA), malonyl-CoA synthetase (MatB) and a putative dicarboxylate carrier protein (MatC) in Rhizobium trifolii", Eur. J. Biochem., vol. 257, pp. 395-402 (1998).

(Continued)

*Primary Examiner*—Jennifer E Graser

(57) ABSTRACT

The present invention discloses novel proteins, e.g., antigens, from *Piscirickettsia salmonis*. The present invention further discloses nucleic acids that encode these proteins. The present invention also discloses the use of the proteins, e.g., antigens, and nucleic acids to prepare vaccines against salmonid rickettsial septicemia (SRS). The present invention also discloses vaccines that can be used to protect fish from *Piscirickettsia salmonis*, as well as other pathogens. In addition, the present invention discloses methods of using the vaccines of the present invention to protect fish from SRS as well as from other pathogenic diseases.

8 Claims, 1 Drawing Sheet

OTHER PUBLICATIONS

Barnes, M.N., et al., "Purification of *Piscirickettsia salmonis* and partial characteriation of antigens", Diseases of Aquatic Organisms, vol. 33, pp. 33-41 (1998).
Herbert, W.J., et al., Definition of Vaccine: The Dictionary of Immunology, Academic Press (1995).
Harlow, E., et al., "Antibodies A Laboratory Manual", Cold Spring Harbor Laboratory Press Inc., pp. 23-27, 25-33 and 72-74 (1988).
Greenspan, N.S., et al., "Defining epitopes: It's not as easy as it seems", Nature Biotechnology, vol. 17 pp. 936-937 (1999).
Colman, P.M., "Effects of amino acid sequence changes on antibody-antigen interactions", Research in Immunology, vol. 145, pp. 33-36 (1994).
Houghten, R.A., et al., "New Approaches to Immunization Developing Vaccines Against Parasitic, Bacterial, and Viral Diseases", Vaccines86, Cold Spring Harbor Laboratory, pp. 21-25 (1986).
Molling, K., et al., "Naked DNA for vaccines or therapy", J. Mol. Med., vol. 75, pp. 242-246 (1997).
Tighe, H., et al., "Gene vaccination: plasmid DNA is more than just a blueprint", Immunology Today, vol. 19, No. 2 pp. 89-97 (1998).
Dittmer, U., et al., "Treatment of infectious diseases with immunostimulatory oligodeoxynucleotides containing CpG motifs", Current Opinion in Microbiology, vol. 6, pp. 472-477 (2003).
Jorgensen, J.B., et al., "CpG oligodeoxynucleotides and plasmid DNA stimulate Atlantic salmon (*Salmo salar* L.) leucocytes to produce supernatants with antiviral activity", Development & Comparative Immunology, vol. 25, pp. 313-321 (2001).
Jones, S., et al., "Virulence and antigenic characteristics of a cultured Rickettsiales-like organisum isolated from farmed Atlantic salmon *Salmo salar* in eastern Canada", Diseases of Aquatic Organisms, vol. 33, pp. 25-31 (1998).
New England Biolabs Catalog, p. 111 (1996/1997).
Morzunov, S., et al., "The complete genome structure and phylogenetic relationship of infectious hematopoietic necrosis virus", Virus Research, vol. 38, pp. 175-192 (1995).
Argenton, F., et al., "Use of random DNA amplification to generate specific molecular probes for hybridization tests and PCR-based diagnosis of *Yersinia ruckeri*", Diseases of Aquatic Organisms, vol. 24, pp. 121-127 (1996).
Gudding, R., et al., "Recent developments in fish vaccinology", Veterinary Immunology and Immunopathology, vol. 72, pp. 203-212 (1999).
Gerhold, D., et al., "It's the genes! EST access to human genome content", BioEssays, vol. 18, No. 12, pp. 973-981 (1996).
Wells, T., et al., "The chemokine information source: identification and characterization of novel chomokines using the WorldWideWeb and Expressed Sequence Tag Databases", vol. 61, pp. 545-550 (1997).
Bork, P., "Powers and Pitfalls in Sequence Analysis: The 70% Hurdle", Genome Research, vol. 10, pp. 398-400 (2000).
Ellis, R.W., "New Technologies for Making Vaccines", Vaccines, Chapter 29, pp. 568-575 (1988).
Rollenhagen, C., et al., "Antigen selection based on expression levels during infection facilitates vaccine development for an intracellular pathogen", PNAS, vol. 101, No. 23, pp. 8739-8744 (2004).
Thacker, E.L., "Detection of intracellular porcine reproductive and respiratory syndrome virus nucleocapsid protein in porcine macrophages by flow cytometry", J. Vet. Diagn. Invest., vol. 10, pp. 308-311 (1998).
Stowers, et al., "Vaccination of Monkeys with Recombinant *Plasmodium falciparum* Apical Membrane Antigen 1 Confers Protection against Blood-Stage Malaria", Infection and Immunity, vol. 70, No. 12, pp. 6961-6967 (2002).
Didier, E.S., et al., "Epidemiology of microsporidiosis: sources and modes of transmission", Veterinary Parasitology, vol. 126, pp. 145-166 (2004).
Lederer, J., et al., "*Haemophilus somnus*," a Facultative Intracellular Pathogen of Bovine Mononuclear Phagocytes, Infection and Immunity, vol. 55, No. 2, pp. 381-387 (1987).
Schade, B., et al., "Toxoplasma gondii induction of interleukin-12 is associated with acute virulence in mice and depends on the host genotype", Veterinary Parasitology, vol. 100, pp. 63-74 (2001).
Cross, M.L., et al., "Intracellular survival of virulent Mycobacterium bovis and M. bovis BCG in ferret Macrophages", Veterinary Microbiology, vol. 66, pp. 235-243 (1999).
Wilhelm, V., "Cloning and expression of the coding regions of the heat shock proteins HSP10 and HSP16 from *Piscirickettsia salmonis*", Biol. Res. vol. 36, pp. 421-428 (2003).
PCT International Search Report dated Sep. 23, 2005 for corresponding PCT Application No. PCT/IB2004/003339.
Blastp Serach Results (May 26, 2009).
NCBI Blast Search—Acholeplasma Laidlawii PG-8A.

* cited by examiner

SEQUENCE LISTING

```
<160> NUMBER OF SEQ ID NOS: 16

<210> SEQ ID NO 1
<211> LENGTH: 2820
<212> TYPE: DNA
<213> ORGANISM: Piscirickettsia salmonis

<400> SEQUENCE: 1

atgaaaaaga taattacaat gatgttattg gtgttatcac ttgtgttggt cgcttgtacc     60

ccaagtgaag aaccaccaac tacagtgcca gatgttgaat ccatcgaatt taatatgact    120

tcaacgactg tagcaccagg tgaacataca ctagttgcaa aagcattacc tgaaggatct    180

aatcaacaaa ttagatttag tattcaaggt attgtatctg gtgtatccat tacgggtgat    240

aagttaaatg ttggtaatgc tgttgaagat ggtatgaaat ttacagtcgt agcaacatct    300

gtatatgatc caacaattcg tgcaacacta gagtttacag ttgtaaatgt tggtgttgaa    360

gttgttgaaa ttagaacaga agaagaacta cgtgcaattc atacaaatga aggtggttta    420

tcattatctt atgtattaat gaatgatatt gaactaacag ctccatggac accaattggt    480
```

-continued

```
attgctgaag ttgaaactga ttctgggcaa atcattccag gtacgccatt taatggtatc    540
tttaatggaa atggttttac aattagtggc atattagttg aaagtgaaga accattattt    600
aatgcaggat tctttgctca aattggtgca actgcaattg ttaagaatac aacatttgaa    660
ggtatagtaa atgcaaccgg atggtccggt ggtatcgcag gtattaacga aggtttaata    720
gaaaatgttg tatctaatgt aagagttact gtaacaggta catccgcagg ttcgctagta    780
tctgttaata gaggtttaat ccaatatgct tacggtattg gtaaagttgt tagtgaaaca    840
aaccctaata catcaggtcg ttctgctggt ttagtggttg ctaatgatgg atcaatgatt    900
gaagtgtatg gtgactatca agcacttgga acacctaact atacagcatt tagtccatca    960
acaaacccaa tgtatatgtt acctacagta gatatgaaaa catcttcaac ttgggcttca   1020
tttgatgcag atgtttggta tattgaaaat ggtacatatc cattattaaa acatgaagga   1080
ttcgttccac cagtgatcgt tcctgaatta ggtattacaa ttaaaaatac tgagttaaat   1140
catgatgttg aagtatcaag tgaactacaa ataaatgcag aagtcattaa cccagaaggt   1200
agtgaagtta ttgtttatgc acttaaagaa gcagtagcag gtgtagcaat tagtgaaaca   1260
ggtttagtta catttgatat cactacaatt gctgctaact tctcatttac agtagtagtg   1320
acaattgatg gtactgaagt tagtgctgaa aaaacattta caggcgtata taaccctgaa   1380
attgtagatg atacagtgta tattgaaaca gaaacacaat tattaaactt acttgctgga   1440
caaacaaacc cagacaattt aagtaaaaca tttgtattat taaatgatat tgtcttaact   1500
tctaattgga cagcaattgg tattgcacca aatgaagacg aaggtattgt aggtgttcca   1560
tttacaggtg tatttgatgg tcaaggctat aagatctcag gtattagtat gccaggtggt   1620
ggatggaata aaggtttctt tggatatatt ggaacaactg gtgttgttaa aaacacacac   1680
tttgaaggta atctagaagc aaacgcatgg tcaggtgcac ttgcagcaaa taactcaggt   1740
actattcaag atgtagttgt tgatattgaa gtatatgtct ggggtaataa tggtggcgca   1800
atcgttgaac ataaccatgg tctacttaaa aatattgtcg tattaggtaa agctgtatca   1860
gatagtggtc ctacagcagt tggactggtt gttactaact ttggtacttt agaaaatgta   1920
tttgctaacg cagatacagt aggtacagca aacttagtat ctaatggtgc tctcgctgat   1980
gatggtaaac acattattag tgcccaagac tttgttaaag ctacaactta tgcaaacttt   2040
gatagcgcaa tctggttaat cgtagatggc caagtacctg tattaattaa tgaagataca   2100
gtattacctg aaacagtagt ttatattgaa acagaagcag aattattaag cctacttgct   2160
ggtcaagtag atccagaagc attatcaaaa acatacaaac ttaaaaatga tatcgttcta   2220
acttctaatt ggacagcaat tggtattgca ccaaatgaag acgaaggtat tgtaggtgtt   2280
ccatttacag gtgtatttga tggtcaaggc tataagatct caggtattag tatgccaggt   2340
ggcggatgga ataaaggttt ctttggttac attggaacaa cgggtgttgt taaaaataca   2400
cactttgaag gtaatattga agcaaacgca tggtcaggtg cacttgcagc aaataactcg   2460
ggtactatta tggatgttgt agtagacatt gaagtatatg tctggggtaa taatggtggt   2520
gcaattgttg aacataacca cggtttactt aaaaatatta tcgtcttagg taaagctgta   2580
tcagatggtg gtcctacagt agttggacta gttgttacta actttggtac actagaagat   2640
gtatatgcaa atgttgacac agtaggtact ttaaacttag tatcatttgg tagcgtagca   2700
gatgatggta cacacattat tagtgcttca aactttgtta aagcagaaac ttatgcaaac   2760
ttctcaagtg atgtttggac aattattgat ggtagcaccc ctgtattaaa acaagcataa   2820
```

-continued

<210> SEQ ID NO 2
<211> LENGTH: 939
<212> TYPE: PRT
<213> ORGANISM: Piscirickettsia salmonis

<400> SEQUENCE: 2

```
Met Lys Lys Ile Ile Thr Met Met Leu Leu Val Leu Ser Leu Val Leu
1               5                   10                  15

Val Ala Cys Thr Pro Ser Glu Glu Pro Pro Thr Thr Val Pro Asp Val
            20                  25                  30

Glu Ser Ile Glu Phe Asn Met Thr Ser Thr Thr Val Ala Pro Gly Glu
        35                  40                  45

His Thr Leu Val Ala Lys Ala Leu Pro Glu Gly Ser Asn Gln Gln Ile
    50                  55                  60

Arg Phe Ser Ile Gln Gly Ile Val Ser Gly Val Ser Ile Thr Gly Asp
65                  70                  75                  80

Lys Leu Asn Val Gly Asn Ala Val Glu Asp Gly Met Lys Phe Thr Val
                85                  90                  95

Val Ala Thr Ser Val Tyr Asp Pro Thr Ile Arg Ala Thr Leu Glu Phe
            100                 105                 110

Thr Val Val Asn Val Gly Val Glu Val Val Glu Ile Arg Thr Glu Glu
        115                 120                 125

Glu Leu Arg Ala Ile His Thr Asn Glu Gly Gly Leu Ser Leu Ser Tyr
    130                 135                 140

Val Leu Met Asn Asp Ile Glu Leu Thr Ala Pro Trp Thr Pro Ile Gly
145                 150                 155                 160

Ile Ala Glu Val Glu Thr Asp Ser Gly Gln Ile Ile Pro Gly Thr Pro
                165                 170                 175

Phe Asn Gly Ile Phe Asn Gly Asn Gly Phe Thr Ile Ser Gly Ile Leu
            180                 185                 190

Val Glu Ser Glu Glu Pro Leu Phe Asn Ala Gly Phe Phe Ala Gln Ile
        195                 200                 205

Gly Ala Thr Ala Ile Val Lys Asn Thr Thr Phe Glu Gly Ile Val Asn
    210                 215                 220

Ala Thr Gly Trp Ser Gly Gly Ile Ala Gly Ile Asn Glu Gly Leu Ile
225                 230                 235                 240

Glu Asn Val Val Ser Asn Val Arg Val Thr Val Thr Gly Thr Ser Ala
                245                 250                 255

Gly Ser Leu Val Ser Val Asn Arg Gly Leu Ile Gln Tyr Ala Tyr Gly
            260                 265                 270

Ile Gly Lys Val Val Ser Glu Thr Asn Pro Asn Thr Ser Gly Arg Ser
        275                 280                 285

Ala Gly Leu Val Val Ala Asn Asp Gly Ser Met Ile Glu Val Tyr Gly
    290                 295                 300

Asp Tyr Gln Ala Leu Gly Thr Pro Asn Tyr Thr Ala Phe Ser Pro Ser
305                 310                 315                 320

Thr Asn Pro Met Tyr Met Leu Pro Thr Val Asp Met Lys Thr Ser Ser
                325                 330                 335

Thr Trp Ala Ser Phe Asp Ala Asp Val Trp Tyr Ile Glu Asn Gly Thr
            340                 345                 350

Tyr Pro Leu Leu Lys His Glu Gly Phe Val Pro Pro Val Ile Val Pro
        355                 360                 365

Glu Leu Gly Ile Thr Ile Lys Asn Thr Glu Leu Asn His Asp Val Glu
    370                 375                 380
```

-continued

```
Val Ser Ser Glu Leu Gln Ile Asn Ala Glu Val Ile Asn Pro Glu Gly
385                 390                 395                 400

Ser Glu Val Ile Val Tyr Ala Leu Lys Glu Ala Val Ala Gly Val Ala
                405                 410                 415

Ile Ser Glu Thr Gly Leu Val Thr Phe Asp Ile Thr Thr Ile Ala Ala
            420                 425                 430

Asn Phe Ser Phe Thr Val Val Val Thr Ile Asp Gly Thr Glu Val Ser
        435                 440                 445

Ala Glu Lys Thr Phe Thr Gly Val Tyr Asn Pro Glu Ile Val Asp Asp
    450                 455                 460

Thr Val Tyr Ile Glu Thr Glu Thr Gln Leu Leu Asn Leu Leu Ala Gly
465                 470                 475                 480

Gln Thr Asn Pro Asp Asn Leu Ser Lys Thr Phe Val Leu Leu Asn Asp
                485                 490                 495

Ile Val Leu Thr Ser Asn Trp Thr Ala Ile Gly Ile Ala Pro Asn Glu
            500                 505                 510

Asp Glu Gly Ile Val Gly Val Pro Phe Thr Gly Val Phe Asp Gly Gln
        515                 520                 525

Gly Tyr Lys Ile Ser Gly Ile Ser Met Pro Gly Gly Gly Trp Asn Lys
    530                 535                 540

Gly Phe Phe Gly Tyr Ile Gly Thr Thr Gly Val Val Lys Asn Thr His
545                 550                 555                 560

Phe Glu Gly Asn Leu Glu Ala Asn Ala Trp Ser Gly Ala Leu Ala Ala
                565                 570                 575

Asn Asn Ser Gly Thr Ile Gln Asp Val Val Val Asp Ile Glu Val Tyr
            580                 585                 590

Val Trp Gly Asn Asn Gly Gly Ala Ile Val Glu His Asn His Gly Leu
        595                 600                 605

Leu Lys Asn Ile Val Val Leu Gly Lys Ala Val Ser Asp Ser Gly Pro
    610                 615                 620

Thr Ala Val Gly Leu Val Val Thr Asn Phe Gly Thr Leu Glu Asn Val
625                 630                 635                 640

Phe Ala Asn Ala Asp Thr Val Gly Thr Ala Asn Leu Val Ser Asn Gly
                645                 650                 655

Ala Leu Ala Asp Asp Gly Lys His Ile Ile Ser Ala Gln Asp Phe Val
            660                 665                 670

Lys Ala Thr Thr Tyr Ala Asn Phe Asp Ser Ala Ile Trp Leu Ile Val
        675                 680                 685

Asp Gly Gln Val Pro Val Leu Ile Asn Glu Asp Thr Val Leu Pro Glu
    690                 695                 700

Thr Val Val Tyr Ile Glu Thr Glu Ala Glu Leu Leu Ser Leu Leu Ala
705                 710                 715                 720

Gly Gln Val Asp Pro Glu Ala Leu Ser Lys Thr Tyr Lys Leu Lys Asn
                725                 730                 735

Asp Ile Val Leu Thr Ser Asn Trp Thr Ala Ile Gly Ile Ala Pro Asn
            740                 745                 750

Glu Asp Glu Gly Ile Val Gly Val Pro Phe Thr Gly Val Phe Asp Gly
        755                 760                 765

Gln Gly Tyr Lys Ile Ser Gly Ile Ser Met Pro Gly Gly Gly Trp Asn
    770                 775                 780

Lys Gly Phe Phe Gly Tyr Ile Gly Thr Thr Gly Val Val Lys Asn Thr
785                 790                 795                 800

His Phe Glu Gly Asn Ile Glu Ala Asn Ala Trp Ser Gly Ala Leu Ala
```

-continued

```
                805                 810                 815

Ala Asn Asn Ser Gly Thr Ile Met Asp Val Val Val Asp Ile Glu Val
            820                 825                 830

Tyr Val Trp Gly Asn Asn Gly Gly Ala Ile Val Glu His Asn His Gly
        835                 840                 845

Leu Leu Lys Asn Ile Ile Val Leu Gly Lys Ala Val Ser Asp Gly Gly
    850                 855                 860

Pro Thr Val Val Gly Leu Val Val Thr Asn Phe Gly Thr Leu Glu Asp
865                 870                 875                 880

Val Tyr Ala Asn Val Asp Thr Val Gly Thr Leu Asn Leu Val Ser Phe
                885                 890                 895

Gly Ser Val Ala Asp Asp Gly Thr His Ile Ile Ser Ala Ser Asn Phe
            900                 905                 910

Val Lys Ala Glu Thr Tyr Ala Asn Phe Ser Ser Asp Val Trp Thr Ile
        915                 920                 925

Ile Asp Gly Ser Thr Pro Val Leu Lys Gln Ala
    930                 935
```

<210> SEQ ID NO 3
<211> LENGTH: 2499
<212> TYPE: DNA
<213> ORGANISM: Piscirickettsia salmonis

<400> SEQUENCE: 3

```
atgcatttgg tgttgttgct aaaaagtaaa aaggacaaat atatgaaaaa aataagctta     60

ataatgattt ttctgctttc tatcctattg gtaagttgtg tagaaaaaga agaaccaaaa    120

tttgatccag ataaatatct agatttagag aatattgtat ttgatgattt tgataacgga    180

attgacccga atatgtgggt tattggtaat agtaagtggg gtgtaggtaa tggtggtgtc    240

atctatgaaa atgtccatta cacaaatgac ggtattgtag ttcttcaaac caatggtgac    300

ttgtatgatg gtccacttcg cggtattggt aatacccatg gcagacgtac aggtgcaatg    360

attacaacaa gagaagcact aggtcctggt agatttgaag tacgtatgcg tattatgcca    420

cgttttggtt caactactgc tatgtggact tactattatg ataatggtat gaaccatgaa    480

atagatatcg aaagtaacgt tgaaaatgac tttagaaaag tatggactac aaactggatt    540

agtttaacag aatatagtac tgtgtctaat accttagatt ttgcacaaaa tgattttgaa    600

tggcgtacat accgttttga ctggtttaca gatccaaaac gcattgatta ttatattgat    660

gaagtattag tttcatcaca atcttcttat gtaccagatc atgcaggaga atttaatatt    720

ggtaattggt ttccagatgc ttgggcaggt gtacctgatt ttgaaacaga ctatacctat    780

gtagactggt tcaaatatac accatttaaa gaacaaccat atacaccaac accggcaaat    840

aatcaaagtc ctgcaaactt ctatccatca gaaccaattg aacatccaat agcaaacctc    900

atttcaaatg caggttttga aacagatgct ccagcttggc gttatcctgt aactagtggt    960

gtggaactac tagaaggtga aggtttaaac ggatcaagag gaatctttgt tccacaaaat   1020

gatattgcat atcaatttgt cacaggatta gatgaaacct ttgaaatgac atttagtgca   1080

catgcaaaac tacctttaaa tggtagtgga tatgttttat tagagttcta cccagcagag   1140

acacaaaaaa ttgatcagta tatgattgag tttaactcaa gcgatgaaga ttttatagca   1200

gatacattct atggtaaaga atttaccttt aatgtacctc taggaactaa acgtgttgaa   1260

gtgtctttaa ttggaggaga ttctggtata tacttcgatg atttattctt taacctaact   1320

aaaaaaccca ggcccgaaat tgtagaagaa ggtgatgatg tgcaacgttt aaacatagat   1380
```

-continued

```
tttaaaaatg gtattgactc caatgtttgg gcagttgcaa atcaacgttg gggaggtaca   1440

catcatggtg gtgtaatctt ccaaaacgta cactacacag aagaaggtaa tttactcatt   1500

caagccaatg gtgattacta tgaaggtcca ttaaaaggtg ttgaacaaaa taatggaaaa   1560

cgcactgggg gagctatcta tactaaagaa gcatttggcc caggatcttt tgaagtaaaa   1620

gctaaaatca tgccacgttt tggggcaaca acagcatttt ggacatttaa ctacttagat   1680

ggtattaata gtgaaattga ttttgagttt aacgtaggca atgattttag tacagtttgg   1740

ttaaccaact ggttaaccga aacaaactat aacaactaca cccatcaaat ggatagtttc   1800

cataatgatg gaaactggca tatataccgt tttgaatggc atacactacc gacgcctcat   1860

attaaatact ttatcgatgg caaacttgca tatacagaac atactaaagt tccaacgatg   1920

tctgcaagat actggattgg tgtatggttt ccaaataact gggcaggaga tccaaacttt   1980

gaaacagatt atttagaagt tgaatatttc aaatatgagt cattcccgga tcatccgtat   2040

gttgttggtc caactggggc atcctctcca acagcatttt acccaacagc gccaataaaa   2100

aaaccagttt ctaacctttt accacacggt aatctagatt atgaaacagg ttatatgtta   2160

acaggggatg cagtgatttc aaatggtgaa ttgaaaactg gtttactagg cagtgctgag   2220

tctcttatta cagggttaaa tgatgccttt gaacttacat taaagcttaa agcaaaagcc   2280

tcaaataacg caaccgtgcg cattgagtat ttagataagg atttaaatgt gataagtggt   2340

gaagatatta ttgtatcaaa cttaaacgcg aatacattta caaactttac atccgtaatt   2400

aatctagtgg aaggcactag agccatcaat gtgatttttg agggaacaaa tatcacatat   2460

gatgacttat ttataaattt aacacacaag gtgaattga                          2499


<210> SEQ ID NO 4
<211> LENGTH: 832
<212> TYPE: PRT
<213> ORGANISM: Piscirickettsia salmonis

<400> SEQUENCE: 4

Met His Leu Val Leu Leu Leu Lys Ser Lys Lys Asp Lys Tyr Met Lys
1               5                   10                  15

Lys Ile Ser Leu Ile Met Ile Phe Leu Leu Ser Ile Leu Leu Val Ser
            20                  25                  30

Cys Val Glu Lys Glu Glu Pro Lys Phe Asp Pro Asp Lys Tyr Leu Asp
        35                  40                  45

Leu Glu Asn Ile Val Phe Asp Asp Phe Asp Asn Gly Ile Asp Pro Asn
    50                  55                  60

Met Trp Val Ile Gly Asn Ser Lys Trp Gly Val Gly Asn Gly Gly Val
65                  70                  75                  80

Ile Tyr Glu Asn Val His Tyr Thr Asn Asp Gly Ile Val Val Leu Gln
                85                  90                  95

Thr Asn Gly Asp Leu Tyr Asp Gly Pro Leu Arg Gly Ile Gly Asn Thr
            100                 105                 110

His Gly Arg Arg Thr Gly Ala Met Ile Thr Thr Arg Glu Ala Leu Gly
        115                 120                 125

Pro Gly Arg Phe Glu Val Arg Met Arg Ile Met Pro Arg Phe Gly Ser
    130                 135                 140

Thr Thr Ala Met Trp Thr Tyr Tyr Tyr Asp Asn Gly Met Asn His Glu
145                 150                 155                 160

Ile Asp Ile Glu Ser Asn Val Glu Asn Asp Phe Arg Lys Val Trp Thr
                165                 170                 175
```

-continued

```
Thr Asn Trp Ile Ser Leu Thr Glu Tyr Ser Thr Val Ser Asn Thr Leu
            180                 185                 190

Asp Phe Ala Gln Asn Asp Phe Glu Trp Arg Thr Tyr Arg Phe Asp Trp
        195                 200                 205

Phe Thr Asp Pro Lys Arg Ile Asp Tyr Tyr Ile Asp Glu Val Leu Val
    210                 215                 220

Ser Ser Gln Ser Ser Tyr Val Pro Asp His Ala Gly Glu Phe Asn Ile
225                 230                 235                 240

Gly Asn Trp Phe Pro Asp Ala Trp Ala Gly Val Pro Asp Phe Glu Thr
                245                 250                 255

Asp Tyr Thr Tyr Val Asp Trp Phe Lys Tyr Thr Pro Phe Lys Glu Gln
            260                 265                 270

Pro Tyr Thr Pro Thr Pro Ala Asn Asn Gln Ser Pro Ala Asn Phe Tyr
        275                 280                 285

Pro Ser Glu Pro Ile Glu His Pro Ile Ala Asn Leu Ile Ser Asn Ala
    290                 295                 300

Gly Phe Glu Thr Asp Ala Pro Ala Trp Arg Tyr Pro Val Thr Ser Gly
305                 310                 315                 320

Val Glu Leu Leu Glu Gly Glu Gly Leu Asn Gly Ser Arg Gly Ile Phe
                325                 330                 335

Val Pro Gln Asn Asp Ile Ala Tyr Gln Phe Val Thr Gly Leu Asp Glu
            340                 345                 350

Thr Phe Glu Met Thr Phe Ser Ala His Ala Lys Leu Pro Leu Asn Gly
        355                 360                 365

Ser Gly Tyr Val Leu Leu Glu Phe Tyr Pro Ala Glu Thr Gln Lys Ile
    370                 375                 380

Asp Gln Tyr Met Ile Glu Phe Asn Ser Ser Asp Glu Asp Phe Ile Ala
385                 390                 395                 400

Asp Thr Phe Tyr Gly Lys Glu Phe Thr Phe Asn Val Pro Leu Gly Thr
                405                 410                 415

Lys Arg Val Glu Val Ser Leu Ile Gly Gly Asp Ser Gly Ile Tyr Phe
            420                 425                 430

Asp Asp Leu Phe Phe Asn Leu Thr Lys Lys Pro Arg Pro Glu Ile Val
        435                 440                 445

Glu Glu Gly Asp Asp Val Gln Arg Leu Asn Ile Asp Phe Lys Asn Gly
    450                 455                 460

Ile Asp Ser Asn Val Trp Ala Val Ala Asn Gln Arg Trp Gly Gly Thr
465                 470                 475                 480

His His Gly Gly Val Ile Phe Gln Asn Val His Tyr Thr Glu Glu Gly
                485                 490                 495

Asn Leu Leu Ile Gln Ala Asn Gly Asp Tyr Tyr Glu Gly Pro Leu Lys
            500                 505                 510

Gly Val Glu Gln Asn Asn Gly Lys Arg Thr Gly Gly Ala Ile Tyr Thr
        515                 520                 525

Lys Glu Ala Phe Gly Pro Gly Ser Phe Glu Val Lys Ala Lys Ile Met
    530                 535                 540

Pro Arg Phe Gly Ala Thr Thr Ala Phe Trp Thr Phe Asn Tyr Leu Asp
545                 550                 555                 560

Gly Ile Asn Ser Glu Ile Asp Phe Glu Phe Asn Val Gly Asn Asp Phe
                565                 570                 575

Ser Thr Val Trp Leu Thr Asn Trp Leu Thr Glu Thr Asn Tyr Asn Asn
            580                 585                 590
```

-continued

```
Tyr Thr His Gln Met Asp Ser Phe His Asn Asp Gly Asn Trp His Ile
        595                 600                 605

Tyr Arg Phe Glu Trp His Thr Leu Pro Thr Pro His Ile Lys Tyr Phe
    610                 615                 620

Ile Asp Gly Lys Leu Ala Tyr Thr Glu His Thr Lys Val Pro Thr Met
625                 630                 635                 640

Ser Ala Arg Tyr Trp Ile Gly Val Trp Phe Pro Asn Asn Trp Ala Gly
                645                 650                 655

Asp Pro Asn Phe Glu Thr Asp Tyr Leu Glu Val Glu Tyr Phe Lys Tyr
            660                 665                 670

Glu Ser Phe Pro Asp His Pro Tyr Val Val Gly Pro Thr Gly Ala Ser
        675                 680                 685

Ser Pro Thr Ala Phe Tyr Pro Thr Ala Pro Ile Lys Lys Pro Val Ser
    690                 695                 700

Asn Leu Leu Pro His Gly Asn Leu Asp Tyr Glu Thr Gly Tyr Met Leu
705                 710                 715                 720

Thr Gly Asp Ala Val Ile Ser Asn Gly Glu Leu Lys Thr Gly Leu Leu
                725                 730                 735

Gly Ser Ala Glu Ser Leu Ile Thr Gly Leu Asn Asp Ala Phe Glu Leu
            740                 745                 750

Thr Leu Lys Leu Lys Ala Lys Ala Ser Asn Asn Ala Thr Val Arg Ile
        755                 760                 765

Glu Tyr Leu Asp Lys Asp Leu Asn Val Ile Ser Gly Glu Asp Ile Ile
    770                 775                 780

Val Ser Asn Leu Asn Ala Asn Thr Phe Thr Asn Phe Thr Ser Val Ile
785                 790                 795                 800

Asn Leu Val Glu Gly Thr Arg Ala Ile Asn Val Ile Phe Glu Gly Thr
                805                 810                 815

Asn Ile Thr Tyr Asp Asp Leu Phe Ile Asn Leu Thr His Lys Val Asn
            820                 825                 830


<210> SEQ ID NO 5
<211> LENGTH: 2820
<212> TYPE: DNA
<213> ORGANISM: EGT Optimized

<400> SEQUENCE: 5

atgaaaaaaa tcatcaccat gatgctgctg gttctgagcc tggttctggt ggcgtgtacc      60

ccgtctgaag aaccgccgac caccgttccg gatgtggaaa gcattgaatt taacatgacc     120

agcaccaccg tggcaccggg cgaacatacc ctggtggcga aagcgctgcc ggaaggcagc     180

aaccagcaga ttcgttttag cattcagggc attgtgagcg gcgtgagcat taccggcgat     240

aaactgaacg tgggcaacgc cgtggaagat ggcatgaaat ttaccgttgt ggcgaccagc     300

gtgtatgacc cgaccattcg tgccaccctg gaatttaccg tggttaacgt tggcgtggaa     360

gtggtggaaa ttcgtaccga agaagaactg cgcgcgattc ataccaacga aggcggcctg     420

agcctgagct atgtgctgat gaacgatatt gaactgaccg ccccgtggac cccgattggc     480

attgccgaag tggaaaccga tagcggccag attattccgg gcaccccgtt taacggcatt     540

tttaacggca acggctttac cattagcggc attctggtgg aaagcgaaga accgctgttt     600

aacgccggct tttttgccca gattggcgcc accgccattg tgaaaaacac cacctttgaa     660

ggcattgtga acgccaccgg ctggagcggc ggcattgccg gcattaacga aggcctgatt     720

gaaaacgttg ttagcaacgt tcgtgtgacc gtgaccggca ccagcgccgg tagcctggtg     780
```

-continued

```
agcgtgaacc gtggcctgat tcagtatgcc tatggcattg gcaaagtggt gagcgaaacc    840

aacccgaaca ccagcggtcg tagcgccggt ctggtggtgg cgaacgatgg cagcatgatt    900

gaagtgtatg gcgattatca ggcgctgggc accccgaact ataccgcctt tagcccgagc    960

accaacccga tgtatatgct gccgaccgtg gatatgaaaa ccagcagcac ctgggcgagc   1020

tttgatgccg atgtgtggta tatcgaaaac ggcacctatc cgctgctgaa acatgaaggc   1080

tttgtgccgc cggttattgt gccggaactg ggcattacca ttaaaaacac cgaactgaac   1140

catgatgtgg aagtgagcag cgaactgcag attaacgccg aagtgattaa cccggaaggt   1200

agcgaagtta ttgtttatgc cctgaaagaa gcggtggcgg gcgttgccat tagcgaaacc   1260

ggcctggtga cctttgatat taccaccatt gcggcgaact ttagctttac cgtggtggtg   1320

accattgatg gcaccgaagt gagcgccgaa aaaaccttta ccggcgtgta taacccggaa   1380

attgtggatg ataccgtcta tatcgaaacc gaaacccagc tgctgaacct gctggcgggc   1440

cagaccaacc cggataacct gagcaaaacc tttgtgctgc tgaatgacat tgtgctgacc   1500

agcaactgga ccgccattgg tattgccccg aacgaagatg aaggtattgt tggcgttccg   1560

tttaccggtg tgtttgatgg ccagggctac aaaattagcg gtattagcat gccgggtggc   1620

ggctggaaca aaggcttttt tggctatatc ggcaccaccg gcgtggtgaa aaatacccat   1680

ttcgaaggta acctggaagc gaacgcctgg tctggcgccc tggcggcgaa caacagcggc   1740

accattcagg atgtggtggt ggatatcgaa gtgtatgttt ggggcaacaa cggcggtgcc   1800

attgtggaac ataaccatgg cctgctgaaa aacattgtgg tgctgggtaa agcggtgagc   1860

gatagcggtc cgaccgccgt gggtctggtg gttaccaact ttggcaccct ggaaaacgtg   1920

tttgccaacg ccgataccgt gggcaccgcc aacctggtga gcaacggtgc cctggcggat   1980

gatggcaaac acattatcag cgcccaggat tttgtgaaag cgaccaccta tgccaacttt   2040

gatagcgcca tttggctgat tgtggatggc caggtgccgg ttctgattaa cgaagatacc   2100

gtgctgccgg aaaccgtggt gtatattgaa accgaagcgg aactgctgtc tctgctggcg   2160

ggtcaggtgg atccggaagc gctgtctaaa acctacaaac tgaaaaacga tatcgtgctg   2220

acctctaact ggacggcgat cggcatcgct ccgaatgaag atgagggcat cgtcggcgtc   2280

ccgttcaccg gcgtgttcga cggtcagggt tataaaattt ctggcatttc tatgccgggt   2340

ggtggttgga ataaaggttt cttcggttac attggcacca ccggtgttgt taaaaacact   2400

cactttgagg gtaatattga agcgaatgcc tggagcggcg ctctggccgc caacaactct   2460

ggcaccatta tggatgttgt tgtcgatatt gaagtttacg tgtggggcaa taatggtggc   2520

gccatcgttg aacacaatca cggtctgctg aaaaatatca ttgttctggg taaagccgtt   2580

tctgatggcg gtccgacggt ggtgggcctg gttgtgacga atttcggcac gctggaagat   2640

gtgtatgcca atgttgatac cgttggcacc ctgaatctgg tgagctttgg cagcgtggcc   2700

gatgatggca cccatatcat tagcgccagc aactttgtta aagcggaaac ctatgccaat   2760

tttagcagcg atgtgtggac cattattgat ggcagcaccc cggtgctgaa acaggcgtaa   2820
```

<210> SEQ ID NO 6
<211> LENGTH: 2509
<212> TYPE: DNA
<213> ORGANISM: EGT Optimized

<400> SEQUENCE: 6

```
atgcatctgg tgctgctgct gaaaagcaaa aaagataaat acatgaaaaa aatcagcctg     60

atcatgattt ttctgctgtc tattctgctg gtgagctgtg tggaaaaaga agaaccgaaa    120
```

-continued

```
ttcgatccgg ataaatacct ggatctggaa aacatcgttt tcgatgattt cgataacggc    180
attgatccga acatgtgggt gattggcaac agcaaatggg gcgtgggcaa cggcggcgtg    240
atttatgaaa acgtccatta caccaacgat ggcattgtgg tgctgcagac caacggcgat    300
ctgtatgatg gcccgctgcg tggcattggc aacacccatg gccgtcgtac cggcgccatg    360
attaccaccc gtgaagcgct gggtccgggc cgttttgaag ttcgtatgcg cattatgccg    420
cgttttggca gcaccaccgc catgtggacc tattattatg ataacggcat gaaccacgaa    480
attgatatcg aaagcaacgt ggaaaacgat tttcgtaaag tttggaccac caactggatc    540
agcctgaccg aatatagcac cgtgagcaac accctggatt ttgcccagaa cgattttgaa    600
tggcgtacct atcgttttga ttggtttacc gatccgaaac gtatcgatta ctacattgat    660
gaagtgctgg tgagcagcca gagcagctat gtgccggatc atgccggcga atttaacatt    720
ggcaactggt ttccggatgc ctgggcaggc gttccggatt ttgaaaccga ttatacctac    780
gtggattggt ttaaatacac cccgtttaaa gaacagccgt ataccccgac cccggcgaat    840
aaccagagcc cggcgaactt ttatccgagc gaaccgattg aacatccgat tgccaacctg    900
attagcaacg ccggcttcga aaccgatgcc ccggcatggc gttatccggt gaccagcggc    960
gtggaactgc tggaaggcga aggcctgaac ggcagccgtg gcatttttgt gccgcagaac   1020
gatattgcct atcagtttgt gaccggcctg gatgaaacct ttgaaatgac ctttagcgcc   1080
catgccaaac tgccgctgaa cggtagcggc tatgtgctgc tggaatttta tccggcggaa   1140
acccagaaaa ttgaccagta tatgatcgaa ttcaacagca gcgatgaaga ttttatcgcc   1200
gataccttct atggcaaaga atttaccttt aacgttccgc tgggcaccaa acgtgtggaa   1260
gtgagcctga ttggcggcga tagcggcatt tattttgacg acctgttctt caacctgacc   1320
aaaaaaccgc gtccggaaat tgtggaagaa ggcgacgacg ttcagcgtct gaacattgat   1380
ttcaaaaacg gcatcgatag caacgtgtgg gcggtggcga atcagcgttg gggcggcacg   1440
catcatggcg gtgtgatttt tcagaacgtt cactataccg aagaaggcaa cctgctgatt   1500
caggcgaacg gcgattatta tgaaggtccg ctgaaaggcg ttgaacagaa caacggcaaa   1560
cgtaccggcg gtgccattta taccaaagaa gcgtttggcc cgggtagctt tgaagtgaaa   1620
gcgaaaatca tgccgcgctt tggtgccacc acggcgtttt ggacctttaa ctatctggat   1680
ggcatcaaca gcgaaatcga ttttgaattc aacgtgggca acgattttag caccgtgtgg   1740
ctgaccaact ggctgaccga aaccaactat aacaactaca cccatcagat ggatagcttt   1800
cataacgatg gcaactggca tatttatcgc tttgaatggc ataccctgcc gaccccgcat   1860
attaaatact tcatcgacgg caaactggcg tataccgaac ataccaaagt gccgaccatg   1920
agcgcccgtt attggattgg cgtgtggttt ccgaacaact gggcgggtga tccgaacttt   1980
gaaaccgact atctggaagt ggaatacttc aaatacgaaa gctttccgga tcatccgtat   2040
gttgttggcc cgaccggtgc ctctagcccg accgcctttt atccgaccgc cccgattaaa   2100
aaaccggtga gcaacctgct gccgcatggc aacctggatt atgaaaccgg ctatatgctg   2160
accggcgatg ccgtgattag caatggcgaa ctgaaaaccg gcctgctggg cagcgccgaa   2220
agcctgatta ccggcctgaa cgatgccttt gaactgaccc tgaaactgaa agcgaaagcg   2280
agcaacaacg ccaccgttcg tattgaatac ctggataaag atctgaacgt tatcagcggc   2340
gaagatatta ttgtgagcaa tctgaacgcc aacaccttta ccaactttac cagcgtgatt   2400
aacctggttg aaggcacccg tgccattaac gttattttcg aaggcacgaa cattacctat   2460
```

-continued

```
gatgacctgt ttattaacct gacccacaaa gtgaactaat aagtcgacg           2509


<210> SEQ ID NO 7
<211> LENGTH: 438
<212> TYPE: PRT
<213> ORGANISM: Piscirickettsia salmonis

<400> SEQUENCE: 7

Met Lys Val Lys Met Ile Val Ala Ala Val Ala Val Ala Gly Leu Thr
1               5                   10                  15

Ala Thr Ala Ala Asn Ala Ala Asp Asn Gly Lys Leu Gln Leu Gln Ile
            20                  25                  30

Asn Gln Leu Lys Ala Gln His Thr Gln Leu Gln Gln Gln Val Ala Asn
        35                  40                  45

Leu Gln Gly Gln Gly Gln Thr Thr Gly Ala Val His Val Gly Ala Val
    50                  55                  60

Gly Gly Glu Leu Ile Ser Glu Asn Asn Tyr Asp Gly Arg Gly Leu Asp
65                  70                  75                  80

Leu Leu Lys Ser Leu Ala Lys Ala Gly Ser Asn Ala Pro Leu Leu Thr
                85                  90                  95

Ile Gly Gly Thr Leu Glu Ala Asp Ala Gln Met Asn Arg Asn Gly Asn
            100                 105                 110

Val Gly Ser Gly Ser Thr Ser Gly Asp Pro Ser Gly Leu Asn Tyr Thr
        115                 120                 125

Asp Gly Thr Ser Ser Ser Ala Phe Tyr Leu Asp Thr Ala Arg Ile Asp
    130                 135                 140

Ile Leu Ala His Val Asn Asp Trp Val Asn Gly Glu Ile Ser Tyr Asp
145                 150                 155                 160

Leu Asn Gly Asp Ser Gly Leu His Thr Gly Ser Leu Leu Val Gly Asn
                165                 170                 175

Leu Asn Gln Leu Pro Val Tyr Gly Gln Ile Gly Lys Phe Tyr Pro Asp
            180                 185                 190

Ala Gly Leu Phe Glu Leu Ala Ser Asp Asp Val Tyr Ser Ser Ser Leu
        195                 200                 205

Val Lys Arg Tyr Phe Arg Pro Asp Ala Gln Asn Gly Ala Ser Val Gly
    210                 215                 220

Phe Tyr Lys Ala Gly Leu His Thr Ser Leu Thr Ala Phe Lys Thr Ser
225                 230                 235                 240

Ala Pro Gln Ala Asn Ala Ala Asn Tyr Asn Gln Ala Thr Ser Asp Trp
                245                 250                 255

Ser Ala Gln Ala Asp Tyr Thr Phe Asn Ala Gly Gln Val Asn Ala Thr
            260                 265                 270

Ile Gly Ala Gly Tyr Leu Ser Asn Met Val Asn Thr Asn Asp Ser Phe
        275                 280                 285

Thr Ala Thr Gly Ala Gly Thr Gly Thr Gln Lys Asp Arg Leu Pro Met
    290                 295                 300

Ala Asn Val Ser Ala Lys Ile Gly Phe Gly Pro Phe Glu Ala Leu Ala
305                 310                 315                 320

Thr Tyr Ala Gln Thr Leu Lys Gly Leu Ala Asn Thr Thr Gly Gly Thr
                325                 330                 335

Thr Lys Leu Lys Ala Phe Asp Leu Glu Gly Ala Tyr His Phe Gln Ala
            340                 345                 350

Val Lys Pro Met Thr Val Met Leu Gly Tyr Ser Arg Thr Tyr Gly Phe
        355                 360                 365
```

-continued

Asp Lys Val Gly Pro Val Asp Gln Phe Ile Asp Gly Asn Thr Ala Ile
    370                 375                 380

Thr Ile Asn Asn Lys Lys Asp Gln Trp Leu Leu Gly Val Asn Ser Glu
385                 390                 395                 400

Val Phe Lys Asn Thr Thr Val Gly Leu Glu Tyr Ala Arg Val Gly Gln
                405                 410                 415

Leu Asp Ser Thr Gly Thr Asp Thr Asn Arg Tyr Asn Val Leu Thr Ala
            420                 425                 430

Asp Met Thr Val Lys Phe
        435

<210> SEQ ID NO 8
<211> LENGTH: 416
<212> TYPE: PRT
<213> ORGANISM: Piscirickettsia salmonis

<400> SEQUENCE: 8

Ala Asp Asn Gly Lys Leu Gln Leu Gln Ile Asn Gln Leu Lys Ala Gln
1               5                   10                  15

His Thr Gln Leu Gln Gln Gln Val Ala Asn Leu Gln Gly Gln Gly Gln
            20                  25                  30

Thr Thr Gly Ala Val His Val Gly Ala Val Gly Gly Glu Leu Ile Ser
        35                  40                  45

Glu Asn Asn Tyr Asp Gly Arg Gly Leu Asp Leu Leu Lys Ser Leu Ala
    50                  55                  60

Lys Ala Gly Ser Asn Ala Pro Leu Leu Thr Ile Gly Gly Thr Leu Glu
65                  70                  75                  80

Ala Asp Ala Gln Met Asn Arg Asn Gly Asn Val Gly Ser Gly Ser Thr
                85                  90                  95

Ser Gly Asp Pro Ser Gly Leu Asn Tyr Thr Asp Gly Thr Ser Ser Ser
            100                 105                 110

Ala Phe Tyr Leu Asp Thr Ala Arg Ile Asp Ile Leu Ala His Val Asn
        115                 120                 125

Asp Trp Val Asn Gly Glu Ile Ser Tyr Asp Leu Asn Gly Asp Ser Gly
    130                 135                 140

Leu His Thr Gly Ser Leu Leu Val Gly Asn Leu Asn Gln Leu Pro Val
145                 150                 155                 160

Tyr Gly Gln Ile Gly Lys Phe Tyr Pro Asp Ala Gly Leu Phe Glu Leu
                165                 170                 175

Ala Ser Asp Asp Val Tyr Ser Ser Ser Leu Val Lys Arg Tyr Phe Arg
            180                 185                 190

Pro Asp Ala Gln Asn Gly Ala Ser Val Gly Phe Tyr Lys Ala Gly Leu
        195                 200                 205

His Thr Ser Leu Thr Ala Phe Lys Thr Ser Ala Pro Gln Ala Asn Ala
    210                 215                 220

Ala Asn Tyr Asn Gln Ala Thr Ser Asp Trp Ser Ala Gln Ala Asp Tyr
225                 230                 235                 240

Thr Phe Asn Ala Gly Gln Val Asn Ala Thr Ile Gly Ala Gly Tyr Leu
                245                 250                 255

Ser Asn Met Val Asn Thr Asn Asp Ser Phe Thr Ala Thr Gly Ala Gly
            260                 265                 270

Thr Gly Thr Gln Lys Asp Arg Leu Pro Met Ala Asn Val Ser Ala Lys
        275                 280                 285

Ile Gly Phe Gly Pro Phe Glu Ala Leu Ala Thr Tyr Ala Gln Thr Leu
    290                 295                 300

-continued

```
Lys Gly Leu Ala Asn Thr Thr Gly Gly Thr Thr Lys Leu Lys Ala Phe
305                 310                 315                 320

Asp Leu Glu Gly Ala Tyr His Phe Gln Ala Val Lys Pro Met Thr Val
                325                 330                 335

Met Leu Gly Tyr Ser Arg Thr Tyr Gly Phe Asp Lys Val Gly Pro Val
            340                 345                 350

Asp Gln Phe Ile Asp Gly Asn Thr Ala Ile Thr Ile Asn Asn Lys Lys
        355                 360                 365

Asp Gln Trp Leu Leu Gly Val Asn Ser Glu Val Phe Lys Asn Thr Thr
    370                 375                 380

Val Gly Leu Glu Tyr Ala Arg Val Gly Gln Leu Asp Ser Thr Gly Thr
385                 390                 395                 400

Asp Thr Asn Arg Tyr Asn Val Leu Thr Ala Asp Met Thr Val Lys Phe
                405                 410                 415


<210> SEQ ID NO 9
<211> LENGTH: 367
<212> TYPE: PRT
<213> ORGANISM: Piscirickettsia salmonis

<400> SEQUENCE: 9

Met Ala Thr Leu Ala Val Gln Arg Glu Val Tyr Met Ser Asp Pro Asp
1               5                   10                  15

Asp Ile Ala Val Ile Leu Tyr Thr Ser Gly Thr Thr Gly Gln Pro Lys
            20                  25                  30

Gly Ala Met Leu Ser His Arg Ala Leu Val Gln Asn Cys Ile Asp Leu
        35                  40                  45

Asn Leu Cys Trp Gly Phe Thr Asp Ser Asp Val Leu Leu His Thr Leu
    50                  55                  60

Pro Leu Phe His Val His Gly Leu Phe Phe Ala Leu His Ser Val Leu
65                  70                  75                  80

Tyr Ala Ser Ala Ser Met Ile Leu Gln Ala Lys Phe Asp Pro Met Glu
                85                  90                  95

Val Ile Ile Ser Leu Ile Gln Ala Thr Val Phe Met Gly Val Pro Thr
            100                 105                 110

Tyr Tyr Thr Arg Leu Leu Lys Glu Ala Glu Phe Thr Gly Ser Arg Ala
        115                 120                 125

Ala Gln Val Arg Leu Phe Ile Ser Gly Ser Ala Pro Leu His Glu Lys
    130                 135                 140

Thr Phe Gln Gly Phe Tyr Gln Arg Thr Gly Lys Thr Leu Val Glu Arg
145                 150                 155                 160

Tyr Gly Met Ser Glu Thr Gly Ile Asn Thr Ser Asn Pro Leu His Gly
                165                 170                 175

Glu Arg Lys Phe Gly Thr Val Gly Thr Ala Leu Glu His Val Thr Val
            180                 185                 190

Arg Val Val Asp Glu Val Ser Glu Lys Val Leu Met Pro Gly Gln Thr
        195                 200                 205

Gly Glu Val Gln Val Gln Gly Arg His Leu Phe Ser Gly Tyr Trp Gln
    210                 215                 220

Lys Glu Asp Gln Thr Asp Gly Ala Phe Thr Cys Asp Gln Phe Phe Lys
225                 230                 235                 240

Thr Gly Asp Leu Gly Tyr Leu Asp Glu Gln Gly Tyr Leu Thr Leu Val
                245                 250                 255

Gly Arg Val Lys Asp Met Ile Ile Ser Gly Gly Leu Asn Ile Tyr Pro
```

-continued

```
            260                 265                 270

Lys Glu Ile Glu Thr Ala Ile Asp Arg Val Thr Gly Val Asn Glu Ser
        275                 280                 285

Ala Val Val Gly Val Ala His Glu Asp Leu Gly Glu Gly Val Val Ala
    290                 295                 300

Val Val Val Leu Gln Asp Asn Ala Asn Met Leu Ala Glu His Ile Ile
305                 310                 315                 320

Ala Tyr Cys Lys Ala Ser Leu Ala Asp Phe Lys Cys Pro Lys Lys Val
                325                 330                 335

Val Phe Ile Asp Gln Leu Pro Arg Asn Thr Met Gly Lys Val Gln Lys
            340                 345                 350

Asn Gln Leu Arg Gln Gln Tyr Gln Ala Ile Phe Ala Asp Ala His
        355                 360                 365


<210> SEQ ID NO 10
<211> LENGTH: 39
<212> TYPE: PRT
<213> ORGANISM: Piscirickettsia salmonis

<400> SEQUENCE: 10

Met Cys Lys Ile Pro Thr Glu Val Ala Thr Leu Thr Ala Glu Leu Asn
1               5                   10                  15

Lys Arg Leu Arg Leu Asn Met Phe Ala Cys Leu Tyr Ile Asp Phe Ile
            20                  25                  30

Pro Pro Cys Ile Asn Arg Tyr
        35


<210> SEQ ID NO 11
<211> LENGTH: 127
<212> TYPE: PRT
<213> ORGANISM: Piscirickettsia salmonis

<400> SEQUENCE: 11

Met Lys Asn Leu Ile Tyr Ala Gln Arg Leu Leu Tyr Phe Ala Val Leu
1               5                   10                  15

Ile Ala Val Ile Val Thr Phe Val Gln Pro Phe Leu Met Pro Ile Lys
            20                  25                  30

Leu Ala Asp Val Pro Leu Met Pro Leu Val Val Ala Ser Ile Tyr Ser
        35                  40                  45

Leu Ile Phe Ala Ala Ala Leu Ala Leu Ala Ala Tyr Lys Leu Pro Ser
    50                  55                  60

Lys Ala Gly Trp Pro Arg Phe Leu Leu Val Ile Leu Phe Ile Gly Asp
65                  70                  75                  80

Ala Met Pro Ala Val Lys Asn Trp Leu Val Leu Trp His Thr Thr Glu
                85                  90                  95

Leu Phe Ala Ile Ile Tyr Leu Met Lys Leu Met Leu Met Leu Ala Ala
            100                 105                 110

Ile Leu Leu Ser Leu Ser Lys Leu Ala Arg Asp Phe Tyr Lys Cys
        115                 120                 125


<210> SEQ ID NO 12
<211> LENGTH: 74
<212> TYPE: PRT
<213> ORGANISM: Piscirickettsia salmonis

<400> SEQUENCE: 12

Met Asp Asn Ala Ser Phe His Lys Ser Lys Gly Val Lys Glu Ala Ile
1               5                   10                  15
```

-continued

```
Glu Asp Ala Gly Cys His Leu Leu Phe Leu Pro Pro Tyr Ser Pro Asp
            20                  25                  30

Leu Asn Pro Ile Glu His Val Trp Ser Pro Leu Lys Asn Arg Val Arg
        35                  40                  45

Met Lys Leu Asp Gln Asp Glu Ile Asn Leu Glu Thr Ala Leu Ser Gln
    50                  55                  60

Val Met Lys Ser Met Ser Glu Thr Ile Arg
65                  70


<210> SEQ ID NO 13
<211> LENGTH: 81
<212> TYPE: PRT
<213> ORGANISM: Piscirickettsia salmonis

<400> SEQUENCE: 13

Met Pro Ser Pro Tyr Ser Tyr Asp Leu Arg Ile Arg Ala Leu Lys Met
1               5                   10                  15

Ile Asp Glu Gly Ile Pro Ile Thr Gln Ile Ser Lys Leu Leu Lys Ile
            20                  25                  30

Ser Arg Asp Thr Leu His Arg Trp Lys Asn Arg Arg Asp His Thr Gly
        35                  40                  45

Asp Val Lys Ala Arg Phe Gly Tyr Gln Thr Gly Tyr Asn His Lys Ile
    50                  55                  60

Ser Asp Met Lys Glu Phe Gln Lys Phe Ile Asp Arg Glu Phe Pro Gly
65                  70                  75                  80

Ser


<210> SEQ ID NO 14
<211> LENGTH: 319
<212> TYPE: PRT
<213> ORGANISM: Piscirickettsia salmonis

<400> SEQUENCE: 14

Leu Lys Ser Gln Lys Pro Pro Gly Asn Leu Thr Tyr Asn Leu Ser Ala
1               5                   10                  15

Pro Trp Ser Gln Leu Met Ala Leu Met Ser Pro Arg Lys Ser Leu Ala
            20                  25                  30

Arg Leu Ser Val Phe Leu Phe Gln Ser Gly Asp Phe Val Glu Lys Gly
        35                  40                  45

Arg Pro Leu Val Gln Leu Asp Asp Arg Thr Glu Gln Ala Asn Leu Leu
    50                  55                  60

Gln Tyr Lys Ala Lys Leu Lys Leu Asp Gln Leu Thr Tyr Asp Arg Asp
65                  70                  75                  80

Arg Ser Leu Leu Lys Lys Asn Ala Ile Ser Arg Gln Asp Val Asp Thr
                85                  90                  95

Ala Leu Thr Ser Leu Glu Gln Thr Lys Ala Gln Met Leu Ala Thr Glu
            100                 105                 110

Val Ser Ile Ser Gln Lys Leu Ile Arg Ala Pro Phe Ser Gly Lys Ile
        115                 120                 125

Gly Ile Arg Asn Val Asn Leu Gly Gln Tyr Ile Ser Pro Gly Thr Asn
    130                 135                 140

Ile Val Ser Leu Gln Ser Ile Asn Pro Leu His Val Asn Phe Ser Leu
145                 150                 155                 160

Pro Gln Glu Asp Met Asn Lys Ile Lys Leu Gly Gln Lys Ile Ser Ala
                165                 170                 175
```

-continued

```
His Val Asp Thr Phe Ala Gly Arg Glu Phe Thr Gly Thr Ile Thr Ala
            180                 185                 190

Met Asn Ser Glu Val Asp Ser Asn Thr Arg Thr Ile Glu Ile Gln Ala
        195                 200                 205

Ser Leu Pro Asn Pro Lys His Glu Leu Tyr Pro Gly Met Phe Thr Thr
    210                 215                 220

Val Gln Val Tyr Leu Pro Val Leu Pro Lys Val Leu Thr Leu Pro His
225                 230                 235                 240

Thr Ala Val Thr Tyr Thr Leu Tyr Gly Asn Ser Val Tyr Leu Ile Gln
                245                 250                 255

Leu Asn Gly Lys Lys Asn Gln Gln Gly Glu Pro Thr Gly Thr Val Thr
            260                 265                 270

Arg Ile Ser Ile Gln Thr Gly Asp Gln Arg Ser Asn Thr Val Val Ile
        275                 280                 285

Asn Lys Gly Leu Lys Ala Gly Asp Leu Ile Val Asp Gly Gly Gln Leu
    290                 295                 300

Lys Leu Glu Asn Gly Ala Ala Ile Ala Leu Lys Asn Thr Thr Gln
305                 310                 315


<210> SEQ ID NO 15
<211> LENGTH: 572
<212> TYPE: PRT
<213> ORGANISM: Piscirickettsia salmonis

<400> SEQUENCE: 15

Met Val Leu Ala Ile Gly Leu Val Val Asp Asp Ala Ile Ile Val Val
1               5                   10                  15

Glu Asn Val His Arg His Ile Glu Glu Gly Lys Gln Pro Phe Asp Ala
            20                  25                  30

Ala Leu Ile Gly Ala Arg Glu Ile Ala Ser Pro Val Ile Ala Met Thr
        35                  40                  45

Ile Thr Leu Ala Ala Val Tyr Ala Pro Ile Ala Phe Val Gly Gly Ile
    50                  55                  60

Thr Gly Ala Leu Phe Lys Glu Phe Ala Leu Thr Leu Ala Ala Ala Val
65                  70                  75                  80

Ile Val Ser Gly Val Ile Ala Leu Thr Leu Ser Pro Met Met Cys Ser
                85                  90                  95

Lys Leu Leu Val Ala Asp Asn Ala Asn Gly Gly Leu Ala His Trp Leu
            100                 105                 110

Asp Arg Gln Phe Leu Arg Leu Gln Gln Arg Tyr Glu Arg Ile Leu His
        115                 120                 125

His Thr Leu Glu His Arg Pro Val Val Leu Thr Phe Gly Leu Ile Ile
    130                 135                 140

Leu Val Gly Ile Phe Gly Met Leu Lys Met Thr Gln Lys Gln Leu Ala
145                 150                 155                 160

Pro His Glu Asp Gln Gly Phe Leu Ile Thr Phe Ala Ser Ala Pro Lys
                165                 170                 175

Tyr Ala Asn Ile Asn Tyr Val Glu Lys Tyr Ser Glu Glu Phe Ala Lys
            180                 185                 190

Ile Tyr Lys Ser Phe Pro Ala Ile Ala Asp Tyr Phe Ile Ile Asn Thr
        195                 200                 205

Thr Gly Ala Gly Thr Phe Pro Ser Gln Val Thr Ser Gly Ala Val Leu
    210                 215                 220

Lys Pro Trp Arg Asp Arg Ser Met Thr Thr Met Gln Leu Gln Pro Leu
225                 230                 235                 240
```

-continued

```
Leu Gln His Lys Leu Asn Gln Ile Thr Gly Leu Gln Ala Gln Ala Ile
                245                 250                 255

Gln Met Pro Ala Leu Pro Gly Pro Asp Gly Met Pro Ile Gln Phe Val
            260                 265                 270

Leu Thr Ser Thr Ala Asp Tyr Ser Val Leu Asn Asn Val Met Thr Lys
        275                 280                 285

Phe Lys Ala Ala Ala Asp Lys Ser Gly Leu Phe Leu Phe Ser Ser Ser
    290                 295                 300

Asp Leu Lys Phe Asn Lys Pro Lys Leu Asn Ile Ala Ile Asp Arg Ala
305                 310                 315                 320

Lys Ala Ala Gln Met Gly Ile Thr Met Gln Gln Ile Gly Ser Thr Leu
                325                 330                 335

Ser Thr Leu Leu Ser Gly Gly Lys Val Asn Tyr Phe Ser Leu Asp Gly
            340                 345                 350

Arg Ser Tyr Lys Val Ile Pro Gln Leu Ala Asp Asn Glu Arg Leu Thr
        355                 360                 365

Pro Gln Gln Leu Asn Asn Asn Tyr Ile Lys Thr Ala Ala Gly Ala Leu
    370                 375                 380

Ile Pro Leu Ser Thr Leu Ile Thr Leu Ser Thr Ser Ile Glu Pro Gly
385                 390                 395                 400

Thr Leu Asn Gln Phe Gln Gln Leu Asn Ser Ala Thr Leu Ser Ala Val
                405                 410                 415

Ala Met Pro Gly His Thr Asp Thr Glu Ala Leu Asn Phe Leu Lys Ala
            420                 425                 430

Gln Ala Thr Lys Leu Met Pro Lys Gly Met Ser Tyr Asn Phe Ser Gly
        435                 440                 445

Gln Ser Arg Thr Leu Val Gln Glu Gly Asn Ala Leu Ile Tyr Thr Phe
    450                 455                 460

Phe Phe Ala Leu Ile Met Ile Phe Leu Val Leu Ala Ala Gln Phe Glu
465                 470                 475                 480

Ser Phe Arg Asp Pro Phe Ile Ile Met Phe Thr Val Pro Met Ala Ile
                485                 490                 495

Phe Gly Ala Ala Ile Pro Met Ala Phe Gly Trp Thr Ser Leu Asn Ile
            500                 505                 510

Tyr Thr Glu Ile Gly Leu Val Thr Leu Ile Gly Leu Ile Thr Lys His
        515                 520                 525

Gly Ile Leu Met Val Gln Phe Ala Asn Asp Leu Gln Glu Gln Glu Gly
    530                 535                 540

Arg Asp Ile Arg Ser Ala Ile Glu His Ala Ala Gly Met Arg Leu Arg
545                 550                 555                 560

Pro Ile Leu Met Thr Thr Ala Ala Met Val Val Gly
                565                 570
```

<210> SEQ ID NO 16
<211> LENGTH: 2092
<212> TYPE: DNA
<213> ORGANISM: Piscirickettsia salmonis

<400> SEQUENCE: 16

```
ccaagaacta tcaaaaacta tataggcaaa gtataaagtc tgaagcttaa cctttgctta      60

aatgtacatc aggcttaagg tgatttctgt tgagtatttt cagagtctta agctcaattt     120

aatctttctt aaggttgaaa acaggctaaa atcaacattt tgataaaatt attaattttt     180

ttttattgtt cttttttaat cggtttttat cctaatttga tagatagtta tcgaaattca     240
```

-continued

```
ataagttttg tttttaattg aatttttttt acgagtttgg gttttacaaa gtgaatttac    300
ctggttatag tagccccagt tgcttaatag cacttaaatg tgtatccaga taaaaacaag    360
ttagggtaaa aagaatgaaa gtaaaaatga ttgttgcagc tgtagctgtt gcaggtttaa    420
cagcgactgc cgcaaatgcc gctgataatg gtaagcttca attacaaatc aaccaattga    480
aggcgcaaca cactcaactt caacagcaag ttgctaatct gcaaggtcaa ggccaaacta    540
ctggtgccgt tcacgttggc gctgttggtg gtgaactaat ctctgaaaat aactacgatg    600
gtcgtggctt agatcttctt aaatcattag cgaaagcagg cagcaatgca ccgttattaa    660
ctattggtgg tacgttagaa gctgatgcgc aaatgaaccg taacggtaat gttggatctg    720
gttctacttc tggtgaccct tctggcctta actatactga tggaactagc agttctgcat    780
tctatttaga tactgcacgt attgatatct tagcgcatgt gaatgactgg gttaacggtg    840
aaatctcgta tgacttaaat ggtgatagtg gtcttcacac tggtagcctt ttagtgggta    900
acctcaatca attaccagtt tatggtcaaa tcggtaaatt ctacccagat gcaggtttgt    960
ttgaattagc tagtgatgat gtttattctt ctagcttagt caagcgttat ttccgtccag   1020
atgcgcaaaa tggtgcatct gtaggcttct ataaagcagg cttacatact tctttaactg   1080
catttaaaac gtctgctcca caagctaatg ctgctaacta taaccaagca actagtgatt   1140
ggtctgcaca agcggattac acttttaatg caggtcaagt caatgccact ataggtgcag   1200
gttacttatc taatatggtg aataccaatg acagcttcac tgcaacaggt gcaggaactg   1260
gtacacaaaa agatcggcta ccgatggcta atgtaagcgc taagattggc tttggtccat   1320
ttgaagccct tgctacttat gctcaaacat taaaaggttt ggcgaatact acaggtggta   1380
caacgaagtt gaaagccttt gatttagaag gtgcttacca cttccaagct gtgaagccga   1440
tgactgtgat gttaggttat agccgtacat atggctttga taaggttgga cctgttgatc   1500
agtttattga tggtaatact gcgattacta tcaataacaa aaaagaccaa tggttattgg   1560
gtgtaaactc tgaagtattt aagaacacaa cggttggtct tgagtatgcg cgtgtaggtc   1620
agcttgatag cacaggtact gacactaacc gctacaacgt attgactgcg gatatgactg   1680
ttaagttcta atttaagagc tttaaagttt tcaaaaaggc gctgcggcgc cttttttttat   1740
gggcgttaat tattggtaat gtaggctagt atttaaattt gtgagtgatg agagatgaaa   1800
aatttaatct atgcacagcg tttgctttat tttgccgtat tgattgcggt gattgtcacc   1860
tttgttcagc catttctaat gccgattaag cttgctgatg tgcctttaat gccgctcgtg   1920
gtcgcttcga tttattcctt gatttttgct gcagctttag cattagctgc atataaatta   1980
ccgagcaaag ctggttggcc gcggtttttg ttggtgattt tatttattgg ggatgcgatg   2040
cctgcggtaa aaaactggct agtgctttgg catacgacgg agctttttgc ga           2092
```

ANTIGENS AND VACCINES AGAINST *PISCIRICKETTSIA SALMONIS*

CROSS-REFERENCE TO RELATED APPLICATIONS

This application is a non-provisional application that claims priority under 35 U.S.C. §119(e) of provisional applications U.S. Ser. No. 61/014,782 filed Dec. 19, 2007, the contents of which are hereby incorporated by reference in its entirety.

BACKGROUND OF THE INVENTION

1. Field of Invention

The present invention relates to novel proteins from *Piscirickettsia salmonis*. The present invention also pertains to the nucleic acids that encode these proteins. The present invention further relates to a process of preparing a vaccine against salmonid rickettsial septicemia (SRS) using the proteins as antigens, or the nucleic acids in bacterial hosts to express such antigens. The present invention also relates to bacterins and viral antigens that can be combined to form a vaccine against SRS. The present invention also pertains to vaccines for preventing SRS, as well as preventing other bacterial and/or viral infections in fish.

2. Background

Salmonid rickettsial septicemia (SRS), also known as piscirickettsiosis, is a fatal disease in salmonids. Although the etiological agent for SRS was identified in the late 1980's as *Piscirickettsia salmonis*, antibiotics proved to be an unsuccessful treatment, due, at least in part, to the intracellular nature of this bacterium [Bravo and Campos, *FHS/AFS Newsl.* 17:3 (1989); U.K. Patent Application 2 356 632]. As a consequence of the lack of a viable treatment, millions of farmed salmon die of SRS each year just in southern Chile alone [Smith et al., *Dis. Aquat. Organ.* 37(3):165-172 (1999)]. In addition, recent reports demonstrate a link between *Piscirickettsia*-like bacteria and disease syndromes in non-salmonid fish [see, Mauel and Miller, *Veterin. Microbiol.* 87(4):279-289 (2002)].

The Salmonidae family (salmonids) includes salmon, trout, char, and whitefish. Salmonids serve both as a food source and as a game fish. Moreover, in countries such as Chile, Norway, Canada, the United Kingdom, Ireland, and the United States, salmonids have become an important commercial product due, at least in part, to the ability of fish farmers to artificially spawn, incubate and raise the salmonids in captivity.

Unlike fish originating in the wild, those raised in captivity are amenable to prophylactic treatments such as vaccination. So far, several potential vaccines have been described, such as one based on a specific *Piscirickettsia salmonis* antigen, a 17 kDa lipoprotein OspA [U.K. Patent Application 2 356 632; see also WO 01/68865 A2]. Additional potential vaccines against *Piscirickettsia salmonis* are described by WO05035558 A2 and WO2006037383 A1, the contents of which are hereby incorporated by reference in their entireties. These published international patent applications describe an isolated *Piscirickettsia salmonis* $^{Ps}$p45 protein and antigenic fragments thereof, as well as other SRS antigens.

The coding sequence for $^{Ps}$p45 protein is contained by a recombinant Chilean strain of *Yersinia ruckeri* that has been deposited (BCCM accession No. LMG P-22044). The nucleotide coding sequence of the $^{Ps}$p45 protein within the deposited recombinant *Yersinia ruckeri* is included within SEQ ID NO: 16. The amino acid sequence of the $^{Ps}$p45 protein within the deposited recombinant *Yersinia ruckeri* is SEQ ID NO: 7 [the amino acid sequence of SEQ ID NO: 8 is identical to that of SEQ ID NO: 7, except SEQ ID NO: 8 lacks the sequence for the signal peptide.]

In addition to *Piscirickettsia salmonis*, other pathogens are known to cause disease in farmed fish, including salmon. One such pathogen is the Infectious Pancreatic Necrosis virus (IPN virus), which is an unenveloped, icosahedral, bisegmented dsRNA virus. The IPN virus contains one main structural protein, VP2 (52 kDa) and three additional proteins, VP1 (90 kDa), VP3 (30 kDa) and VP4 (28 kDa). VP2 is the main protein of the outer capsid and is therefore immunologically important in recognition and bonding of the virus. VP1 is thought to be a polymerase, whereas VP3 and VP4 are internal proteins. VP4 is believed to correspond to a form of VP3 fragment formed during viral differentiation [see, WO 02/38770 A1, the contents of which are hereby incorporated by reference in their entireties]. Nucleotide and amino acid sequences for VP2 and VP3 have been determined [see, Havarstein et al., *J. Gen. Virol.* 71:299-308 (1990); Pryde et al., *Archives of Vir.* 129:287-293 (1992)].

There, therefore remains a need to provide new safe and effective vaccines against *Piscirickettsia salmonis*. In addition, there remains a need to identify new antigens from *Piscirickettsia salmonis* that can be used in such vaccines. Furthermore, there is a need to obtain nucleic acids that encode such antigens. In addition, there is a need to provide methods of vaccinating fish to protect them from *Piscirickettsia salmonis* and *Piscirickettsia*-like bacteria. Furthermore, there is a need to provide vaccines that can protect fish against *Piscirickettsia salmonis* and other unrelated pathogens, particularly those of commercial importance, such as the IPN virus.

The citation of any reference herein should not be construed as an admission that such reference is available as "prior art" to the instant application.

SUMMARY OF THE INVENTION

The present invention provides isolated, recombinant, or both isolated and recombinant proteins from *Piscirickettsia salmonis*, as well as antigenic fragments thereof. One such protein is $^{Ps}p_1 90$, a 90 kDa protein (ORF1), as described below. Another 90 kDa protein is $^{Ps}p_2 90$, (ORF 2) as described below. $^{Ps}p_1 90$ and $^{Ps}p_2 90$ can be expressed from any suitable nucleic acid that encodes one or both of them, respectively, e.g., either DNA or RNA. In addition, $^{Ps}p_1 90$ or $^{Ps}p_2 90$ can be used as antigens in vaccines against SRS, either alone, or in combination with each other and/or other antigens.

The present invention further provides nucleic acids that encode the isolated and/or recombinant proteins from *Piscirickettsia salmonis* and/or antigenic fragments of the proteins. Furthermore, the present invention provides nucleotide probes and PCR primers that can be used, e.g., to identify such nucleic acids that encode these proteins. In addition, the present invention provides recombinant vectors that encode the *Piscirickettsia salmonis* proteins of the present invention, or fragments thereof, such as recombinant viruses and bacteria. Corresponding attenuated or killed recombinant bacteria, e.g., bacterins prepared from the recombinant bacterial vectors are also provided.

The present invention further provides vaccines that comprise *Piscirickettsia salmonis* proteins of the present invention and/or antigenic fragments of these antigens. These antigens may be placed into a vaccine in any number of forms including as a recombinant protein itself, and/or as a recombinant protein expressed by a recombinant vector such as a recombinant gram negative bacterium, or as a naked DNA. In a particular embodiment of the present invention, the recombinant gram negative bacterium is a recombinant *E. coli* cell.

Preferably the recipient of a vaccine of the present invention receives protection from *Piscirickettsia salmonis*. In one embodiment, the vaccine comprises recombinant *E. coli* that encode and express the $^{Ps}p_1 90$ and/or $^{Ps}p_2 90$ proteins and/or antigenic fragments of the $^{Ps}p_1 90$ and/or $^{Ps}p_2 90$ protein. In a particular embodiment of this type, such recombinant *E. coli* are inactivated prior to being added to the vaccine and/or prior to the administration of the vaccine to the animal subject. In addition, booster vaccines are also provided by the present invention.

Antibodies that bind to the *Piscirickettsia salmonis* proteins of the present invention are also provided. Such antibodies can be used: to demonstrate the presence of, identify, and/or purify the proteins of the present invention.

Accordingly, the present invention provides a $^{Ps}p_1 90$ protein that comprises an amino acid sequence comprising at least 60% identity with the amino acid sequence of SEQ ID NO: 2. In a particular embodiment of this type the $^{Ps}p_1 90$ protein comprises an amino acid sequence comprising at least 75% identity with the amino acid sequence of SEQ ID NO: 2. In another embodiment of this type the $^{Ps}p_1 90$ protein comprises an amino acid sequence comprising at least 90% identity with the amino acid sequence of SEQ ID NO: 2. In still another embodiment of this type the $^{Ps}p_1 90$ protein comprises an amino acid sequence comprising at least 95% identity with the amino acid sequence of SEQ ID NO: 2.

In yet another embodiment of this type the $^{Ps}p_1 90$ protein comprises an amino acid sequence comprising SEQ ID NO: 2 that comprises one or more conservative amino acid substitutions. In still another embodiment the $^{Ps}p_1 90$ protein comprises an amino acid sequence comprising SEQ ID NO: 2 that comprises one to ten amino acid substitutions. In a particular embodiment of this type the $^{Ps}p_1 90$ protein comprises an amino acid sequence of SEQ ID NO: 2 that comprises one to ten conservative amino acid substitutions. In a specific embodiment, the $^{Ps}p_1 90$ protein comprises the amino acid sequence of SEQ ID NO: 2. In another embodiment, the $^{Ps}p_1 90$ protein consists essentially of the amino acid sequence of SEQ ID NO: 2 . *P. salmonis* variants of the $^{Ps}p_1 90$ protein that comprises the amino acid sequence of SEQ ID NO: 2 are also included as part of the present invention.

Preferably, all of the $^{Ps}p_1 90$ proteins of the present invention bind to an antibody elicited by the $^{Ps}p_1 90$ protein that has the amino acid sequence of SEQ ID NO: 2. More preferably, when a $^{Ps}p_1 90$ protein of the present invention is included as an antigen in a vaccine administered to salmonids, the vaccine provides protection against SRS to the vaccinated salmonids.

The present invention also provides a $^{Ps}p_2 90$ protein that comprises an amino acid sequence comprising at least 60% identity with the amino acid sequence of SEQ ID NO: 4. In a particular embodiment of this type the $^{Ps}p_2 90$ protein comprises an amino acid sequence comprising at least 75% identity with the amino acid sequence of SEQ ID NO: 4. In another embodiment of this type the $^{Ps}p_2 90$ protein comprises an amino acid sequence comprising at least 90% identity with the amino acid sequence of SEQ ID NO: 4. In still another embodiment of this type the $^{Ps}p_2 90$ protein comprises an amino acid sequence comprising at least 95% identity with the amino acid sequence of SEQ ID NO: 4.

In yet another embodiment of this type the $^{Ps}p_2 90$ protein comprises an amino acid sequence comprising SEQ ID NO: 4 that comprises one or more conservative amino acid substitutions. In still another embodiment the $^{Ps}p_2 90$ protein comprises an amino acid sequence comprising SEQ ID NO: 4 that comprises one to ten amino acid substitutions. In a particular embodiment of this type the $^{Ps}p_2 90$ protein comprises an amino acid sequence of SEQ ID NO: 4 that comprises one to ten conservative amino acid substitutions. In a specific embodiment, the $^{Ps}p_2 90$ protein comprises the amino acid sequence of SEQ ID NO: 4. In another embodiment, the $^{Ps}p_2 90$ protein consists essentially of the amino acid sequence of SEQ ID NO: 4 . *P. salmonis* variants of the $^{Ps}p_2 90$ protein that comprises the amino acid sequence of SEQ ID NO: 4 are also included as part of the present invention.

Preferably, all of the $^{Ps}p_2 90$ proteins of the present invention bind to an antibody elicited by the $^{Ps}p_2 90$ protein that has the amino acid sequence of SEQ ID NO: 4. More preferably, when a $^{Ps}p_2 90$ protein of the present invention is included as an antigen in a vaccine administered to salmonids, the vaccine provides protection against SRS to the vaccinated salmonids.

The present invention also provides antigenic fragments of all of the *P. salmonis* proteins of the present invention. In a particular embodiment, the antigenic fragment is of the $^{Ps}p_1 90$ protein having the amino acid sequence of SEQ ID NO: 2. In another particular embodiment, the antigenic fragment is of the $^{Ps}p_2 90$ protein having the amino acid sequence of SEQ ID NO: 4. The antigenic fragments of the present invention can be in any form including but not limited to: isolated, recombinant, chemically synthesized, both recombinant and isolated, or both chemically synthesized and isolated.

The present invention further provides chimeric polypeptides that comprise a $^{Ps}p_1 90$ protein of the present invention or antigenic fragment thereof, and/or a $^{Ps}p_2 90$ protein of the present invention or antigenic fragment thereof. In one such embodiment, the chimeric polypeptide comprises the $^{Ps}p_1 90$ protein having the amino acid sequence of SEQ ID NO: 2. In an alternative embodiment, the chimeric polypeptide comprises the $^{Ps}p_2 90$ protein having the amino acid sequence of SEQ ID NO: 4. In another embodiment, the chimeric polypeptide comprises an antigenic fragment of a $^{Ps}p_1 90$ protein of the present invention that has the amino acid sequence of SEQ ID NO: 2. In still another embodiment, the chimeric polypeptide comprises an antigenic fragment of the $^{Ps}p_2 90$ protein that comprises the amino acid sequence of SEQ ID NO: 4. The chimeric polypeptides of the present invention can be in any form including but not limited to: isolated, recombinant, chemically synthesized, both recombinant and isolated, or both chemically synthesized and isolated.

The present invention further provides antibodies elicited by the $^{Ps}p_1 90$ or $^{Ps}p_2 90$ proteins of the present invention, including those elicited by a chimeric polypeptide of the present invention. In one embodiment, the antibody is solicited by the $^{Ps}p_1 90$ protein having the amino acid sequence of SEQ ID NO: 2. In an alternative embodiment, the antibody is solicited by the $^{Ps}p_2 90$ protein having the amino acid sequence of SEQ ID NO: 4.

The present invention also provides antibodies solicited by an antigenic fragment of a $^{Ps}p_1 90$ and/or a $^{Ps}p_2 90$ protein of the present invention. In one such embodiment, the antibody is solicited by an antigenic fragment of a $^{Ps}p_1 90$ protein of the present invention having the amino acid sequence of SEQ ID NO: 2. In another embodiment, the antibody is solicited by an antigenic fragment of the $^{Ps}p_2 90$ protein having the amino acid sequence of SEQ ID NO: 4.

In another aspect of the present invention, nucleic acids are provided which encode: the $^{Ps}p_1 90$ proteins, the $^{Ps}p_2 90$ proteins, the antigenic fragments of these $^{Ps}p_1 90$ proteins and/or $^{Ps}p_2 90$ proteins, and/or the corresponding chimeric polypeptides of the present invention. Any of these nucleic acids can further comprise heterologous nucleotide sequences. The nucleic acids of the present invention can be in any form including but not limited to: isolated, recombinant, chemically synthesized, both recombinant and isolated, or both chemically synthesized and isolated.

In a particular embodiment, a nucleic acid of the present invention encodes a $^{Ps}p_1 90$ protein that comprises the amino acid sequence of SEQ ID NO: 2. In a particular embodiment of this type the nucleic acid comprises the nucleotide sequence of SEQ ID NO: 1. In an alternative embodiment the nucleic acid comprises the nucleotide sequence of SEQ ID NO: 5.

In another embodiment, a nucleic acid of the present invention encodes a $^{Ps}p_2 90$ protein that comprises the amino acid sequence of SEQ ID NO: 4. In a particular embodiment of this type the nucleic acid comprises the nucleotide sequence of SEQ ID NO: 3. In another embodiment the nucleic acid comprises the nucleotide sequence of SEQ ID NO: 6.

The present invention also provides nucleic acids (e.g., DNA molecules) of 18 nucleotides or more that hybridize under stringent conditions with the nucleic acid having the nucleotide sequence of SEQ ID NO: 1. In a particular embodiment, the nucleic acid comprises 120 nucleotides or more and hybridizes under stringent conditions with the nucleic acid having the nucleotide sequence of SEQ ID NO: 1. In another embodiment, the nucleic acid comprises 300 nucleotides or more and hybridizes under stringent conditions with the nucleic acid having the nucleotide sequence of SEQ ID NO: 1. In still another embodiment, the nucleic acid comprises 900 nucleotides or more and hybridizes under stringent conditions with the nucleic acid having the nucleotide sequence of SEQ ID NO: 1. In yet another embodiment the nucleic acid comprises between 2000 to 3000 nucleotides and hybridizes under stringent conditions with the nucleic acid having the nucleotide sequence of SEQ ID NO: 1. In a related embodiment, the DNA molecule encodes a $^{Ps}p_1 90$ protein and hybridizes under stringent conditions with the nucleic acid having the nucleotide sequence of SEQ ID NO: 1.

The present invention also provides nucleic acids (e.g., DNA molecules) of 18 nucleotides or more that hybridize under stringent conditions with the nucleic acid having the nucleotide sequence of SEQ ID NO: 3. In a particular embodiment, the nucleic acid comprises 120 nucleotides or more and hybridizes under stringent conditions with the nucleic acid having the nucleotide sequence of SEQ ID NO: 3. In another embodiment, the nucleic acid comprises 300 nucleotides or more and hybridizes under stringent conditions with the nucleic acid having the nucleotide sequence of SEQ ID NO: 3. In still another embodiment, the nucleic acid comprises 900 nucleotides or more and hybridizes under stringent conditions with the nucleic acid having the nucleotide sequence of SEQ ID NO: 3. In yet another embodiment the nucleic acid comprises between 1500 to 2600 nucleotides and hybridizes under stringent conditions with the nucleic acid having the nucleotide sequence of SEQ ID NO: 3. In a related embodiment, the DNA molecule encodes a $^{Ps}p_2 90$ protein and hybridizes under stringent conditions with the nucleic acid having the nucleotide sequence of SEQ ID NO: 3.

The present invention also provides vectors that comprise one or more of the nucleic acids of the present invention. In one embodiment of this type, the vector is an expression vector. Preferably the nucleic acids of the present invention are operatively linked to a transcriptional control sequence in the expression vectors.

The expression vectors of the present invention can be used to express one or more $^{Ps}p_1 90$ proteins, $^{Ps}p_2 90$ proteins, antigenic fragments of the $^{Ps}p_1 90$ proteins and/or $^{Ps}p_2 90$ proteins, and/or corresponding chimeric polypeptides. In one such embodiment, the expression vector is a plasmid that can function in *E. coli*. In a particular embodiment, the expression vector is the EGT1 plasmid. In one such embodiment, the expression vector is an EGT1 plasmid that expresses $^{Ps}p_1 90$ that has the amino acid sequence of SEQ ID NO: 2, and which has the BCCM accession No. LMBP 5690. In an alternative embodiment, the expression vector is an EGT1 plasmid that expresses $^{Ps}p_2 90$ that has the amino acid sequence of SEQ ID NO: 4, and which has the BCCM accession No. LMBP 5691.

The present invention further provides host cells that comprise the vectors of the present invention. In a particular embodiment, the host cell expresses one or more $^{Ps}p_1 90$ proteins, $^{Ps}p_2 90$ proteins, antigenic fragments of the $^{Ps}p_1 90$ proteins and/or $^{Ps}p_2 90$ proteins, and/or corresponding chimeric polypeptides. In one embodiment the host cell comprises a plasmid that expresses $^{Ps}p_1 90$ that comprises the amino acid sequence of SEQ ID NO: 2. In a particular embodiment of this type, the plasmid is an EGT1 plasmid that has the BCCM accession No. LMBP 5690. In another embodiment the host cell comprises a plasmid that expresses $^{Ps}p_2 90$ that comprises the amino acid sequence of SEQ ID NO: 4. In a particular embodiment of this type, the plasmid is an EGT1 plasmid that has the BCCM accession No. LMBP 5691. Preferably, the host cell is an *E. coli* cell.

The present invention also provides methods for expressing and/or producing a one or more $^{Ps}p_1 90$ proteins, $^{Ps}p_2 90$ proteins, antigenic fragments of the $^{Ps}p_1 90$ proteins and/or $^{Ps}p_2 90$ proteins, and/or corresponding chimeric polypeptides. One such embodiment is culturing a host cell of the present invention in a culture medium. In a particular embodiment, the method further comprises isolating the $^{Ps}p_1 90$ protein(s), $^{Ps}p_2 90$ protein(s), antigenic fragment(s) of the $^{Ps}p_1 90$ protein(s) and/or $^{Ps}p_2 90$ protein(s), and/or corresponding chimeric polypeptide(s). In one such embodiment, the host cell is an *E. coli* cell. In a particular embodiment the host cell comprises a EGT1 plasmid that expresses $^{Ps}p_1 90$ that comprises the amino acid sequence of SEQ ID NO: 2. In a particular embodiment of this type, the plasmid is an EGT1 plasmid that has the BCCM accession No. LMBP 5690. In another embodiment the host cell comprises a EGT1 plasmid that expresses $^{Ps}p_2 90$ that comprises the amino acid sequence of SEQ ID NO: 4. In a particular embodiment of this type, the plasmid is an EGT1 plasmid that has the BCCM accession No. LMBP 5691.

In another aspect of the present invention, immunogenic compositions are provided comprising the proteins, and/or antigenic fragments, and/or recombinant host cells, and/or bacterins of the present invention. In a preferred embodiment of this type, an immunogenic composition of the present invention is a vaccine. Accordingly, the vaccines of the present invention can comprise any of the immunogenic compositions of the present invention. Preferred vaccines protect fish against SRS, either alone or in multivalent vaccines that may also protect against other pathogens. In a related embodiment, a vaccine is a naked DNA vaccine that comprises a recombinant DNA vector that comprises an antigen of the present invention or an antigenic fragment thereof.

Immunogenic compositions of the present invention comprise antigenically effective amounts of a $^{Ps}p_1 90$ protein of the present invention and/or of an antigenic fragment thereof; and/or an antigenically effective amount of a $^{Ps}p_2 90$ protein of the present invention and/or of an antigenic fragment thereof; and/or antigenically effective amounts of a mixture of a $^{Ps}p_190$ protein of the present invention and/or of an antigenic fragment thereof and/or a $^{Ps}p_290$ protein of the present invention and/or of an antigenic fragment thereof.

In a particular embodiment, the immunogenic composition comprises a bacterin that comprises the plasmid having the BCCM accession No. LMBP 5690. In another embodiment the immunogenic composition comprises a bacterin that comprises the plasmid having the BCCM accession No. LMBP 5691. In still another embodiment, the immunogenic composition comprises both a bacterin that comprises the plasmid having the BCCM accession No. LMBP 5690 and a bacterin that comprises the plasmid having the BCCM accession No. LMBP 5691.

The vaccines of the present invention can further include an adjuvant. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, and dinitrophenol.

A vaccine and/or immunogenic composition of the present invention can further comprise one or more additional *P. salmonis* proteins or an antigenic fragment thereof. In one such embodiment the *P. salmonis* protein is the $^{Ps}45$ protein. In a particular embodiment of this type, the $^{Ps}45$ protein can comprise the amino acid sequence of SEQ ID NO: 8. In another embodiment, the vaccine and/or immunogenic composition can further comprise a bacterin comprised of a *Yersinia ruckeri* cell having the BCCM accession No. of LMG P-22044. In another embodiment, the bacterin is a *Yersinia ruckeri* cell BCCM accession No. LMG P-22511. In still another vaccine and/or immunogenic composition a bacterin comprising both the *Yersinia ruckeri* cell having the BCCM accession No. of LMG P-22044 and a *Yersinia ruckeri* cell BCCM accession No. LMG P-22511 is included.

In another embodiment, a vaccine of the present invention further comprises one or more antigens obtained from an Infectious Pancreatic Necrosis (IPN) virus. These recombinant proteins are preferably expressed by transformed yeast, *Pichia pastoris*. In one such embodiment, the antigen obtained from the IPN virus is the VP2 var protein or antigenic fragment thereof. In another embodiment the antigen obtained from the IPN virus is the VP3 protein or antigenic fragment thereof. In a preferred embodiment, the vaccine comprises both the VP2 var protein or antigenic fragment thereof and the VP3 protein or antigenic fragment thereof.

In one embodiment, an antigen is the portion of the VP2 var protein obtained from the transformed *Pichia pastoris* cell, BCCM Accession No. IHEM 20069. In another embodiment of this type, an antigen is the portion of the VP2 var protein obtained from the transformed *Pichia pastoris* cell, BCCM Accession No. IHEM 20070. In still another embodiment, an antigen is the portion of the VP3 protein obtained from the transformed *Pichia pastoris* cell, BCCM Accession No. IHEM 20071. In yet another embodiment, an antigen is the portion of the VP3 protein obtained from the transformed *Pichia pastoris* cell, BCCM Accession No. IHEM 20072. In a particular embodiment the vaccine comprises antigens from transformed *Pichia pastoris* cells, BCCM Accession No. IHEM 20069 and BCCM Accession No. IHEM 20071. In another embodiment the vaccine comprises antigens from transformed *Pichia pastoris* cells. BCCM Accession No. IHEM 20070, and BCCM Accession No. IHEM 20072.

In still another embodiment a vaccine of the present invention comprises one or more antigens obtained from *Aeromonas salmonicida*. In a particular embodiment, the *Aeromonas salmonicida* comprising the antigens is prepared from a culture grown under iron-depleted conditions. In another embodiment, the *Aeromonas salmonicida* comprising the antigens is prepared from a culture grown under iron-supplemented conditions. In a preferred embodiment, two sets of *Aeromonas salmonicida* antigens are employed in the vaccine, one set from a culture grown under iron-depleted conditions the other set from a culture grown under iron-supplemented conditions. In a particular embodiment, a multivalent vaccine comprises antigens from *Piscirickettsia salmonis*, IPN, and *Aeromonas salmonicida*.

The present invention also provides methods of protecting a fish from salmonid rickettsial septicemia (SRS), or SRS along with one or more other pathogenic disease(s) through the vaccination of the fish with a vaccine of the present invention. In a particular embodiment the other disease is Infectious Pancreatic Necrosis. In another embodiment the other disease is furunculosis. In still another embodiment the method of protecting the fish includes protecting against SRS, Infectious Pancreatic Necrosis, and furunculosis (caused by *Aeromonas salmonicida*).

The vaccines of the present invention can be administered by any method. In one embodiment a vaccine of the present invention is administered by immersion. In another embodiment a vaccine of the present invention is administered by injection. In yet another embodiment a vaccine of the present invention is administered by oral administration.

In addition, related booster vaccines are also provided by the present invention. The administration of a given booster vaccine is preferably performed through oral administration.

Any fish may be the recipient of the vaccines of the present invention. Examples of recipient fish are listed below. In a particular embodiment, the fish is a teleost. In a preferred embodiment, the telost is a salmonid. In a more preferred embodiment the salmonid is a salmon. In one such embodiment the salmon is a *Salmo salar* (Atlantic salmon). In another embodiment the salmon is an *Oncorhynchus kisutch* (coho salmon). In yet another embodiment the salmonid is an *Oncorhynchus mykiss* (rainbow trout).

Accordingly, it is a principal object of the present invention to provide a vaccine that protects salmonids against SRS.

It is a further object of the present invention to provide a vaccine that protects fish from salmonid rickettsial septicemia (SRS) and Infectious Pancreatic Necrosis (IPN).

It is a further object of the present invention to provide an effective way to protect against assorted fish infections by providing a multivalent vaccine.

It is a further object of the present invention to provide a protocol that can lead to the successful vaccination of fish in captivity.

It is a further object of the present invention to provide a DNA construct that encodes the $^{Ps}p_190$ protein or variant thereof.

It is a further object of the present invention to provide a DNA construct that encodes the $^{Ps}p_290$ protein or variant thereof.

It is a further object of the present invention to provide a polypeptide having an amino acid sequence of SEQ ID NO: 2, or an antigenic fragment thereof.

It is a further object of the present invention to provide a polypeptide having an amino acid sequence of SEQ ID NO: 4, or an antigenic fragment thereof.

It is a further object of the present invention to provide a recombinant subunit vaccine against SRS.

It is a further object of the present invention to provide inactivated recombinant bacterial vectors encoding specific antigens to be used in vaccines against SRS.

These and other aspects of the present invention will be better appreciated by reference to the following drawings and Detailed Description.

DETAILED DESCRIPTION OF THE INVENTION

Figure 1:
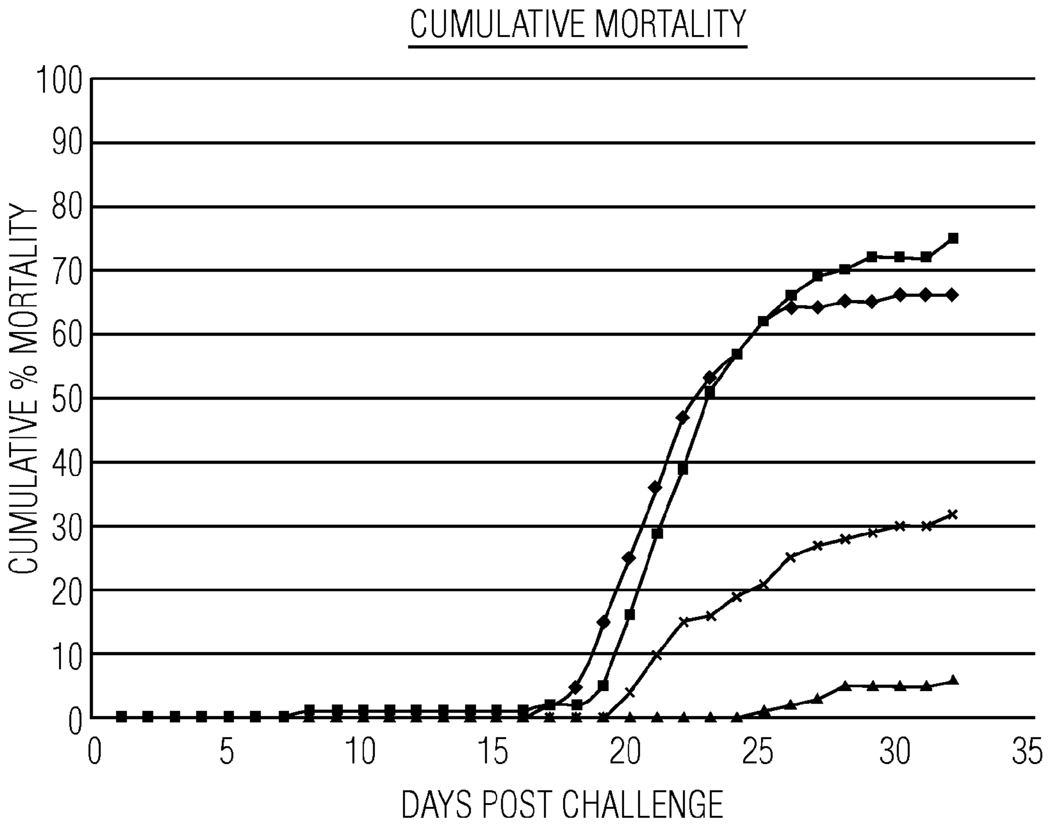
FIG. 1 illustrates the cumulative percent mortality in different test groups of fish after vaccination. The curves show the results of the saline controls denoted by diamonds, the adjuvant controls denoted by squares, the 90 kDa ORF 1 [$^{Ps}p_1 90$] vaccine denoted by triangles, and the 90 kDa ORF 2 [$^{Ps}p_2 90$] vaccine denoted by "X"'s.

The present invention provides safe and effective vaccines to protect fish against *Piscirickettsia salmonis* infections. In addition, the present invention provides methods of vaccinating fish to protect them from *Piscirickettsia salmonis* and *Piscirickettsia*-like bacteria. Moreover, the present invention provides vaccines that can protect vaccinated fish from *Piscirickettsia salmonis* and other unrelated pathogens, such as the IPN virus. Methods of making the vaccines of the present invention are also provided. The vaccines of the present invention (including booster vaccines) can be administered to fish by a number of means including by immersion, by injection, and/or through oral administration.

Notably, US Published Patent Application No. US20070207165 (A1) and WO2006037383(A1) specifically teach the use a recombinant *Yersinia ruckeri* vector to express *P. salmonis* proteins, and indeed, exemplify the successful use of *Yersinia ruckeri* to express the $^{Ps}p45$ protein. However, after considerable time and effort, *Yersinia ruckeri* proved to be an inappropriate host cell for expressing either $^{Ps}p_1 90$ or $^{Ps}p_2 90$ due both to instability, and the inability to demonstrate expression of these proteins. Surprisingly, and contrary to the earlier teachings of US20070207165 (A1) and WO2006037383(A1), *E. coli* cells proved to be the preferred recombinant host cell to express either $^{Ps}p_1 90$ or $^{Ps}p_2 90$.

Accordingly, in a particular aspect of the present invention the $^{Ps}p_1 90$ and $^{Ps}p_2 90$ proteins are expressed in recombinant *E. coli* host cells containing pEGT1 plasmids. Two corresponding recombinant *E. coli* HMS174(DE3)/pEGT1 plasmids encoding these proteins were deposited with the:

Belgian Coordinated Collections of Microorganisms (BCCM) under the terms of the Budapest Treaty and represented by:

BCCM/LMBP
Department of Molecular Biology
Ghent University
Fiers-Schell-Van Mantagu Building
Technologiepark 927
B-9052 Zwijnaarde The International Depository Authority:

Belgian Coordinated Collections of Microorganisms (BCCM™)
Laboratorium voor Moleculaire Biologie-Plasmidencollectie (LMBP)
Universiteit Gent
Technologiepark 927
B-9052 Gent-Zwijnaarde, Belgium Both Plasmid Deposits were all Made on Oct. 19, 2007.

$^{Ps}p_1 90$
*E. coli* HMS174(DE3)/pEGT1/AL-ORF1-90 kDa
BCCM accession No. ILMBP 5690

$^{Ps}p_2 90$
*E. coli* HMS174(DE3)/pEGT1/AL-ORF2-90 kDa
BCCM accession No. LMBP 5691

The present invention also provides vaccines against SRS that further comprise and/or encode one or more additional *P. salmonis* antigens. Such additional antigens include those described by US Published Patent Application No. US20070207165 (A1) and those described by WO2006037383(A1), the contents of both of which are hereby incorporated by reference in their entireties. These antigens include isolated *P. salmonis* $^{Ps}p45$ protein comprising the amino acid sequence of SEQ ID NO: 7 (complete $^{Ps}p45$ protein) or SEQ ID NO: 8 ($^{Ps}p45$ protein without the signal sequence) and antigenic fragments thereof.

Additional antigens described by US20070207165 (A1) and WO2006037383(A1), see also Table 14 below, include those comprising the amino acid sequence of SEQ ID NO: 9 (which shows homology with a protein family coding for AMP-binding enzymes), SEQ ID NO: 10 (which shows no homology to any protein family), SEQ ID NO: 11 (which shows no homology to any protein family), SEQ ID NO: 12 (which shows homology to the DDE endonuclease family and in particular to the integrase core domain), SEQ ID NO: 13 (which shows homology to transposases), SEQ ID NO: 14 (which shows some homology to the HlyD family of secretory proteins), and/or SEQ ID NO: 15 (which shows homology to the intergral membrane AcrB/AcrD/AcrB protein family). These antigens can be expressed e.g., by nucleic acids that encode one or more of these amino acid sequences.

As indicated above, $^{Ps}p45$ protein can be produced by recombinant *Yersinia ruckeri* cells deposited with the Belgian Coordinated Collections of Microorganisms ("BCCM") located at:

BCCM Laboratorium voor Microbiologie—Bacteriënverzameling (LMG) Universiteit Gent, K. L. Ledeganckstraat 35, B-9000 Gent, Belgium Strain Name: *Yersinia ruckeri* 224/pGEM5ZF+/45 kDa/S
BCCM accession No. LMG P-22044, deposited on Sep. 11, 2003.

Strain Name: *Yersinia ruckeri* 224/pGEM5ZF+/75 kDa
BCCM accession No. LMG P-22511, deposited on May 27, 2004.

The present invention also provides combination vaccines against SRS and IPN(SRS/IPN vaccines) that comprise one or more inventive *P. salmonis* 90 kDa antigens (e.g., $^{Ps}p_1 90$ and/or $^{Ps}p_2 90$) optionally in combination with any of the $^{Ps}p45$ proteins or SRS antigens noted above, in combination with one or more antigens obtained from an Infectious Pancreatic Necrosis (IPN) virus. These recombinant proteins (IPN antigens) are preferably expressed by transformed yeast, *Pichia pastoris*.

In one such embodiment, the antigen obtained from the IPN virus is the VP2 var protein or an antigenic fragment thereof. In a particular embodiment, the antigen is the VP2 var protein obtained from the transformed *Pichia pastoris* cell, BCCM Accession No. IHEM 20069 and/or from the transformed *Pichia pastoris* cell, BCCM Accession No. IHEM 20070. In another embodiment, the antigen obtained from the IPN virus is the VP3 protein or an antigenic fragment thereof. In a particular embodiment of this type, the antigen is the VP3 protein obtained from the transformed *Pichia pastoris* cell, BCCM Accession No. IHEM 20071 and/or from the transformed *Pichia pastoris* cell BCCM Accession No. IHEM 20072. In one embodiment of the present invention, the inventive SRS/IPN vaccine comprises at least one VP2var antigen and one VP3 antigen.

Four recombinant *Pichia pastoris* yeast cells were deposited with the following depository:

BCCM
Institut Scieritifique de la Santé Publique—Louis Pasteur (IHEM)
Section mycologie J. Wytsmanstraat 14 Rue J. Wytsman
B-1050 Brussels, Belgium These deposits were all made on Sep. 11, 2003.

Strain name: *Pichia pastoris* GS115/pPICZaB/VP2var/MUT+46
BCCM Accession No. IHEM 20069

Strain name: *Pichia pastoris* SMD1168/pPICZaB/VP2 367.5
BCCM Accession No. IHEM 20070

Strain name: *Pichia pastoris* KM71/pPICZaB/VP3/MUTs 30:11
BCCM Accession No. IHEM 20071

Strain name: *Pichia pastoris* GS115/pPICZaB/VP3 112.15
BCCM Accession No. IHEM 20072

As used herein the following terms shall have the definitions set out below:

As used herein the term "$^{Ps}p_1 90$" is used interchangably with the term "ORF1" and denotes a specific *Piscirickettsia salmonis* protein that is about 90 kDa in molecular weight. In a particular embodiment, $^{Ps}p_1 90$ comprises the amino acid sequence of SEQ ID NO: 2, which is encoded by the *P. salmonis* nucleotide sequence SEQ ID NO: 1 and the nucleotide sequence SEQ ID NO: 5, which was optimized for *E. coli* codon usage.

$^{Ps}p_1 90$ is encoded by an EGT1 plasmid deposited with the BCCM™/LMBP Collection having ascension number LMP 5690.

As used herein the term "$^{Ps}p_2 90$" is used interchangably with the term "ORF2" and denotes a specific *Piscirickettsia salmonis* protein that is about 90 kDa in molecular weight. In a particular embodiment, $^{Ps}p_2 90$ comprises the amino acid sequence of SEQ ID NO: 4, which is encoded by the *P. salmonis* nucleotide sequence SEQ ID NO: 3 and the nucleotide sequence SEQ ID NO: 6, which was optimized for *E. coli* codon usage.

$^{Ps}p_2 90$ is encoded by an EGT1 plasmid deposited with the BCCM™/LMBP Collection having ascension number LMP 5691.

As used herein the term "polypeptide" is used interchangeably with the term "protein" and is further meant to encompass peptides. Therefore, as used herein, a polypeptide is a polymer of two or more amino acids joined together by peptide linkages. Preferably, a polypeptide is a polymer comprising twenty or more amino acid residues joined together by peptide linkages, whereas a peptide comprises two to twenty amino acid residues joined together by peptide linkages.

As used herein a polypeptide "consisting essentially of" or that "consists essentially of" a specified amino acid sequence is a polypeptide that (i) retains an important characteristic of the polypeptide comprising that amino acid sequence, e.g., the antigenicity of at least one epitope of the inventive 90 kDa protein(s), and (ii) further comprises the identical amino acid sequence(s), except it consists of plus or minus 10% (or a lower percentage), and preferably plus or minus 5% (or a lower percentage) of the amino acid residues. In a particular embodiment, additional amino acid residues included as part of the polypeptide are part of a linked Tag, such as a C-terminal $His_6$ Tag.

A molecule is "antigenic" when it is capable of specifically interacting with an antigen recognition molecule of the immune system, such as an immunoglobulin (antibody) or T cell antigen receptor. An antigenic polypeptide (and/or fragment of the polypeptide) contains at least 6, and preferably at least 12 or more amino acid residues. An antigenic portion of a molecule can be that portion that is immunodominant for recognition by an antibody or a T cell receptor, and/or it can be a portion used to generate an antibody to the molecule by conjugating an immunogenic portion of the antigen to a carrier molecule for immunization. A molecule that is antigenic need not be itself immunogenic, i.e., capable of eliciting an immune response without a carrier.

As used herein the term "antigenic fragment" of a particular protein is a fragment of that protein that is antigenic. For example, an antigenic fragment of a $^{Ps}p_1 90$ protein or a $^{Ps}p_2 90$ protein can be any antigenic fragment of the $^{Ps}p_1 90$ protein or $^{Ps}p_2 90$ protein respectively, including large fragments that are missing as little as a single amino acid from the full-length protein. In a particular embodiment, an antigenic fragment of the $^{Ps}p_1 90$ protein or a $^{Ps}p_2 90$ protein contains between 12 and 800 amino acid residues. In another embodiment, an antigenic fragment of the $^{Ps}p_1 90$ protein or a $^{Ps}p_2 90$ protein contains between 25 and 250 amino acid residues. In yet another embodiment, an antigenic fragment of a $^{Ps}p_1 90$ protein or a $^{Ps}p_2 90$ protein contains 100 amino acid residues or more, but fewer than 600 amino acid residues. In still another embodiment, an antigenic fragment of a $^{Ps}p_1 90$ protein or a $^{Ps}p_2 90$ protein contains 250 amino acid residues or more, but fewer than 600 amino acid residues. In yet another embodiment, an antigenic fragment of a $^{Ps}p_1 90$ protein or a $^{Ps}p_2 90$ protein contains 400 amino acid residues or more, but fewer than 600 amino acid residues.

An antigenic fragment of a given $^{Ps}p_1 90$ protein or a $^{Ps}p_2 90$ protein can be obtained from a recombinant source, from a protein isolated from natural sources, or through chemical synthesis. Similarly, an antigenic fragment can be obtained following the proteolytic digestion of such $^{Ps}p_1 90$ proteins, $^{Ps}p_2 90$ proteins or fragments of either. Alternatively, an antigenic fragment of the present invention can be generated by recombinant expression, or alternatively, through peptide synthesis.

As used herein, a multivalent vaccine is a vaccine that comprises two or more different antigens. In a particular embodiment of this type, the multivalent vaccine stimulates the immune system of the recipient against two or more different pathogens. Specific multivalent vaccines are exemplified below.

As used herein the term "chimeric protein" is used interchangeably with the terms "chimeric polypeptide" and "chimeric peptide" and is meant to include fusion proteins, polypeptides, and peptides. A "chimeric protein" comprising a $^{Ps}p_1 90$ and/or $^{Ps}p_2 90$ protein of the present invention comprises at least a portion of a particular protein (e.g., $^{Ps}p_1 90$) joined via a peptide bond to at least a portion of a different protein (e.g., a non-$^{Ps}p_1 90$ protein). A chimeric protein of the present invention also can comprise two or more different proteins and/or portions thereof, including a chimeric $^{Ps}p_1 90$-$^{Ps}p_2 90$ protein. Chimeric proteins of the present invention also can have additional structural, regulatory, and/or catalytic properties. As used herein a chimeric protein can contain multiple additions to at least a portion of a given protein, e.g., a chimeric protein can comprise both a $His_6$Tag and an alternative signal sequence. In a particular embodiment, a non-$^{Ps}p_1 90$ (or non-$^{Ps}p_2 90$) portion of the chimeric protein functions as a means of detecting and/or isolating the chimeric protein or fragment thereof after a recombinant nucleotide encoding the given protein or antigenic fragment thereof is expressed. Non-$^{Ps}p_1 90$ (or non-$^{Ps}p_2 90$) protein amino acid sequences are generally, but not always, either amino- or carboxy-terminal to the protein sequence.

As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

As used herein, DNA and protein sequence percent identity can be determined using C, MacVector (MacVector, Inc. Cary, N.C. 27519), Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

As used herein a "nucleic acid" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. When referring to a nucleic acid that is double stranded both the "sense" strand and the complementary "antisense" strand are intended to be included. Thus a nucleic acid that is hybridizable to SEQ ID NOs: 1 or 3, for example, can be either hybridizable to the "sense" strand of the respective sequence, or to the "antisense" strand which can be readily determined from the respective sense strands listed in the Sequence Listing provided herein. The individual components of a nucleic acid are referred to as nucleotides.

A DNA "coding sequence" is a double-stranded DNA sequence that is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A nucleotide coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which can then be trans-RNA spliced, if, when, and where appropriate, and translated into the protein encoded by the coding sequence.

A nucleotide sequence is "operatively linked" to an expression control sequence when the expression control sequence controls or regulates the transcription and translation of that nucleotide sequence. The term operatively linked includes having an appropriate start signal.

A "heterologous nucleotide sequence" as used herein is a nucleotide sequence that is added by recombinant methods to a nucleotide sequence encoding a polypeptide of the present invention or encoding a fragment thereof (i.e., an antigenic fragment), to form a nucleic acid that is not naturally formed in nature. Such nucleic acids can e.g., encode chimeric proteins. In addition, as used herein, a heterologous nucleotide sequence need not be a single contiguous nucleotide sequence, but can include multiple non-contiguous nucleotide sequences that have been combined with a nucleotide sequence encoding a polypeptide of the present invention, or a portion thereof. A heterologous nucleotide sequence can comprise non-coding sequences including restriction sites, regulatory sites, promoters and the like. In still another embodiment the heterologous nucleotide can function as a means of detecting a nucleic acid of the present invention.

The present invention provides heterologous nucleotide sequences that when combined with nucleotide sequences encoding a polypeptide of the invention or a fragment thereof, are necessary and sufficient to encode all of the chimeric proteins of the present invention. In a particular embodiment, the polypeptide comprises the amino acid sequence of SEQ ID NO: 2.

As used herein, a bacterium is said to be "recombinant" when the nucleotide sequence of the DNA that it naturally contains has been purposely altered by at least one nucleotide addition, deletion, and/or modification through genetic engineering. A recombinant bacterin is an inactivated or killed recombinant bacterium.

The phrase "binding to" or "binds to" in regard to a ligand binding to a polypeptide (e.g., antigen to an antibody) is used herein to include any or all such specific interactions that lead to a protein-ligand binding complex. This can include processes such as covalent, ionic (electrostatic and/or charged), hydrophobic and hydrogen bonding, but does not include non-specific associations such as solvent preferences.

As used herein a "small organic molecule" is an organic compound [or organic compound complexed with an inorganic compound (e.g., metal)] that has a molecular weight of less than 3 kDa.

As used herein the terms "approximately" and "about" are used to signify that a value is within twenty percent of the indicated value i.e., an amino acid sequence containing "approximately" 400 amino acid residues can contain between 320 and 480 amino acid residues.

As used herein the unit "° days" denotes the number of days of incubation following the vaccination of a fish, multiplied by the average temperature in ° C. for that incubation.

Nucleic Acids Encoding the Polypeptides of the Present Invention

A nucleic acid, such as a cDNA, that encodes a polypeptide of the present invention, can be placed into a vector, e.g., a recombinant bacterial host cell, to express a protein and/or antigen of the present invention, e.g., the $^{Ps}p_1 90$ and $^{Ps}p_2 90$ proteins. Such recombinant host cells can be inactivated, e.g., disrupted and converted to bacterins, and used in immunogenic compositions such as vaccines.

In addition, obtaining and/or constructing a DNA that encodes one of the polypeptides of the present invention, including those encoding $^{Ps}p_1 90$ and/or $^{Ps}p_2 90$, or antigenic fragments thereof, facilitates the production of economically important quantities of the protein or antigenic fragments thereof. The large quantities of the proteins and/or antigenic fragments thereof produced are useful for making certain vaccines of the present invention.

Accordingly, the present invention provides specific nucleotide constructs that allow for the expression and isolation of large quantities of the proteins and/or antigens of the present invention, such as the $^{Ps}p_1 90$ and/or $^{Ps}p_2 90$ proteins. These nucleic acids can further contain heterologous nucleotide sequences. To express a recombinant protein of the present invention in a host cell, an expression vector can be constructed comprising the corresponding cDNA. The present invention therefore, provides expression vectors containing nucleic acids encoding the proteins of the present invention, including variants thereof.

Due to the degeneracy of nucleotide coding sequences, other DNA sequences which encode substantially the same amino acid sequence as a nucleic acid encoding a polypeptide of the present invention may be used in the practice of the present invention. These include, but are not limited to, allelic genes, homologous genes from other strains, and/or those that are altered by the substitution of different codons that encode the same amino acid residue within the sequence, thus producing a silent change. Host cells comprising the expression vectors of the present invention are also provided. One particular host cell is an *E. coli* cell.

General methods for the cloning of cDNAs and expression of their corresponding recombinant proteins have been described [see Sambrook and Russell, *Molecular Cloning, A laboratory Manual,* 3$^{rd}$ edition, Cold Spring Harbor Laboratory Press, Cold Spring Harbor L.I. (2000)]. The particular methodology used herein is described in the Examples below. Preferably, all of the nucleic acid constructs of the present invention are sequence confirmed.

In addition, any technique for mutagenesis known in the art can be used to modify a native $^{Ps}p_1 90$ or $^{Ps}p_2 90$ protein of the present invention, including but not limited to, in vitro site-directed mutagenesis [Hutchinson et al., *J. Biol. Chem.,* 253: 6551 (1978); Zoller and Smith, *DNA,* 3:479-488 (1984); Oliphant et al., *Gene,* 44:177 (1986); Hutchinson et al., *Proc. Natl. Acad. Sci. U.S.A.,* 83:710 (1986); Wang and Malcolm, *BioTechniques* 26:680-682 (1999) the contents of which are hereby incorporated by reference in their entireties]. The use of TAB@ linkers (Pharmacia), etc. and PCR techniques also can be employed for site directed mutagenesis [see Higuchi, "Using PCR to Engineer DNA", in PCR Technology: Principles and Applications for DNA Amplification, H. Erlich, ed., Stockton Press, Chapter 6, pp. 61-70 (1989)].

The present invention also provides nucleic acids that hybridize to nucleic acids comprising the nucleotide sequences of the present invention. A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength [see Sambrook and Russell, *Molecular Cloning, A laboratory Manual,* 3$^{rd}$ edition, Cold Spring Harbor Laboratory Press, Cold Spring Harbor L.I. (2000)].

The conditions of temperature and ionic strength determine the "stringency" of the hybridization. For preliminary screening for homologous nucleotides, low stringency hybridization conditions, corresponding to a $T_m$ of 55° C., can be used, e.g., 5× saline sodium citrate (SSC), 0.1% sodium dodecyl sulfate (SDS), 0.25% milk, and no formamide; or 30% formamide, 5×SSC, 0.5% SDS. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleotides having those sequences. The relative stability (corresponding to higher $T_m$) of nucleotide hybridizations decreases in the following order: RNA:RNA, DNA:RNA, DNA:DNA. For hybrids of greater than 100 nucleotides in length, equations for calculating $T_m$ have been derived [see Sambrook and Russell, *Molecular Cloning, A laboratory Manual,* 3$^{rd}$ edition, Cold Spring Harbor Laboratory Press, Cold Spring Harbor L.I. (2000)]. For hybridization with shorter nucleic acids, i.e., oligonucleotides, the position of mismatches becomes more important, and the length of the oligonucleotide determines its specificity.

Depending upon circumstances a suitable minimal length for a hybridizable nucleic acid can be at least about 12 nucleotides; or at least about 18 nucleotides; or the length can be at least about 24 nucleotides; or at least about 36 nucleotides. Alternatively, the minimum length can be at least about 48 or at least about 72 nucleotides, or longer, as indicated above. In a specific embodiment, the term "standard hybridization conditions" refers to a $T_m$ of 55° C., and utilizes conditions as set forth above. Under more stringent conditions, the $T_m$ is 60° C., and under even more stringent conditions, the $T_m$ is 65° C. for both hybridization and wash conditions, respectively.

Polypeptides of the Present Invention

The present invention provides isolated and/or recombinant *Piscirickettsia salmonis* polypeptides, including all of the antigens of the present invention, e.g., the $^{Ps}p_1$ 90 and/or $^{Ps}p_2$ 90 proteins (plus or minus an amino-terminal signal peptide), *P. salmonis* strain variants thereof, antigenic fragments thereof, and chimeric proteins thereof. In addition, polypeptides containing altered sequences in which functionally equivalent amino acid residues are substituted for those within the wild type amino acid sequence resulting in a conservative amino acid substitution, are also provided by the present invention.

For example, one or more of these amino acid residues within the sequence can be substituted by another amino acid of a similar polarity, which acts as a functional equivalent, resulting in a silent alteration. Substitutes for an amino acid within the sequence may be selected from other members of the class to which the amino acid belongs.

For example, the nonpolar amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine and lysine. The negatively charged (acidic) amino acids include aspartic acid and glutamic acid.

Particularly preferred conserved amino acid exchanges are:

(a) Lys for Arg or vice versa such that a positive charge may be maintained;

(b) Glu for Asp or vice versa such that a negative charge may be maintained;

(c) Ser for Thr or vice versa such that a free —OH can be maintained;

(d) Gln for Asn or vice versa such that a free $NH_2$ can be maintained; and (e) Ile for Leu or for Val or vice versa as being roughly equivalent hydrophobic amino acids.

All of the polypeptides of the present invention, including antigenic fragments, also can be part of a chimeric protein. In a specific embodiment, a chimeric polypeptide is expressed in a prokaryotic cell. Such a chimeric protein can be a fusion protein used to isolate a polypeptide of the present invention, through the use of an affinity column that is specific for a protein fused to the $^{Ps}p_1 90$ and/or $^{Ps}p_2 90$ proteins, for example. Examples of such fusion proteins include: a glutathione-S-transferase (GST) fusion protein, a maltose-binding protein (MBP) fusion protein, a FLAG-tagged fusion protein, or a poly-histidine-tagged fusion protein. Specific linker sequences such as a Ser-Gly linker can also be part of such a fusion protein.

Indeed, the expression of one or more of the inventive proteins, as a fusion protein, can facilitate stable expression, and/or allow for purification based on the properties of the fusion partner. Thus the purification of the recombinant polypeptides of the present invention can be simplified through the use of fusion proteins having affinity Tags. For example, GST binds glutathione conjugated to a solid support matrix, MBP binds to a maltose matrix, and poly-histidine chelates to a Ni-chelation support matrix [see Hochuli et al., *Biotechnology* 6:1321-1325 (1998)].

The fusion protein can be eluted from the specific matrix with appropriate buffers, or by treating with a protease that is specific for a cleavage site that has been genetically engineered in between a $^{Ps}p_1 90$ and/or $^{Ps}p_2 90$ protein, for example, and its fusion partner. Alternatively, a $^{Ps}p_1 90$ and/or $^{Ps}p_2 90$ protein can be combined with a marker protein such as green fluorescent protein [Waldo et al., *Nature Biotech.* 17:691-695 (1999); U.S. Pat. No. 5,625,048 and WO 97/26333, the contents of which are hereby incorporated by reference in their entireties].

Alternatively or in addition, other column chromatography steps (e.g., gel filtration, ion exchange, affinity chromatography etc.) can be used to purify the recombinant polypeptides of the present invention (see below). In many cases, such column chromatography steps employ high performance liquid chromatography or analogous methods in place of the more classical gravity-based procedures.

In addition, the polypeptides of the present invention, including the $^{Ps}p_1 90$ and/or $^{Ps}p_2 90$ proteins, and antigenic fragments thereof, can be chemically synthesized [see e.g., Synthetic Peptides: *A User's Guide*, W.H. Freeman & Co., New York, N.Y., pp. 382, Grant, ed. (1992)].

General Polypeptide Purification Procedures

Generally, initial steps for purifying a polypeptide of the present invention can include salting in or salting out, in ammonium sulfate fractionations; solvent exclusion fractionations, e.g., an ethanol precipitation; detergent extractions to free membrane bound polypeptides, using such detergents as TRITON X-100, TWEEN-20 etc.; or high salt extractions. Solubilization of membrane proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel, hydroxyapatite, or solid phase binding. Solid phase binding may be performed through ionic bonding, with either an anion exchanger, such as diethylaminoethyl (DEAE), or diethyl [2-hydroxypropyl]aminoethyl (QAE) SEPHADEX or cellulose; or with a cation exchanger such as carboxymethyl (CM) or sulfopropyl (SP) SEPHADEX or cellulose. Alternative means of solid phase binding includes the exploitation of hydrophobic interactions e.g., the use of a solid support such as phenylSepharose and a high salt buffer; affinity-binding immuno-binding, using e.g., a inventive protein bound to a suitable anti-$^{Ps}p_1 90$ and/or anti-$^{Ps}p_2 90$ selective antibody, respectfully, bound to an activated support. Other solid phase supports include those that contain specific dyes or lectins etc.

A further solid phase support technique that is often used at the end of the purification procedure relies on size exclusion, such as SEPHADEX and SEPHAROSE gels. Alternatively, a pressurized or centrifugal membrane technique, using size exclusion membrane filters may be employed. Oftentimes, these two methodologies are used in tandem.

Solid phase support separations are generally performed batch-wise with low-speed centrifugation, or by column chromatography. High performance liquid chromatography (HPLC), including such related techniques as FPLC, is presently the most common means of performing liquid chromatography. Size exclusion techniques may also be accomplished with the aid of low speed centrifugation. In addition size permeation techniques such as gel electrophoretic techniques may be employed. These techniques are generally performed in tubes, slabs or by capillary electrophoresis.

Almost all steps involving polypeptide purification employ a buffered solution. Unless otherwise specified, generally 25-100 mM concentrations of buffer salts are used. Low concentration buffers generally imply 5-25 mM concentrations. High concentration buffers generally imply concentrations of the buffering agent of between 0.1-2.0 M concentrations. Typical buffers can be purchased from most biochemical catalogues and include the classical buffers such as Tris, pyrophosphate, monophosphate and diphosphate and the Good buffers such as Mes, Hepes, Mops, Tricine and Ches [Good et al., *Biochemistry,* 5:467 (1966); Good and Izawa, *Meth. Enzymol.,* 24B:53 (1972); and Fergunson and Good, *Anal. Biochem.,* 104:300 (1980].

Materials to perform all of these techniques are available from a variety of commercial sources such as Sigma Chemical Company in St. Louis, Mo.

Antibodies to the Polypeptides of the Present Invention

The polypeptides of the present invention, and antigenic fragments thereof, as produced by a recombinant source, or through chemical synthesis, or as isolated from natural sources; and variants, derivatives or analogs thereof, including fusion proteins, may be used as an immunogen to generate antibodies. Such antibodies include but are not limited to polyclonal, monoclonal, chimeric including single chain, Fab fragments, and a Fab expression library. Such antibodies can be used in diagnostic kits or as components in vaccines.

Specific anti-$^{Ps}p_1 90$ and/or $^{Ps}p_2 90$ protein antibodies of the invention, for example, may be cross-reactive, that is, they may recognize one specific 90 kDa protein, e.g., $^{Ps}p_1 90$, or a closely related protein obtained from a different source (e.g., a *Piscirickettsia*-like bacterium). Polyclonal antibodies have greater likelihood of cross-reactivity. Alternatively, an antibody of the invention may be specific for a single form of an inventive protein, for example, such as a specific fragment of $^{Ps}p_1 90$ that has the amino acid sequence of SEQ ID NO: 2, or a closely related variant thereof.

In a particular aspect of the present invention compositions and uses of antibodies that are immunoreactive with a $^{Ps}p_1 90$ and/or $^{Ps}p_2 90$ protein are provided. Such antibodies "bind specifically" to the particular $^{Ps}p_1 90$ and/or $^{Ps}p_2 90$ protein respectively, meaning that they bind via antigen-binding sites of the antibody as compared to non-specific binding interactions.

The terms "antibody" and "antibodies" are used herein in their broadest sense, and include, without limitation, intact monoclonal and polyclonal antibodies as well as fragments such as Fv, Fab, and F(ab') fragments, single-chain antibodies such as scFv, and various chain combinations. The antibodies may be prepared using a variety of well-known methods including, without limitation, immunization of animals having native or transgenic immune repertoires, phage display, hybridoma and recombinant cell culture.

Both polyclonal and monoclonal antibodies may be prepared by conventional techniques. [See, for example, *Monoclonal Antibodies, Hybridomas: A New Dimension in Biological Analyses*, Kennet et al. (eds.), Plenum Press, New York 37 (1980); and *Antibodies: A Laboratory Manual*, Harlow and Land (eds.), Cold Spring Harbor Laboratory Press, Cold Spring Harbor, N.Y., (1988)].

Various procedures known in the art may be used for the production of polyclonal antibodies to a particular $^{Ps}p_1 90$ and/or $^{Ps}p_2 90$ protein, variants or derivatives or analogs thereof. For the production of an antibody, various host animals can be immunized by injection with the $^{Ps}p_1 90$ and/or $^{Ps}p_2 90$ protein, variant or a derivative (e.g., or fusion protein) thereof or fragment thereof, including but not limited to rabbits, mice, rats, sheep, goats, etc. In one embodiment, the inventive protein can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, and dinitrophenol.

For preparation of monoclonal antibodies directed toward a given inventive protein, variant, or analog, or derivative thereof, any technique that provides for the production of antibody molecules by continuous cell lines in culture may be used. These include but are not limited to the hybridoma technique originally developed by Kohler and Milstein [*Nature,* 256:495-497 (1975)], as well as the trioma technique, and the human B cell hybridoma technique [Kozbor et al., *Immunology Today,* 4:72 (1983); Cote et al., *Proc. Natl. Acad. Sci. U.S.A.,* 80:2026-2030 (1983)].

The monoclonal antibodies of the present invention include chimeric antibodies versions of antibodies originally produced in mice or other non-human animals. Techniques developed for the production of "chimeric antibodies" by splicing the genes from a mouse antibody molecule specific for a given inventive protein, for example, together with genes from a fish antibody of appropriate biological activity (e.g., a salmon) can be used. Such chimeric antibodies are within the scope of this invention [see in general, Morrison et al., *J Bacteriol,* 159:870 (1984); Neuberger et al., *Nature,* 312:604-608 (1984); Takeda et al., *Nature,* 314:452-454 (1985)].

Hybridoma cell lines that produce monoclonal antibodies specific for the polypeptides of the present invention are also provided by the present invention. Such hybridomas may be produced and identified by conventional techniques.

One method for producing such a hybridoma cell line comprises immunizing an animal with a polypeptide, harvesting spleen cells from the immunized animal, fusing the spleen cells to a myeloma cell line, thereby generating hybridoma cells, and identifying a hybridoma cell line that produces a monoclonal antibody that binds the polypeptide. The monoclonal antibodies produced by hybridomas may be recovered by conventional techniques.

According to the invention, techniques described for the production of single chain antibodies [U.S. Pat. Nos. 5,476,786, 5,132,405, and 4,946,778, the contents of which are hereby incorporated by reference in their entireties] can be adapted to produce *p. salmonis* protein-specific single chain antibodies, e.g., $^{Ps}p_2 90$ protein-specific single chain antibodies. An additional embodiment of the invention utilizes the techniques described for the construction of Fab expression libraries [Huse et al., *Science,* 246:1275-1281 (1989)] to allow rapid and easy identification of monoclonal Fab fragments with the desired specificity for $^{Ps}p_1 90$ and/or $^{Ps}p_2 90$ protein, variant, derivative, and/or analog.

Antibody fragments which contain the idiotype of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by such techniques as radioimmunoassay, enzyme-linked immunosorbant assay (ELISA), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays.

In one embodiment, antibody binding is detected by detecting a label, e.g., a fluorescent label such as fluorescene isothiocyanate (FITC), on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular inventive protein, one may assay the hybridomas generated for a product which binds to a protein fragment containing such an epitope and choose those which do not cross-react with a modified inventive protein that does not contain that epitope. One can select an antibody specific to ${}^{Ps}p_1 90$ and/or ${}^{Ps}p_2$ 90 from a particular source based on the positive specific binding with that specific protein.

SRS Vaccines

The present invention provides SRS vaccines. One particular embodiment is a non-mineral oil injection prime vaccine comprising one or more antigens from *Piscirickettsia salmonis*, as disclosed below. In one embodiment of this type, inactivated recombinant bacteria (bacterins) comprise one or more of the *Piscirickettsia salmonis* antigens of the present invention. The present invention also provides SRS vaccines that are designed to protect against one or more other fish pathogens. For example, furunculosis is an infectious ulcerative disease of salmon and trout caused by the bacterium *Aeromonas salmonicida*. In a particular embodiment, the vaccine will comprise in addition to the *Piscirickettsia salmonis* component(s), two Infectious pancreatic necrosis (IPN) antigens as discussed herein, *A. salmonicida* as discussed below, *Vibrio ordalii*, Infectious Salmon Anemia, and/or Salmon Pancreatic Disease.

Other fish pathogens include, but are not limited to:

| PATHOGEN (antigen) | RELATED DISEASE |
|---|---|
| IPN virus | Infectious pancreatic necrosis |
| *Vibrio anguillarum* or *Vibrio ordalii* | Vibrosis |
| *Vibrio salmonicida* | Cold water Vibriosis (Hitra disease) |
| *Moritella viscosus* | Winter sores disease |
| *Photobacterium damsela* (subspecies *Piscicida*) | Pasteurellosis |
| *Lactococcus garviae* | Streptococcosis |
| *Streptococcus iniae* | |
| *Moritella viscosus* | Winter Sores |
| *Noccardia kampachi* | |
| *Renibacterium salmoninarum* | |
| ISA Virus | Infectious Salmon Anemia |
| IHN Virus | Infectious Heamorhagic Necrosis |
| SPD Virus | Salmon pancreatic disease |
| SD Virus | Sleeping disease |

The vaccines for these various diseases can be prepared from whole cells, bacterins, killed and/or attenuated virus, protein extracts, recombinant DNA vaccine vectors, isolated antigens, recombinant antigens and mixtures thereof. Under particular circumstances, as for *Photobacterium damsela* and *Aeromonas salmonicida*, the vaccines are preferably prepared from two separate cultures grown under iron-depleted conditions and iron-supplemented conditions, respectively.

In a particular embodiment, a vaccine comprises the ${}^{Ps}p_1 90$ and/or ${}^{Ps}p_2 90$ protein(s) from *Piscirickettsia salmonis*. In another embodiment, a vaccine comprises the ${}^{Ps}p_1 90$ and/or ${}^{Ps}p_2 90$ protein(s) in combination with one or more of the above-noted other antigens from *Piscirickettsia salmonis* (e.g., the ${}^{Ps}45$ protein). In another embodiment, a vaccine comprises the ${}^{Ps}p_1 90$ and/or ${}^{Ps}p_2 90$ protein(s), optionally in combination with IPN proteins, and optionally further in combination with one or more other antigens from *Piscirickettsia salmonis*. In still another embodiment, the vaccine comprises the ${}^{Ps}p_1 90$ and/or ${}^{Ps}p_2 90$ protein(s) and/or one or more other antigens from *Piscirickettsia salmonis*, one or more IPN proteins, and one or more antigens to control *Aeromonas salmonicida*. In a particular embodiment of this type, *Aeromonas salmonicida* antigens are two types of whole bacteria grown on bacterial growth media and killed by the addition of formalin.

For an SRS vaccine according to the invention, *Escherichia coli* was selected as the best candidate for hosting and expressing the ${}^{Ps}p_1 90$ and/or ${}^{Ps}p_2 90$ protein(s) of the present invention.

Two IPN viral antigens are exemplified below (see also WO 02/38770, the contents of which are hereby incorporated in its entireties). One of which is derived from Vp2, which is the major outer capsid protein and the other from Vp3, which is an internal protein of the IPN virus. The molecular weight of the Vp2 protein is 52 kDa, whereas that of the Vp3 protein is 30 kDa. The IPN proteins of the vaccines of the present invention are preferably purified recombinant proteins. In the Example 6 below, the IPN proteins are expressed and excreted by transformed yeast (*Pichia pastoris*) and then optionally purified from these yeast cells.

Antigens for a vaccine that also protects against furunculosis can be obtained from whole killed bacteria *Aeromonas salmonicida* (e.g., formalin-killed). Early *A. salmonicida* vaccines contain whole *A. salmonicida* bacteria grown in normal growth medium and then inactivated by the addition of formalin. These bacterins contain a mixture of antigens including the surface A-layer, inactivated proteases and lipopoly-saccharide. On the other hand when *A. salmonicida* are grown in normal medium in the total absence of iron, a group of new antigens are expressed. These new antigens are termed iron-regulated outer membrane proteins (IROMPs). IROMPS are highly immunogenic and they provide enhanced protection relative to vaccines containing inactivated *A. salmonicida* grown in normal medium. Four IROMP proteins having molecular weights of 82 kDa, 77 kDa, 72 kDa and 70 kDa respectively have been identified.

The primary and secondary antibody responses to IROMP antigens in Atlantic salmon (*Salmo sala*, immunized with A+ (iron plus) and A− (iron minus) *Aeromonas salmonicida* bacterins have been reported [O'Dowd et al., *Fish & Shellfish Immunology* 9:125-138 (1999)]. Thus particular vaccines of the present invention contain one strain of *A. salmonicida* (MT004) grown under conditions of iron-limitation and one strain of *A. salmonicida* (MT423) grown under condition of iron-supplementation.

The *Vibrio anguillarum* (serotype 01) and *V. anguillarum* (serotype $O_2$) are different serotypes that are not cross-protective and therefore, for broad spectrum protection both antigens are can be included in the vaccine. Alternatively, or in combination, *Vibrio ordalii* can be employed.

Administration

The vaccines of the present invention may be administered to fish by any of a number of means including by injection (e.g., intramuscularly, or intraperitoneally), immersion, and/or through a delivery system for oral vaccination. Vaccinating fish by injection can be performed either with an adjuvant to increase the activity of the antigens, or without an adjuvant.

Adjuvants include aqueous adjuvants, such as Alhydrogel or aluminum hydroxide, and oil adjuvants.

Mineral oil adjuvants are commonly employed in fish vaccines and are included in the present invention. One such adjuvant is mannide oleate in a mineral oil solution. In a particular embodiment of this type, the vaccine comprises 70% mannide oleate in a mineral oil solution. Another mineral oil adjuvant of the present invention consists of white mineral oil, Span 80 [sorbitan monooleate], and Tween 80 [polyoxyethylene sorbitan monooleate]. In a particular embodiment, a vaccine comprises 80% of an adjuvant having the following formulation: 944 ml white mineral oil: 50.3 ml Span 80: 5.7 ml Tween 80.

Since mineral oil adjuvants generally cause damage to the fish at the site of injection (lesions, which have to be removed before sale) and they depress growth rates for a period of time, the present invention also provides non-mineral oil adjuvants. Synthetic non-mineral oil adjuvants include those commercially available from Seppic SA. Montanide, e.g., Montanide ISA563, Montanide ISA 575, Montanide ISA 711, and Montanide ISA 760. Montanide ISA 711 is essentially mannide oleate in an oil solution. Particular embodiments of a vaccine of the present invention comprise 50% of either Montanide ISA563, Montanide ISA 575, Montanide ISA 760 or 70% Montanide ISA 711.

Alternatively, vaccines can be applied by a long-term immersion bath. In one such embodiment, vaccination via an immersion bath is preceded by hyperosmotic treatment [see Huising et al., *Vaccine* 21:4178-4193 (2003)]. In another embodiment, a vaccine is administered by spraying the fish.

The present invention also includes orally-delivered vaccines. Generally, oral vaccines are prepared by either top-dressing the food with an antigen (e.g., by spray drying) or by incorporating the antigen in the food [see, e.g., Vinitnantharat et al., *Adv. Vet. Med.* 41:539-550 (1999)]. Other techniques include water-in-oil methods, bioencapsulation, microencapsulation incorporation into liposomes, incorporation in hollow feed prills, and incorporation into microparticle carriers, e.g., poly-lactide co-glycolide carrier particles [see, e.g., Singh et al., *Expert Opin. Biol. Ther.* 4(4):483-491 (2004)]. Yet another method entails expressing the antigen in algae.

Booster vaccines are also part of the present invention. In a particular embodiment, an oily emulsion oral booster vaccine comprising one or more antigens from *Piscirickettsia salmonis* is used after the primary vaccination. Preferably the oily emulsion is made up of water:oil in the range of 6:4 to 4:6. The level of free fatty acids should not be greater than 5% by weight of the oil and preferably no greater than 3%. Particular oils include whole fish body oil and neutral marine oil. The emulsifier is preferably food grade. Lecithin can be used as such an emulsifier, e.g., soya lecithin.

The emulsifier generally comprises from approximately 0.1% to approximately 5% by weight of the total emulsion. In a particular embodiment of this type, the oily phase of the emulsion is 47% v/v refined fish body oil plus 3% v/v lecithin (Bolec MT) which are mixed, sterilized with gamma irradiation and then blended, using an homogenizer. The aqueous antigen phase can be diluted with phosphate buffered saline [see, GB 2 255 909, PCT/GB9101828, WO/92/06599, the contents of which are hereby incorporated by reference in their entireties].

Injection vaccination is usually conducted on a commercial scale using a fixed dose automatic repeating syringe or an automatic injection vaccination machine. These methods are designed to deliver a fixed dose of usually 0.1 or 0.2 ml per fish. The vaccine is injected through the body wall into the intra-peritoneal cavity. It is also possible to immunize fish by injecting the vaccine into the dorsal sinus. Generally, fish are vaccinated by injection following anesthetization.

Immersion vaccination can be performed as follows: Dilute 1 liter of vaccine with 9 liters of clean hatchery water. Then Drain and weigh a netful of fish and dip fish in the diluted vaccine for 30 to 60 seconds ensuring that fish are totally immersed in the vaccine. After 30 to 60 seconds lift net, drain and return fish to holding tank. Repeat until 100 kg of fish have been dipped into 10 liters of diluted vaccine.

Oral vaccination can be performed as follows: A container of vaccine is brought to room temperature (20° C.) and then shaken prior to use. The vaccine is mixed with the fish feed so that the vaccine is coated onto the surface of the fish feed and adsorbed. The total vaccine dose should be fed over a 10 day period at 1/10 dose per fish per day.

Vaccination Recipients

Salmonid rickettsial septicemia (SRS) was first observed in salmonids, which are the fish in the Salmonidae family, of the order Salmoniformes and of the class Osteichthyes. Salmonids are elongate bony fish with the last three vertebrae upturned, having a small adipose fin without fin rays between the dorsal fin and the tail. Many species of salmonids live in the sea, but enter fresh water to spawn. The Salmonidae family includes salmon, trout, char, and whitefish (see Table 1, below, which provides a non-exhaustive list of fish in the Salmonidae family).

TABLE 1

| Salmonidae Family | |
|---|---|
| *Coregonus clupeaformis* | Lake whitefish |
| *Coregonus hoyi* | Bloater |
| *Oncorhynchus keta* | Chum salmon |
| *Oncorhynchus gorbuscha* | Pink salmon |
| *Oncorhynchus kisutch* | Coho salmon (silver salmon) |
| *Oncorhynchus masou* | cherry salmon (masou salmon) |
| *Oncorhynchus nerka* | Sockeye salmon |
| *Oncorhynchus tshawytscha* | King salmon (chinook salmon) |
| *Prosopium cylindraceum* | Round whitefish |
| *Oncorhynchus clarki* | Cutthroat trout |
| *Oncorhynchus mykiss* | Rainbow trout |
| *Salmo salar* | Atlantic salmon |
| *Salmo trutta* | Brown trout |
| *Salmo trutta* X *S. fontinalis* | Tiger hybrid-trout |
| *Salvelinus alpinus* | Arctic charr |
| *Salvelinus confluentus* | Bull trout |
| *Salvelinus fontinalis* | Brook trout |
| *Salvelinus leucomaenis* | Japanese charr (white spotted charr) |
| *Salvelinus malma* | Dolly varden (Miyabe charr) |
| *Salvelinus namaycush* | Lake trout |
| *Thymallus thymallus* | Grayling |

Reports of (SRS) and closely related Rickettsial syndrome afflicting fish as disparate as tilapia, white sea bass, rainbow trout, steelhead trout, grouper, Chilean sea bass, tiger puffers, red sea bream, blue-eyed plecostomus, striped bass, fluke, Atlantic cod, butter fish, ocean pout, spotted hake, summer and winter flounder, weakfish, yellowtail flounder, Windowpane flounder (*Scophthalmus aquosus*) cultured amberjack, three lined grunt, and blue eyed plecostomus indicates that the vaccines of the present invention may be used to vaccinate essentially any fish. Preferably the fish are in the Teleosti grouping of fish, i.e., teleosts. Both the Salmoniformes order (which includes the Salmonidae family) and the Perciformes order (which includes the Centrarchidae family) are contained within the Teleosti grouping.

Aside from the Salmonidae family and those included above, examples of potential vaccination recipients include the Serranidae family, the Sparidae family, the Cichlidae family, the Centrarchidae family, the three-Line Grunt (*Parapristipoma trilineatum*), and the Blue-Eyed *Plecostomus* (*Plecostomus* spp) of Tables 2 and 3, below.

TABLE 2

| TAXON NAME | COMMON NAME |
|---|---|
| Some Members of the Serranidae Family | |
| *Centropristis ocyurus* | Bank sea bass |
| *Centropristis philadelphicus* | Rock sea bass |
| *Centropristis striata* | Black sea bass |
| *Diplectrum bivittatum* | Dwarf sandperch |
| *Diplectrum formosum* | Sand perch |
| *Epinephelus flavolimbatus* | Yellowedge grouper |
| *Epinephelus morio* | Red grouper |
| *Serranus phoebe* | Tattler |
| *Serranus tortugarum* | Chalk bass |
| Some Members of the Sparidae family | |
| *Archosargus probatocephalus* | Sheepshead |
| *Archosargus rhomboidalis* | Sea bream |
| *Calamus penna* | Sheepshead porgy |
| *Lagodon rhomboides* | Pinfish |
| *Pagrus Major* | Red Sea bream |
| *Sparus aurata* | Gilthead Sea bream |
| *Stenotomus chrysops* | Scup |
| Some Members of the Cichlidae family | |
| *Aequidens latifrons* | Blue acara |
| *Cichlisoma nigrofasciatum* | Congo cichlid |
| *Crenichichla* sp. | Pike cichlid |
| *Pterophyllum scalare* | Angel fish |
| *Tilapia mossambica* | Mozambique mouth breeder |
| *Oreochromis* spp | Tilapia |
| *Sarotherodon aurea* | Golden Tilapia |

TABLE 3

| TAXON NAME | COMMON NAME |
|---|---|
| Some Members of the Centrarchidae family | |
| *Ambloplites rupestris* | Rock bass |
| *Centrarchus macropterus* | Flier |
| *Elassoma evergladei* | Everglades pigmy sunfish |
| *Elassoma okefenokee* | Okefenokee pigmy sunfish |
| *Elassoma zonatum* | Banded pigmy sunfish |
| *Enneacanthus gloriosus* | Bluespotted sunfish |
| *Enneacanthus obesus* | Banded sunfish |
| *Lepomis auritus* | Redbreast sunfish |
| *Lepomis cyanellus* | Green sunfish |
| *Lepomis cyanellus* X *L. gibbosus* | Green x pumpkinseed |
| *Lepomis gibbosus* | Pumpkinseed |
| *Lepomis gulosus* | Warmouth |
| *Lepomis humilis* | Orange-spotted sunfish |
| *Lepomis macrochirus* | Bluegill |
| *Lepomis megalotis* | Longear sunfish |
| *Micropterus coosae* | Shoal bass |
| *Micropterus dolomieui* | Smallmouth bass |
| *Micropterus punctulatus* | Spotted bass |
| *Micropterus salmoides* | Largemouth bass |
| *Pomoxis annularis* | White crappie |
| *Pomoxis nigromaculatus* | Black crappie |

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLES

Example 1

Identification of Two 90 kDA Antigens from *Piscirickettsia salmonis*

Potential *Piscirickettsia salmonis* antigens were identified by screening a *P. salmonis* DNA expression library with polyclonal antibodies raised against *P. salmonis* as follows:

DNA was isolated from *P. salmonis* and partially digested with the restriction enzyme, Sau3A1. The isolated DNA was then cloned into the vector λGEM-12 (Promega) at a BamHI site. λ phage structural proteins were then added and the phages were assembled. A phage library was produced containing 13,750 different phages. The library then was amplified in an *E. coli* host strain.

The library was next transferred to the pGEM-5zf (+) vector (Promega) via the NotI site. An *E. coli* strain was transformed with the library, grown in the presence of ampicillin, and selected for ampicillin resistance. Clones were screened by replica plating using nitrocellulose membranes. Following the lysis of the bacteria on the nitrocellulose membranes, the membranes were blocked with milk and then incubated with anti-*P. salmonis* polyclonal antibodies produced by immunizing rabbits with formaldehyde killed *P. salmonis* bacteria. Next, the membranes were washed and then developed with goat anti-rabbit-HRP conjugate. To detect recircularised plasmids that did not contain the inserts, the membranes were also exposed to X-gal. One isolated clone, designated 1057, appeared to express a 70-90 kDa protein. However, this putative 70-90 kDa protein was not purified, nor was it further characterized.

Initially, a Chilean strain of *Yersinia ruckeri*, a non-human enteric bacterium, was selected as the recombinant host cell to express the 70-90 kDa protein for possible use in a vaccine against SRS. This selection was based on the conventional wisdom that bacterial surface antigens are difficult to express in traditional bacterial vectors, particularly when the desired use for the recombinant vector would be as a vaccine antigen. Thus, it was believed the method of choice for expressing a *P. salmonis* surface antigen, as the 70-90 kDa protein was suspected of being, would be such a non-human enteric bacterium. Indeed, US Published Patent Application No. US20070207165 (A1) and WO2006037383(A1) specifically teach the use of such a recombinant *Yersinia ruckeri* vector to express *P. salmonis* proteins, and specifically exemplify the successful use of this vector to express the $^{Ps}$p45 protein. In fact, this project was deemed completed when a recombinant *Yersinia* vector was isolated that was believed to encode the *P. salmonis* 70-90 kDa protein.

However, the isolated recombinant *Yersinia* vector was fraught with stability and expression problems. Indeed, it was never clear what this recombinant *Yersinia* vector expressed, and more importantly, never clear whether this recombinant *Yersinia* vector ever actually encoded a *P. salmonis* 70-90 kDa protein.

After considerable time and effort, this recombinant *Yersinia* vector was abandoned. The project was picked up again by sequencing the DNA of the parent clone 1057 clone. Surprisingly, rather than encoding one *P. salmonis* 70-90 kDa protein, it was found to contain 11 foreign open reading frames (ORFs). Furthermore, two of these open reading frames, ORF1 and ORF2, unexpectedly were found to encode approximately 90 kDa proteins. The sequences encoding these seemingly unrelated proteins were designated ORF1 (the $^{Ps}p_1$90 protein) and ORF2 (the $^{Ps}p_2$90 protein). The finding of 11 open reading frames, two of which encoded 90 kDa proteins, proves that the original assumption that the 1057 clone encoded a single *P. salmonis* antigen of about 90 kDa was incorrect.

The proteins encoded by ORF1 and ORF2 were further characterized. The protein encoded by ORF 1 ($^{Ps}p_1 90$) was found to have six predictive hydrophobic regions, whereas the protein encoded by ORF 2 ($^{Ps}p_2 90$) was found to have only a single hydrophobic region.

The *P. salmonis* DNA sequence encoding $^{Ps}p_1 90$ (ORF1).

```
SEQ ID NO: 1:
ATGAAAAAGATAATTACAATGATGTTATTGGTGTTATCACTTGTGTTGGTCGCTTGTACC

CCAAGTGAAGAACCACCAACTACAGTGCCAGATGTTGAATCCATCGAATTTAATATGACT

TCAACGACTGTAGCACCAGGTGAACATACACTAGTTGCAAAAGCATTACCTGAAGGATCT

AATCAACAAATTAGATTTAGTATTCAAGGTATTGTATCTGGTGTATCCATTACGGGTGAT

AAGTTAAATGTTGGTAATGCTGTTGAAGATGGTATGAAATTTACAGTCGTAGCAACATCT

GTATATGATCCAACAATTCGTGCAACACTAGAGTTTACAGTTGTAAATGTTGGTGTTGAA

GTTGTTGAAATTAGAACAGAAGAAGAACTACGTGCAATTCATACAAATGAAGGTGGTTTA

TCATTATCTTATGTATTAATGAATGATATTGAACTAACAGCTCCATGGACACCAATTGGT

ATTGCTGAAGTTGAAACTGATTCTGGGCAAATCATTCCAGGTACGCCATTTAATGGTATC

TTTAATGGAAATGGTTTTACAATTAGTGGCATATTAGTTGAAAGTGAAGAACCATTATTT

AATGCAGGATTCTTTGCTCAAATTGGTGCAACTGCAATTGTTAAGAATACAACATTTGAA

GGTATAGTAAATGCAACCGGATGGTCCGGTGGTATCGCAGGTATTAACGAAGGTTTAATA

GAAAATGTTGTATCTAATGTAAGAGTTACTGTAACAGGTACATCCGCAGGTTCGCTAGTA

TCTGTTAATAGAGGTTTAATCCAATATGCTTACGGTATTGGTAAAGTTGTTAGTGAAACA

AACCCTAATACATCAGGTCGTTCTGCTGGTTTAGTGGTTGCTAATGATGGATCAATGATT

GAAGTGTATGGTGACTATCAAGCACTTGGAACACCTAACTATACAGCATTTAGTCCATCA

ACAAACCCAATGTATATGTTACCTACAGTAGATATGAAAACATCTTCAACTTGGGCTTCA

TTTGATGCAGATGTTTGGTATATTGAAAATGGTACATATCCATTATTAAAACATGAAGGA

TTCGTTCCACCAGTGATCGTTCCTGAATTAGGTATTACAATTAAAAATACTGAGTTAAAT

CATGATGTTGAAGTATCAAGTGAACTACAAATAAATGCAGAAGTCATTAACCCAGAAGGT

AGTGAAGTTATTGTTTATGCACTTAAAGAAGCAGTAGCAGGTGTAGCAATTAGTGAAACA

GGTTTAGTTACATTTGATATCACTACAATTGCTGCTAACTTCTCATTTACAGTAGTAGTG

ACAATTGATGGTACTGAAGTTAGTGCTGAAAAAACATTTACAGGCGTATATAACCCTGAA

ATTGTAGATGATACAGTGTATATTGAAACAGAAACACAATTATTAAACTTACTTGCTGGA

CAAACAAACCCAGACAATTTAAGTAAAACATTTGTATTATTAAATGATATTGTCTTAACT

TCTAATTGGACAGCAATTGGTATTGCACCAAATGAAGACGAAGGTATTGTAGGTGTTCCA

TTTACAGGTGTATTTGATGGTCAAGGCTATAAGATCTCAGGTATTAGTATGCCAGGTGGT

GGATGGAATAAAGGTTTCTTTGGATATATTGGAACAACTGGTGTTGTTAAAAACACACAC

TTTGAAGGTAATCTAGAAGCAAACGCATGGTCAGGTGCACTTGCAGCAAATAACTCAGGT

ACTATTCAAGATGTAGTTGTTGATATTGAAGTATATGTCTGGGGTAATAATGGTGGCGCA

ATCGTTGAACATAACCATGGTCTACTTAAAAATATTGTCGTATTAGGTAAAGCTGTATCA

GATAGTGGTCCTACAGCAGTTGGACTGGTTGTTACTAACTTTGGTACTTTAGAAAATGTA

TTTGCTAACGCAGATACAGTAGGTACAGCAAACTTAGTATCTAATGGTGCTCTCGCTGAT

GATGGTAAACACATTATTAGTGCCCAAGACTTTGTTAAAGCTACAACTTATGCAAACTTT

GATAGCGCAATCTGGTTAATCGTAGATGGCCAAGTACCTGTATTAATTAATGAAGATACA

GTATTACCTGAAACAGTAGTTTATATTGAAACAGAAGCAGAATTATTAAGCCTACTTGCT
```

-continued

GGTCAAGTAGATCCAGAAGCATTATCAAAAACATACAAACTTAAAAATGATATCGTTCTA

ACTTCTAATTGGACAGCAATTGGTATTGCACCAAATGAAGACGAAGGTATTGTAGGTGTT

CCATTTACAGGTGTATTTGATGGTCAAGGCTATAAGATCTCAGGTATTAGTATGCCAGGT

GGCGGATGGAATAAAGGTTTCTTTGGTTACATTGGAACAACGGGTGTTGTTAAAAATACA

CACTTTGAAGGTAATATTGAAGCAAACGCATGGTCAGGTGCACTTGCAGCAAATAACTCG

GGTACTATTATGGATGTTGTAGTAGACATTGAAGTATATGTCTGGGGTAATAATGGTGGT

GCAATTGTTGAACATAACCACGGTTTACTTAAAAATATTATCGTCTTAGGTAAAGCTGTA

TCAGATGGTGGTCCTACAGTAGTTGGACTAGTTGTTACTAACTTTGGTACACTAGAAGAT

GTATATGCAAATGTTGACACAGTAGGTACTTTAAACTTAGTATCATTTGGTAGCGTAGCA

GATGATGGTACACACATTATTAGTGCTTCAAACTTTGTTAAAGCAGAAACTTATGCAAAC

TTCTCAAGTGATGTTTGGACAATTATTGATGGTAGCACCCCTGTATTAAAACAAGCATAA

The amino acid sequence of ${}^{Ps}p_1 90$ (ORF1):

SEQ ID NO: 2

MKKIITMMLLVLSLVLVACTPSEEPPTTVPDVESIEFNMTSTTVAPGEHTLVAKALPEGS

NQQIRFSIQGIVSGVSITGDKLNVGNAVEDGMKFTVVATSVYDPTIRATLEFTVVNVGVE

VVEIRTEEELRAIHTNEGGLSLSYVLMNDIELTAPWTPIGIAEVETDSGQIIPGTPFNGI

FNGNGFTISGILVESEEPLFNAGFFAQIGATAIVKNTTFEGIVNATGWSGGIAGINEGLI

ENVVSNVRVTVTGTSAGSLVSVNRGLIQYAYGIGKVVSETNPNTSGRSAGLVVANDGSMI

EVYGDYQALGTPNYTAFSPSTNPMYMLPTVDMKTSSTWASFDADVWYIENGTYPLLKHEG

FVPPVIVPELGITIKNTELNHDVEVSSELQINAEVINPEGSEVIVYALKEAVAGVAISET

GLVTFDITTIAANFSFTVVVTIDGTEVSAEKTFTGVYNPEIVDDTVYIETETQLLNLLAG

QTNPDNLSKTFVLLNDIVLTSNWTAIGIAPNEDEGIVGVPFTGVFDGQGYKISGISMPGG

GWNKGFFGYIGTTGVVKNTHFEGNLEANAWSGALAANNSGTIQDVVVDIEVYVWGNNGGA

IVEHNHGLLKNIVVLGKAVSDSGPTAVGLVVTNFGTLENVFANADTVGTANLVSNGALAD

DGKHIISAQDFVKATTYANFDSAIWLIVDGQVPVLINEDTVLPETVVYIETEAELLSLLA

GQVDPEALSKTYKLKNDIVLTSNWTAIGIAPNEDEGIVGVPFTGVFDGQGYKISGISMPG

GGWNKGFFGYIGTTGVVKNTHFEGNIEANAWSGALAANNSGTIMDVVVDIEVYVWGNNGG

AIVEHNHGLLKNIIVLGKAVSDGGPTVVGLVVTNFGTLEDVYANVDTVGTLNLVSFGSVA

DDGTHIISASNFVKAETYANFSSDVWTIIDGSTPVLKQA

The *P. salmonis* DNA sequence encoding ${}^{Ps}p_2 90$ (ORF2);

SEQ ID NO: 3:

ATGCATTTGGTGTTGTTGCTAAAAAGTAAAAAGGACAAATATATGAAAAAAATAAGC

TTAATAATGATTTTTCTGCTTTCTATCCTATTGGTAAGTTGTGTAGAAAAAGAAGAACCA

AAATTTGATCCAGATAAATATCTAGATTTAGAGAATATTGTATTTGATGATTTTGATAAC

GGAATTGACCCGAATATGTGGGTTATTGGTAATAGTAAGTGGGGTGTAGGTAATGGTGGT

GTCATCTATGAAAATGTCCATTACACAAATGACGGTATTGTAGTTCTTCAAACCAATGGT

GACTTGTATGATGGTCCACTTCGCGGTATTGGTAATACCCATGGCAGACGTACAGGTGCA

ATGATTACAACAAGAGAAGCACTAGGTCCTGGTAGATTTGAAGTACGTATGCGTATTATG

CCACGTTTTGGTTCAACTACTGCTATGTGGACTTACTATTATGATAATGGTATGAACCAT

-continued

GAAATAGATATCGAAAGTAACGTTGAAAATGACTTTAGAAAAGTATGGACTACAAACTGG

ATTAGTTTAACAGAATATAGTACTGTGTCTAATACCTTAGATTTTGCACAAAATGATTTT

GAATGGCGTACATACCGTTTTGACTGGTTTACAGATCCAAAACGCATTGATTATTATATT

GATGAAGTATTAGTTTCATCACAATCTTCTTATGTACCAGATCATGCAGGAGAATTTAAT

ATTGGTAATTGGTTTCCAGATGCTTGGGCAGGTGTACCTGATTTTGAAACAGACTATACC

TATGTAGACTGGTTCAAATATACACCATTTAAAGAACAACCATATACACCAACACCGGCA

AATAATCAAAGTCCTGCAAACTTCTATCCATCAGAACCAATTGAACATCCAATAGCAAAC

CTCATTTCAAATGCAGGTTTTGAAACAGATGCTCCAGCTTGGCGTTATCCTGTAACTAGT

GGTGTGGAACTACTAGAAGGTGAAGGTTTAAACGGATCAAGAGGAATCTTTGTTCCACAA

AATGATATTGCATATCAATTTGTCACAGGATTAGATGAAACCTTTGAAATGACATTTAGT

GCACATGCAAAACTACCTTTAAATGGTAGTGGATATGTTTTATTAGAGTTCTACCCAGCA

GAGACACAAAAAATTGATCAGTATATGATTGAGTTTAACTCAAGCGATGAAGATTTTATA

GCAGATACATTCTATGGTAAAGAATTTACCTTTAATGTACCTCTAGGAACTAAACGTGTT

GAAGTGTCTTTAATTGGAGGAGATTCTGGTATATACTTCGATGATTTATTCTTTAACCTA

ACTAAAAAACCCAGGCCCGAAATTGTAGAAGAAGGTGATGATGTGCAACGTTTAAACATA

GATTTTAAAAATGGTATTGACTCCAATGTTTGGGCAGTTGCAAATCAACGTTGGGGAGGT

ACACATCATGGTGGTGTAATCTTCCAAAACGTACACTACACAGAAGAAGGTAATTTACTC

ATTCAAGCCAATGGTGATTACTATGAAGGTCCATTAAAAGGTGTTGAACAAAATAATGGA

AAACGCACTGGGGGAGCTATCTATACTAAAGAAGCATTTGGCCCAGGATCTTTTGAAGTA

AAAGCTAAAATCATGCCACGTTTTGGGGCAACAACAGCATTTTGGACATTTAACTACTTA

GATGGTATTAATAGTGAAATTGATTTTGAGTTTAACGTAGGCAATGATTTTAGTACAGTT

TGGTTAACCAACTGGTTAACCGAAACAAACTATAACAACTACACCCATCAAATGGATAGT

TTCCATAATGATGGAAACTGGCATATATACCGTTTTGAATGGCATACACTACCGACGCCT

CATATTAAATACTTTATCGATGGCAAACTTGCATATACAGAACATACTAAAGTTCCAACG

ATGTCTGCAAGATACTGGATTGGTGTATGGTTTCCAAATAACTGGGCAGGAGATCCAAAC

TTTGAAACAGATTATTTAGAAGTTGAATATTTCAAATATGAGTCATTCCCGGATCATCCG

TATGTTGTTGGTCCAACTGGGGCATCCTCTCCAACAGCATTTTACCCAACAGCGCCAATA

AAAAAACCAGTTTCTAACCTTTTACCACACGGTAATCTAGATTATGAAACAGGTTATATG

TTAACAGGGGATGCAGTGATTTCAAATGGTGAATTGAAAACTGGTTTACTAGGCAGTGCT

GAGTCTCTTATTAGAGGGTTAAATGATGCCTTTGAACTTACATTAAAGCTTAAAGCAAAA

GCCTCAAATAACGCAACCGTGCGCATTGAGTATTTAGATAAGGATTTAAATGTGATAAGT

GGTGAAGATATTATTGTATCAAACTTAAACGCGAATACATTTACAAACTTTACATCCGTA

ATTAATCTAGTGGAAGGCACTAGAGCCATCAATGTGATTTTTGAGGGAACAAATATCACA

TATGATGACTTATTTATAAATTTAACACACAAGGTGAATTGA

The amino acid sequence of ${}^{Ps}p_2 90$ (ORF2):

SEQ ID NO: 4
MHLVLLLKSKKDKYMKKISLIMIFLLSILLVSCVEKEEPKFDPDKYLDLENIVFDDFDN

GIDPNMWVIGNSKWGVGNGGVIYENVHYTNDGIVVLQTNGDLYDGPLRGIGNTHGRRTGA

-continued

MITTREALGPGRFEVRMRIMPRFGSTTAMWTYYYDNGMNHEIDIESNVENDFRKVWTTNW

ISLTEYSTVSNTLDFAQNDFEWRTYRFDWFTDPKRIDYYIDEVLVSSQSSYVPDHAGEFN

IGNWFPDAWAGVPDFETDYTYVDWFKYTPFKEQPYTPTPANNQSPANFYPSEPIEHPIAN

LISNAGFETDAPAWRYPVTSGVELLEGEGLNGSRGIFVPQNDIAYQFVTGLDETFEMTFS

AHAKLPLNGSGYVLLEFYPAETQKIDQYMIEFNSSDEDFIADTFYGKEFTFNVPLGTKRV

EVSLIGGDSGIYFDDLFFNLTKKPRPEIVEEGDDVQRLNIDFKNGIDSNVWAVANQRWGG

THHGGVIFQNVHYTEEGNLLIQANGDYYEGPLKGVEQNNGKRTGGAIYTKEAFGPGSFEV

KAKIMPRFGATTAFWTFNYLDGINSEIDFEFNVGNDFSTVWLTNWLTETNYNNYTHQMDS

FHNDGNWHIYRFEWHTLPTPHIKYFIDGKLAYTEHTKVPTMSARYWIGVWFPNNWAGDPN

FETDYLEVEYFKYESFPDHPYVVGPTGASSPTAFYPTAPIKKPVSNLLPHGNLDYETGYM

LTGDAVISNGELKTGLLGSAESLITGLNDAFELTLKLKAKASNNATVRIEYLDKDLNVIS

GEDIIVSNLNANTFTNFTSVINLVEGTRAINVIFEGTNITYDDLFINLTHKVN

The DNA sequences encoding ORF 1 and ORF 2 were then optimized for *E. coli* codon usage, avoiding internal TATA boxes, chi sites and ribosomal entry sites, and AT or GC rich sequences. Synthetic genes were made and cloned via pPCR-Script into pEGT1 (the vector was constructed by EGT, and contains a T7/lac promoter, fi origin, is Kanamycin resistant, (KanR), and Hok-Sok). Western blot analyses with anti-peptide antibodies to ORF 1 and ORF 2 confirmed expression of approximately 90 kDa proteins from both ORF 1 and ORF 2.

The *E. coli* optimized DNA sequence encoding ${}^{Ps}p_{1}90$ (ORF1); ORF1 sequences in pEGT1 (EGT optimised sequences):

SEQ ID NO: 5

ATGAAAAAAATCATCACCATGATGCTGCTGGTTCTGAGCCTGGTTCTGGTGGCGTGTACCCCGT

CTGAAGAACCGCCGACCACCGTTCCGGATGTGGAAAGCATTGAATTTAACATGACCAGCACCAC

CGTGGCACCGGGCGAACATACCCTGGTGGCGAAAGCGCTGCCGGAAGGCAGCAACCAGCAGATT

CGTTTTAGCATTCAGGGCATTGTGAGCGGCGTGAGCATTACCGGCGATAAACTGAACGTGGGCA

ACGCCGTGGAAGATGGCATGAAATTTACCGTTGTGGCGACCAGCGTGTATGACCCGACCATTCG

TGCCACCCTGGAATTTACCGTGGTTAACGTTGGCGTGGAAGTGGTGGAAATTCGTACCGAAGAA

GAACTGCGCGCGATTCATACCAACGAAGGCGGCCTGAGCCTGAGCTATGTGCTGATGAACGATA

TTGAACTGACCGCCCCGTGGACCCCGATTGGCATTGCCGAAGTGGAAACCGATAGCGGCCAGAT

TATTCCGGGCACCCCGTTTAACGGCATTTTTAACGGCAACGGCTTTACCATTAGCGGCATTCTG

GTGGAAAGCGAAGAACCGCTGTTTAACGCCGGCTTTTTTGCCCAGATTGGCGCCACCGCCATTG

TGAAAAACACCACCTTTGAAGGCATTGTGAACGCCACCGGCTGGAGCGGCGGCATTGCCGGCAT

TAACGAAGGCCTGATTGAAAACGTTGTTAGCAACGTTCGTGTGACCGTGACCGGCACCAGCGCC

GGTAGCCTGGTGAGCGTGAACCGTGGCCTGATTCAGTATGCCTATGGCATTGGCAAAGTGGTGA

GCGAAACCAACCCGAACACCAGCGGTCGTAGCGCCGGTCTGGTGGTGGCGAACGATGGCAGCAT

GATTGAAGTGTATGGCGATTATCAGGCGCTGGGCACCCCGAACTATACCGCCTTTAGCCCGAGC

ACCAACCCGATGTATATGCTGCCGACCGTGGATATGAAAACCAGCAGCACCTGGGCGAGCTTTG

ATGCCGATGTGTGGTATATCGAAAACGGCACCTATCCGCTGCTGAAACATGAAGGCTTTGTGCC

GCCGGTTATTGTGCCGGAACTGGGCATTACCATTAAAAACACCGAACTGAACCATGATGTGGAA

GTGAGCAGCGAACTGCAGATTAACGCCGAAGTGATTAACCCGGAAGGTAGCGAAGTTATTGTTT

ATGCCCTGAAAGAAGCGGTGGCGGGCGTTGCCATTAGCGAAACCGGCCTGGTGACCTTTGATAT

TACCACCATTGCGGCGAACTTTAGCTTTACCGTGGTGGTGACCATTGATGGCACCGAAGTGAGC

-continued

GCCGAAAAAACCTTTACCGGCGTGTATAACCCGGAAATTGTGGATGATACCGTCTATATCGAAA

CCGAAACCCAGCTGCTGAACCTGCTGGCGGGCCAGACCAACCCGGATAACCTGAGCAAAACCTT

TGTGCTGCTGAATGACATTGTGCTGACCAGCAACTGGACCGCCATTGGTATTGCCCCGAACGAA

GATGAAGGTATTGTTGGCGTTCCGTTTACCGGTGTGTTTGATGGCCAGGGCTACAAAATTAGCG

GTATTAGCATGCCGGGTGGCGGCTGGAACAAAGGCTTTTTTGGCTATATCGGCACCACCGGCGT

GGTGAAAAATACCCATTTCGAAGGTAACCTGGAAGCGAACGCCTGGTCTGGCGCCCTGGCGGCG

AACAACAGCGGCACCATTCAGGATGTGGTGGATATCGAAGTGTATGTTTGGGGCAACAACG

GCGGTGCCATTGTGGAACATAACCATGGCCTGCTGAAAAACATTGTGGTGCTGGGTAAAGCGGT

GAGCGATAGCGGTCCGACCGCCGTGGGTCTGGTGGTTACCAACTTTGGCACCCTGGAAAACGTG

TTTGCCAACGCCGATACCGTGGGCACCGCCAACCTGGTGAGCAACGGTGCCCTGGCGGATGATG

GCAAACACATTATCAGCGCCCAGGATTTTGTGAAAGCGACCACCTATGCCAACTTTGATAGCGC

CATTTGGCTGATTGTGGATGGCCAGGTGCCGGTTCTGATTAACGAAGATACCGTGCTGCCGGAA

ACCGTGGTGTATATTGAAACCGAAGCGGAACTGCTGTCTCTGCTGGCGGGTCAGGTGGATCCGG

AAGCGCTGTCTAAAACCTACAAACTGAAAAACGATATCGTGCTGACCTCTAACTGGACGGCGAT

CGGCATCGCTCCGAATGAAGATGAGGGCATCGTCGGCGTCCCGTTCACCGGCGTGTTCGACGGT

CAGGGTTATAAAATTTCTGGCATTTCTATGCCGGGTGGTGGTTGGAATAAAGGTTTCTTCGGTT

ACATTGGCACCACCGGTGTTGTTAAAAACACTCACTTTGAGGGTAATATTGAAGCGAATGCCTG

GAGCGGCGCTCTGGCCGCCAACAACTCTGGCACCATTATGGATGTTGTTGTCGATATTGAAGTT

TACGTGTGGGGCAATAATGGTGGCGCCATCGTTGAACACAATCACGGTCTGCTGAAAAATATCA

TTGTTCTGGGTAAAGCCGTTTCTGATGGCGGTCCGACGGTGGTGGGCCTGGTTGTGACGAATTT

CGGCACGCTGGAAGATGTGTATGCCAATGTTGATACCGTTGGCACCCTGAATCTGGTGAGCTTT

GGCAGCGTGGCCGATGATGGCACCCATATCATTAGCGCCAGCAACTTTGTTAAAGCGGAAACCT

ATGCCAATTTTAGCAGCGATGTGTGGACCATTATTGATGGCAGCACCCCGGTGCTGAAACAGGC

GTAA

The *E. coli* optimized DNA sequence encoding ${}^{Ps}p_2 90$ (ORF2); ORF2 sequences in pEGT1 (EGT optimised sequences). Note the corresponding *E. coli* optimized ${}^{Ps}p_2 90$ amino acid sequence begins with an N-terminal histidine instead of the N-terminal proline for the naturally occurring ${}^{Ps}p_2 90$ protein.

SEQ ID NO: 6

ATGCATCTGGTGCTGCTGCTGAAAAGCAAAAAAGATAAATACATGAA

AAAAATCAGCCTGATCATGATTTTTCTGCTGTCTATTCTGCTGGTGAGCT

GTGTGGAAAAAGAAGAACCGAAATTCGATCCGGATAAATACCTGGATCTG

GAAAACATCGTTTTCGATGATTTCGATAACGGCATTGATCCGAACATGTG

GGTGATTGGCAACAGCAAATGGGGCGTGGGCAACGGCGGCGTGATTTATG

AAAACGTCCATTACACCAACGATGGCATTGTGGTGCTGCAGACCAACGGC

GATCTGTATGATGGCCCGCTGCGTGGCATTGGCAACACCCATGGCCGTCG

TACCGGCGCCATGATTACCACCCGTGAAGCGCTGGGTCCGGGCCGTTTTG

AAGTTCGTATGCGCATTATGCCGCGTTTTGGCAGCACCACCGCCATGTGG

ACCTATTATTATGATAACGGCATGAACCACGAAATTGATATCGAAAGCAA

-continued

CGTGGAAAACGATTTTCGTAAAGTTTGGACCACCAACTGGATCAGCCTGA

CCGAATATAGCACCGTGAGCAACACCCTGGATTTTGCCCAGAACGATTTT

GAATGGCGTACCTATCGTTTTGATTGGTTTACCGATCCGAAACGTATCGA

TTACTACATTGATGAAGTGCTGGTGAGCAGCCAGAGCAGCTATGTGCCGG

ATCATGCCGGCGAATTTAACATTGGCAACTGGTTTCCGGATGCCTGGGCA

GGCGTTCCGGATTTTGAAACCGATTATACCTACGTGGATTGGTTTAAATA

CACCCCGTTTAAAGAACAGCCGTATACCCCGACCCCGGCGAATAACCAGA

GCCCGGCGAACTTTTATCCGAGCGAACCGATTGAACATCCGATTGCCAAC

CTGATTAGCAACGCCGGCTTCGAAACCGATGCCCCGGCATGGCGTTATCC

GGTGACCAGCGGCGTGGAACTGCTGGAAGGCGAAGGCCTGAACGGCAGCC

GTGGCATTTTTGTGCCGCAGAACGATATTGCCTATCAGTTTGTGACCGGC

CTGGATGAAACCTTTGAAATGACCTTTAGCGCCCATGCCAAACTGCCGCT

GAACGGTAGCGGCTATGTGCTGCTGGAATTTTATCCGGCGGAAACCCAGA

AAATTGACCAGTATATGATCGAATTCAACAGCAGCGATGAAGATTTTATC

-continued

```
GCCGATACCTTCTATGGCAAAGAATTTACCTTTAACGTTCCGCTGGGCAC
CAAACGTGTGGAAGTGAGCCTGATTGGCGGCGATAGCGGCATTTATTTTG
ACGACCTGTTCTTCAACCTGACCAAAAAACCGCGTCCGGAAATTGTGGAA
GAAGGCGACGACGTTCAGCGTCTGAACATTGATTTCAAAAACGGCATCGA
TAGCAACGTGTGGGCGGTGGCGAATCAGCGTTGGGGCGGCACGCATCATG
GCGGTGTGATTTTTCAGAACGTTCACTATACCGAAGAAGGCAACCTGCTG
ATTCAGGCGAACGGCGATTATTATGAAGGTCCGCTGAAAGGCGTTGAACA
GAACAACGGCAAACGTACCGGCGGTGCCATTTATACCAAAGAAGCGTTTG
GCCCGGGTAGCTTTGAAGTGAAAGCGAAAATCATGCCGCGCTTTGGTGCC
ACCACGGCGTTTTGGACCTTTAACTATCTGGATGGCATCAACAGCGAAAT
CGATTTTGAATTCAACGTGGGCAACGATTTTAGCACCGTGTGGCTGACCA
ACTGGCTGACCGAAACCAACTATAACAACTACACCCATCAGATGGATAGC
TTTCATAACGATGGCAACTGGCATATTTATCGCTTTGAATGGCATACCCT
GCCGACCCCGCATATTAAATACTTCATCGACGGCAAACTGGCGTATACCG
AACATACCAAAGTGCCGACCATGAGCGCCCGTTATTGGATTGGCGTGTGG
TTTCCGAACAACTGGGCGGGTGATCCGAACTTTGAAACCGACTATCTGGA
AGTGGAATACTTCAAATACGAAAGCTTTCCGGATCATCCGTATGTTGTTG
GCCCGACCGGTGCCTCTAGCCCGACCGCCTTTTATCCGACCGCCCCGATT
AAAAAACCGGTGAGCAACCTGCTGCCGCATGGCAACCTGGATTATGAAAC
CGGCTATATGCTGACCGGCGATGCCGTGATTAGCAATGGCGAACTGAAAA
CCGGCCTGCTGGGCAGCGCCGAAAGCCTGATTACCGGCCTGAACGATGCC
TTTGAACTGACCCTGAAACTGAAAGCGAAAGCGAGCAACAACGCCACCGT
TCGTATTGAATACCTGGATAAAGATCTGAACGTTATCAGCGGCGAAGATA
TTATTGTGAGCAATCTGAACGCCAACACCTTTACCAACTTTACCAGCGTG
ATTAACCTGGTTGAAGGCACCCGTGCCATTAACGTTATTTTCGAAGGCAC
GAACATTACCTATGATGACCTGTTTATTAACCTGACCCACAAAGTGAACT
AATAAGTCGACG
```

Example 2

Expression of the Two 90 kDA Antigens from *Piscirickettsia salmonis*

Upstream Process

Batches of the two 90 kDa antigens were produced,

The strains used were as follows:

*E. coli* HMS174(DE3)/pEGT1/AL-ORF1-90 kDa ($^{Ps}p_1 90$)

*E. coli* HMS174(DE3)/pEGT1/AL-ORF2-90 kDa ($^{Ps}p_2 90$)

The strains were grown in shake-flasks. Each batch was prepared as a pool of 5 shake flasks.

The protocol was as follows:

1. 50 μl of a glycerol stock was grown in 200 mL of YES medium [30 g/l yeast extract, 5 g/l NaCl], supplemented with kanamycin 100 mg/l [500 ml medium in a 2 L shake-flask].
2. The culture was incubated at 37° C., with an agitation of 270 rpm.
3. When the $OD_{600}$ reached 2.1, protein expression was induced by the addition of 1 mM isopropyl-β-D-thiogalactopyranoside ("IPTG").
4. The final $OD_{600}$ was around 2.2 for the ORF1-strain, and 1.7 for the ORF2-strain.
5. At the end of the culture, the pellets were harvested by centrifugation (5000 g, 30 min., 4° C.) and the supernatant discarded.
6. Pellets were collected and stored at −20° C.
7. Cell breakage: Pellets were resuspended in 115 mL 20 mM Tris buffer pH 7 for the ORF1-antigen and in 85 ml 20 mM Tris buffer pH 7 for the ORF2-antigen. A French Press was used to break the cells and 2 cycles were performed (40K; 1000 PSI; room temperature, all samples are keep on ice). Volumes collected were 120 ml for the ORF1-antigen and 75 ml for the ORF2-antigen. The samples were stored at −20° C.

Example 3

Purification of *Piscirickettsia salmonis* 90 kDa Antigens Downstream Process 120 ml of the ORF1 antigen ($^{Ps}p_1 90$) and 75 ml of the ORF2 ($^{Ps}p_2 90$) antigen samples prepared according to Example 2 were semi-purified using a 300 kDa ultrafiltration. The retentates were concentrated to 50 ml and then diafiltered against 5 volumes of 20 mM Tris, pH 7.5. Both antigens were found to be in the retentate fractions forming large aggregates. The two antigens were then formulated by diafiltration with PBS buffer (137 mM NaCl, 2.7 mM KCl, 8 mM $Na_2HPO_4.12H_2O$, 1.5 mM $KH_2PO_4$, pH=7.45) using a 300 kDa molecular weight cut-off ultrafiltration membrane.

Example 4

Formulation of Vaccines 125 ml of the 300-kDa retentates, as produced by Example 3, were then diafiltrated against 5 volumes of PBS buffer (137 mM NaCl, 2.7 mM KCl, 8 mM $Na_2HPO_4.12H_2O$, 1.5 mM $KH_2PO_4$, pH=7.45). The retentates containing the respective ORF-1 and ORF-2 90-kDa-antigens were collected and stored at −20° C. The antigens were then sterile filtered through 0.2 μm filters prior to vaccine blending.

The final protein concentration for the two antigens preparations were 0.089 mg/ml for ORF1 and 0.015 mg/ml of ORF2. SDS PAGE gels were run and scanned in order to determine the ratio of the 90 kDa antigens to total protein. The ORF1 antigen was found to be 25.7% of the total protein and the ORF 2 antigen was found to be 8.3%. Final concentrations of the specific antigens were therefore 0.023 mg/ml for ORF 1 ($^{Ps}p_1 90$) and 0.0012 mg/ml for ORF 2 ($^{Ps}p_2 90$).

The Vaccines were Blended as Follows:

The oil based adjuvant Montanide ISA 711 (Seppic) was used in a 70:30 (adjuvant:antigen) ratio.

| | |
|---|---|
| Blend 1 (90 kDa ORF1) | 15 ml (0.345 mg) antigen, 35 ml adjuvant |
| Blend 2 (90 kDa ORF2) | 15 ml (0.018 mg) antigen, 35 ml adjuvant |
| Blend 3 (PBS control) | 15 ml PBS, 35 ml adjuvant |

Following mixing of the aqueous and oil phases, each of the respective vaccines was homogenised by serial passages through a syringe.

Example 5

Laboratory Efficacy Trial of Vaccination of Atlantic Salmon (*Salmo salar*) Against SRS The vaccines prepared according to Example 4 above, were tested for efficacy employing a challenge with *P. salmonis* at VESO Vikan, Norway.

Atlantic salmon (*Salmo salar* L., AquaGen Standard) were vaccinated at an average weight of 16.1 g in fresh water. Water temperature was 12° C. to 15° C.±1° C. during the immunisation period and 15° C.± 1° C. during the *P. salmonis* challenges. The water flow rate was 0.8 l/kg fish per min. The fish density was a maximum of 40 kg/$m^3$.

Fish were acclimatised for 18 days after arrival at VESO Vikan. 105 fish were anesthetized and injected with 0.1 ml of each vaccine per fish, and a control group of 105 fish was anesthetized and injected with 0.1 ml of physiological saline with 0.9% NaCl per fish. The fish were tagged with ink and by fin cutting. The test groups and the control group were pooled after vaccination. 12 days before challenge the fish were sorted into two parallel tanks, with 50 fish per group per tank. 10 days before challenge the water temperature was raised to 15° C.

Laboratory Efficacy Trial—challenge 48-52 fish from each group were challenged with *P. salmonis* by intraperitoneal injection in two duplicate tanks 8 weeks after vaccination. The same challenge dose was used in both tanks (0.1 ml 1:1000 dilution per fish, and the dose was determined following prechallenge experiments). The temperature in the rearing water was 15° C. during the challenge. The challenge material was grown at The National Veterinary Institute, Oslo and was kept at −75° C. until challenge. On the day of challenge, the challenge material was dose adjusted according to the results obtained in the pre-challenge. The challenge material was diluted in PBS with 1.3% NaCl.

Relative percentage survival ($RPS_{60}$) was calculated on the day that control group mortality equalled exactly 60% or, if inappropriate, at the time corresponding to 60% control group mortality (t60) according to the expression:

$$RPS_{60} = \left(1 - \left(\frac{MV_{60} \times 100}{n_v \times 60}\right)\right) \times 100$$

In cases where control-group mortality did not equal exactly 60% on any given day of the trial, cumulative mortality of vaccinates at the time corresponding to 60% control group mortality was estimated from the expression.

$$MV_{60} = MV_{60-1} + \left(\frac{((0.6 \times n_c) - MC_{60-1}) \times (MV_{60+1} - MV_{60-1})}{(MC_{60+1} - MC_{60-1})}\right)$$

The following definitions apply to the parameters of the first and second expressions, above.

$MV_{60}$=cumulative mortality of vaccinates at 60% cumulative control group mortality.

$MC_{60-1}$=number of mortalities in control group on last day before cumulative mortality rate in control group exceeds 60%.

$MC_{60+1}$=number of mortalities in control group on first day after cumulative mortality rate in control group has exceeded 60%.

$MV_{60-1}$=number of mortalities in vaccinated group on last day before cumulative mortality rate in control group exceeds 60%.

$MV_{60+1}$=number of mortalities in vaccinated group on first day after cumulative mortality rate in control group has exceeded 60%.

$n_c$=total number of fish in control group.

$n_v$=total number of fish in vaccinated group $RPS_{60}$=Relative percentage survival at 60% control group mortality.

$RPS_{60}$ was subsequently calculated from the first expression, with the following results.

Results

Results for the challenge are summarized by FIG. 1, and by the tables below. As can be seen in FIG. 1, the challenged animals vaccinated by saline control (diamonds) or adjuvant control (squares) exhibited up to about 75% mortality by days 25-30 post challenge. In contrast, animals vaccinated with the ORF-1 antigen ($^{Ps}p_1 90$), denoted by "X" and the ORF-2 antigen ($^{Ps}p_2 90$) denoted by triangles, exhibited both delayed and reduced mortality. In particular, animals vaccinated with ORF-2 ($^{Ps}p_2 90$) exhibited no more than 5% mortality out to day 32.

Cumulative Mortality as Defined by $RPS_{60}$

TABLE 4

Tanks A and B were set up with a random mix of vaccinated and saline vaccinated fish.

| Vaccine | $RPS_{60}$ Tank A | $RPS_{60}$ Tank B | Mean $RPS_{60}$ |
|---|---|---|---|
| 90 kDa ORF 1 ($^{Ps}p_1$ 90) | 96.8 | 100.0 | 98.4 |
| 90 kDa ORF 2 ($^{Ps}p_2$90) | 50.0 | 77.1 | 63.6 |
| Adjuvant + PBS | 2.0 | 11.7 | 6.9 |

In order for the test results to be acceptable, mortalities in the control group must reach 60% within 30 days after the first specific mortality has been recorded. As the results met these criteria the results were accepted as valid.

The results therefore demonstrate that both the 90 kDa ORF 1 antigen ($^{Ps}p_1 90$) and the 90 kDa ORF 2 antigen ($^{Ps}p_2 90$) are capable to provide significant protection in salmon against SRS caused by *P. salmonis.*

Example 6

Production Method of VP2var or VP3 (50 Liter Scale)

The yeast strains: *Pichia pastoris* GS115-pPICZαB—VP2var. The Pichia expression system is used to express the IPN protein antigens [Research Corporation Technologies, Tucson, Ariz., see U.S. Pat. Nos. 4,808,537, 4,837,148, 4,879,231, the contents of which are hereby incorporated by reference in their entireties.

Preculture: A 2-liter baffled shake-flask containing 400 ml of YSG+ (see below) is inoculated with 600 μl of the above-identified yeast strain. The culture is incubated at 30° C., with an agitation of 270 rpm, during 23-25 hours. The optical density at 600 nm ($OD_{600nm}$) is >15 units (using a NOVASPEC II spectrophotometer), as set forth by Table 5, below.

TABLE 5

| Composition of the Medium YSG+: | |
|---|---|
| COMPONENTS | CONCENTRATION |
| Yeast Extract | 6 g/l |
| Papaïc Soy Pepton | 5 g/l |
| Glycerol | 20 g/l |

Fermentation: The fermentor Braun D50 is prepared with 50 liters of growth medium (SAPPEY, see below). The fermentor is inoculated with a volume ($V_{preculture}$) of preculture determined by the equation:

$$V_{preculture}(\text{ml})=V_{fermentor}(\text{ml})\times 0.05/OD_{600preculture}$$

Where, $V_{fermentor}$ is defined as the volume of the growth medium in the fermentor, and the $OD_{600preculture}$ is the optical density determined at 600 nm of the preculture solution obtained above.

TABLE 6

| Parameters for Fermentation | |
|---|---|
| PARAMETERS | SET POINTS |
| pH | 6* |
| Temperature | 30° C. |
| Air-flow | 80 l/min. |
| $PO_2$ | 30%** |
| Agitation | 400-(600) rpm |
| Pressure | 100 mbar |

*regulation with acid ($HNO_3$ 10%) and base ($NH_4OH$ 12.5%)

**with an action on the agitation to maintain the $PO_2$ at 30% Automatic regulation of foam with SAG471.

TABLE 7

| Composition of Growth Medium SAPPEY per 1 Liter: | |
|---|---|
| Components | Volumes |
| Base solution | 900 ml |
| Complement solution 1 | 100 ml |
| PTM1 solution | 4.76 ml |

TABLE 8

| Quantities per 1 Liter of Base Solution [The solution is autoclaved in the fermentor (20 min., 121° C.)] | |
|---|---|
| Components | Quantity |
| Yeast Extract | 11.11 g/l |
| Papaïc Soy Pepton | 22.22 g/l |
| Antifoam SAG471 | 0.11 ml/l |

TABLE 9

| Quantities per 1 Liter of COMPLEMENT SOLUTION 1 (The solution is sterilised by filtration with a 0.22 μm pore membrane) | |
|---|---|
| Components | Quantity |
| $K_2HPO_4$ | 23 g/l |
| $KH_2PO_4$ | 118 g/l |
| Glycerol | 100 g/l |

TABLE 10

| Quantity for 1 Liter of PTM1 SOLUTION | |
|---|---|
| Components | Quantity |
| $CuSO_4 \cdot 5H_2O$ | 6 g/l |
| NaI | 0.08 g/l |
| $MnSO_4 \cdot H_2O$ | 3 g/l |
| $Na_2MoO_4 \cdot 2H_2O$ | 0.2 g/l |
| $H_3BO_3$ | 0.02 g/l |
| $CoCl_2 \cdot 6H_2O$ | 0.92 g/l |
| $ZnCl_2$ | 20 g/l |
| $FeSO_4 \cdot 7H_2O$ | 65 g/l |
| d-biotine | 0.2 g/l |
| $H_2SO_4$ | 5 ml/l |

The solution is sterilized by filtration with a 0.22 μm pore membrane. The PTM1 solution must be added in the fermentor separately from the complement solution 1.

TABLE 11

| Composition of "INDUCTION SOLUTIONS" per 1 Liter (The methanol is added by sterile filtration with a 0.22 μm pore membrane) | |
|---|---|
| Components | Volumes |
| Methanol 100% | 6.3 ml/l of culture |
| Yeast Extract solution | 22.5 ml/l of culture |

TABLE 12

| Quantity for 1 Liter of YEAST EXTRACT SOLUTION [This solution is autoclaved (20 min., 121° C.)] | |
|---|---|
| Components | Quantity |
| Yeast Extract | 222 g/l |

After 24 hours of growth, a first induction of recombinant protein expression is realized by the addition of methanol and yeast extract solution. At this moment, the $OD_{600nm}$ is greater than about 10 units. After the induction the $pO_2$ decreases quickly. After about 1 hour, it increases slowly to saturation. A second induction is realized after 48 hours of culture in the same conditions. The $OD_{600nm}$ reached is greater than about 13 units. After 72 hours of growth, the fermentor is cooled to a temperature lower than 20° C. The $OD_{600nm}$ reached is greater than about 13 units.

Harvest and filling: The cells from the fermentor are then harvested. The culture is centrifuged (5000 g, 4° C., 20 min) in order to eliminate the pellets. The supernatant is aseptically filtrated with a 0.2 μm pore membrane (Sartobran P) and 2.5 liter aliquots are placed into one gallon bottles. These bottles are then stored at −20° C.

Example 7

An Injectable Vaccine for SRS, IPN and Furunculosis

SUMMARY

One injectable vaccine of the present invention is a water-in-oil type vaccine that comprises a suspension of:

(i) two inactivated strains of *Aeromonas salmonicida* (*MT*004 and MT423), (ii) two recombinant IPN viral proteins (VP2 and VP3) or antigenic fragments thereof, that are expressed by transformed yeast, *Pichia pastoris* in 0.85% p/v sterile saline, and (iii) a suspension comprising inactivated recombinant strains of *E. coli* encoding $^{Ps}p_1 90$ and/or $^{Ps}p_2 90$, in phosphate buffered saline.

The VP2 (VP2var) recombinant proteins are expressed by transformed yeast, *Pichia pastoris* BCCM Accession No. IHEM 20069 and/or BCCM Accession No. IHEM 20070, whereas the VP3 recombinant proteins are expressed by BCCM Accession No. IHEM 20071, and/or BCCM Accession No. IHEM 20072. The oily adjuvant is MONTANIDE ISA711 and constitutes 70% of the vaccine's total volume. The formulation may contain residual amounts of formaldehyde, derived from inactivation of the cultures.

This particular vaccine is designed and recommended for administration by intraperitoneal injection, to protect against salmonid rickettsial septicaemia, infectious pancreatic necrosis and furunculosis in fish, more particularly salmonids, and even more particularly, in salmon.

Presentation

This vaccine is presented in 500 ml high density polyethylene infusion flasks, closed with grey nitrile stoppers and having aluminium seals. The bottles and stoppers comply with the requirements of the relevant monographs of the European Pharmacopoeia (Ph. Eur). The containers are autoclaved at 121° C. for 20 minutes. The stoppers are autoclaved at 121° C. for 60 minutes.

Production

Production of *A. salmonicida* MT004 Antigen:

An ampoule of lyophilized work seed is removed from storage and is reconstituted and incubated. This culture is then inoculated in 4 liters of sterile iron-deficient TSB to form the production culture, and then incubated at approximately 21.5° C. for 36-48 hours.

The resulting culture is then aseptically inoculated in 15-18 liters of sterile iron-deficient TSB. It is incubated at approximately 21.5° C. for 24 to 48 hours. Then a solution of sterile formaldehyde is added to the flasks to inactivate the culture. Each culture is mixed vigorously following the addition of the formaldehyde solution and is then transferred aseptically to a sterile storage bottle. The culture is kept at approximately 22° C. for 96-100 hours to ensure the inactivation of bacterial cultures and protease activity. The formaldehyde is neutralized by the addition of a solution of 15% sodium metabisulfite. Neutralisation is completed in 20-24 hours at a temperature of approximately 22° C. The inactivated harvests are stored at 2-8° C. until they are required for mixing. The production of *A. salmonicida* MT004 antigen can also be performed as described below for MT423.

Production of *A. salmonicida* MT423 Antigen:

An ampoule of lyophilized work seed is removed from storage and reconstituted and incubated. This culture is then inoculated in 300 ml of sterile iron-supplemented TSB to form the production culture, and then incubated at approximately 21.5° C. for 36-48 hours.

The culture is next inoculated aseptically in 4 liters of sterile iron-supplemented TSB. It is incubated at approximately 21.5° C. for 36 to 48 hours. The culture of production seed is transferred aseptically to 150 liters of sterile iron-supplemented TSB in a fermentor and incubated at approximately 21.5° C. for 20-24 hours.

Then a solution of sterile formaldehyde is added to the culture flasks to inactivate them. Each culture is mixed vigorously following the addition of the formaldehyde solution and is transferred aseptically to a sterile storage bottle. The culture is kept at approximately 22° C. for 96-100 hours to ensure inactivation of the bacterial cultures and protease activity. The formaldehyde is neutralized by adding a solution of 15% sodium metabisulfite. Neutralization is completed in 20-24 hours at a temperature of approximately 22° C. The inactivated harvests are stored at 2-8° C. until they are required for mixing Production of Recombinant Proteins IPN (VP2 VAR) and IPN VP3:

Recombinant proteins IPN (VP2 VAR) and IPN VP3 are prepared and stored as described in Example 6 above.

Production of Antigens of *Piscirickettsia salmonis:*

The $^{Ps}p_1 90$ and $^{Ps}p_2 90$ antigens are prepared for the formulation of the vaccine as described in Example 4 above.

Mixing of the Final Vaccine

Bulk antigens are mixed with the other antigen components, phosphate-buffered saline solution, and the oil component to obtain a bulk vaccine of the desired cell concentration.

The volumes of bulk antigens required (calculated on the individual concentrations of bulk antigen, the required concentrations of these in the end product and the batch size) are removed from storage. The bulk antigens are transferred to cool, sterile containers and are mixed thoroughly.

The volume of sterile saline required is calculated and transferred aseptically to the mixed bulk antigens. The antigens and saline are thoroughly mixed and the pH is adjusted to pH 7.0-7.4 with 10 M sodium hydroxide or 10 M hydrochloric acid (aqueous phase).

The weight of sterile oily phase required is calculated and transferred aseptically to a sterile mixing container. The oily and aqueous phases are emulsified for 5 minutes at approximately 3000 rpm. The emulsified mix is maintained at ambient temperature for 24 hours. The mix is placed in the final containers, with a nominal fill value of 505 ml. The stoppers are inserted aseptically and the seals are applied. Each container is labeled, packaged and stored at +2° C. to +8° C. under quarantine until released for sale. The batch size varies according to production requirements and is normally within the range of 100 liters to 1500 liters.

Materials

*Piscirickettsia salmonis* antigens are prepared as described above. In addition two strains of *Aeromonas salmonicida* are used, which derive from isolated naturally infected fish obtained from fish farmed in Scotland. In spite of the fact that there is no evidence that there is any serological distinction between different strains of *Aeromonas salmonicida*, there is a scientific basis for including more than one strain in this vaccine. This is due to the fact that different isolated ones may be A-layer positive or negative. Considering that the presence or absence of this layer may not be directly linked to virulence, the absence of an A-layer allows greater exposure to outer membrane proteins (OMPs), and in particular, those OMPs produced only under conditions of iron restriction, as may occur during the infection process. As a result, the production and immunological availability of the iron restriction outer membrane proteins (IROMPs) is thought to be important to the efficacy of the vaccine.

*Aeromonas salmonicida* (MT004):

The MT004 strain is an A-layer negative strain which is cultivated under conditions of iron restriction. Development under these conditions results in the production of specific iron restriction outer membrane proteins that stimulate the production of bacterial antibodies following intraperitoneal inoculation.

The strain was originally isolated from dying Atlantic salmon during an outbreak of furunculosis in on a salmon farm on the West Coast of Scotland in October 1985. It was passaged through tryptone soya broth six times and remained virulent to the host animal.

*Aeromonas salmonicida* (MT423):

The MT423 strain is an A-layer positive strain that has been cultivated in a fermentor under conditions of iron restriction. A-layer is a component of successful *A. salmonicida* vaccines and supplementation with iron has increased the protection afforded by the furunculosis vaccine.

The MT423 strain was isolated from sick Atlantic salmon from a salmon farm at Stirling University. It was passaged 16 times in Atlantic salmon and remained virulent to the host animal and is therefore appropriate for use as a vaccine strain.

Both strains are inactivated by exposure to formaldehyde, being in non-infecting organisms, whereas it retains its ability to stimulate an immune response in vaccinated fish.

The vaccine also contains the recombinant proteins VP2 var and VP3 of IPNV as described in Example 6 above.

Other Reagents are provided in Table 13:

TABLE 13

| Reagents | | |
|---|---|---|
| REAGENT | COMPONENTS | CHARACTERISTICS |
| Tryptone Soya Broth (TSB) | Pancreatic casein digestive enzyme | Cow's milk from herds certified BSE free, originally from France, but currently from New Zealand. Porcine enzymes from France, Italy and Holland. |
| | Soya digestive papain | No materials of biological origin |
| | Sodium chloride | |
| | Hydrogenated dipotassium phosphate | |
| | Dextrose | Synthetic or of non-animal origin |
| | Purified water | Meets the requirements of the European Pharmacopoeia. |
| Hydrochloric acid (pH adjustment) | — | Meets the requirements of the European Pharmacopoeia. |
| Sodium hydroxide (pH adjustment) | — | Meets the requirements of the European Pharmacopoeia. |
| Formaldehyde (Inactivator) | — | Meets the requirements of the European Pharmacopoeia. |
| Saline solution (Diluent) | Sodium chloride | Meets the requirements of the European Pharmacopoeia. |
| | Purified water | Meets the requirements of the European Pharmacopoeia. |
| Montanide ISA711 (Adjuvant) | Contains oleic acid | EDQM Certified available |

Assays

Several tests are carried out to ensure that the consistency and quality of the vaccine and its components are maintained. These tests are described below.

*Aeromonas salmonicida* Strains MT004 and MT423:

The test methods used for both antigens are the same, except that the test for the presence of IROMPS is not used for the MT423 strain, since this is multiplied in an iron-enriched medium. In addition, the criteria used for some tests are different for each strain. For the sake of simplicity, the following test descriptions specify the criterion for each strain where it is appropriate.

Purity Tests—Gram Stain:

Gram stain purity tests are carried out on each subculture during multiplication from seed to production culture. The test provides a rapid indication that the cultivated organism has the hoped for microscopic appearance and that no atypical organism is present.

The test method is a simple Gram stain that uses conventional techniques and materials. Known Gram positive and negative control organisms are stained each time to confirm that staining and discoloration are appropriate. The test sample must only show small Gram negative rods.

Purity Test and Characteristics of the Culture:

An additional purity test is carried out on each of the 20 liter complete cultures and on the culture in the final fermentor. The test confirms the purity of the culture and contributes to global identity security. A sample of the culture is grown on plates of tryptone soya agar and incubated at 22° C. for at least 48 hours, long enough for the different colonies to become visible. Plates inoculated with the test culture must exhibit only one type of bacterial colony. These colonies must be typical of *Aeromonas salmonicida.*

The *Aeromonas salmonicida* MT004 strain forms semi-translucent, round, convex, cream-colored colonies with regular edges. A red-brown pigmentation is produced which spreads through the medium after around 24 hours of culture. The *Aeromonas salmonicida* MT423 strain: Semi-translucent, round, convex, cream-colored colonies with regular edges, but developing more slowly than the MT004 strain.

Identity of the culture: The identity of a given culture is confirmed in the samples on final fermentation. Identity tests are carried out on the final culture prior to inactivation to confirm that the correct organism has been cultured. It must be emphasized that none of these tests can differentiate the strains, but all contribute to the security of identifying the species. In addition to the purity tests, identity is confirmed by means of biochemical and agglutination characteristics:

- Demonstration of the use of glucose without gas production.
  - A sample from the final culture is inoculated in peptone water containing 1% glucose and phenol red in tubes containing an inverted Durham tube. The inoculated cultures are incubated at 22° C. for 24-48 hours. The test sample must show the use of glucose, indicated by acid production, without gas being produced.
- Demonstration of positive metabolism of cytochrome oxidase using commercially available impregnated filter papers:
  - A single colony from the purity test plate (culture characteristics) is spread over the filter paper. A positive result is indicated by the development of a pinkish purple pigment while a negative result is indicated by no color change. The cultures must generate a pinkish purple coloration on the test paper, indicating positive cytochrome oxidase metabolism.
- Lattes cover-glass test using a diagnostic kit of pathogens from commercial fish (Bionor MONO-AS—Code DD020).

A single colony from the purity test plate (culture characteristics) is mixed with a drop of antiserum on a microscope slide. The test uses a specific rabbit antiserum against *Aeromonas salmonicida*. A negative control culture is likewise mixed with a drop of antiserum. Positive agglutination must be observed with the test sample. The negative control sample must not show any agglutination.

Optical Density:

Optical density measurements at 580 nm are recorded at the end of each culture in 20 liter bottles and at intervals throughout final fermentation. Optical density measurements are taken from 20 liter culture bottles to ensure that each of these inoculants has grown satisfactorily. Optical density measurements are recorded at intervals throughout final fermentation to determine the optimum time for harvest, as indicated at the end of the exponential growth phase.

A sample of the culture is placed in a cuvette and the optical density is measured directly using a spectrophotometer. If necessary, the sample may be diluted in 0.85% sterile saline solution in order to obtain opacity within the spectrophotometer's range. The method is only used to confirm satisfactory growth of the inoculant and to determine the optimum time for harvest of the final fermentation. The final optical density reading is not critical and no set criterion applies. However, the final value obtained from the culture in the fermentor is normally within the following range:

8-11 for MT004 strain (without iron)

13-18 for MT423 strain (iron supplemented)

The absolute criterion for optical density is not appropriate for several reasons. First, considering that the medium used is of biological origin, there is inevitably a variation in the degree to which a specific batch will support growth. Second, the frequency of sampling for optical density is restricted to 45 minute intervals due to the need to re-sterilize the sampling port. Consequently, the precise harvest time may allow the culture to be maintained in the stationary phase for a short period of time, during which a reduction in optical density may be observed.

Viable Count

A sample of the culture is taken for the viable count at the end of fermentation and prior to adding the inactivator. The viable count serves as a definitive measurement of yield and forms the basis for subsequent mixing of the vaccine. The viable count is carried out using the Miles and Misra method [see e.g., Hedges, *Int J Food Microbiol.* 25:76(3):207-14 (2002)] with Tryptone Soya Broth as diluent and Tryptone Soya Agar as growth medium. Suitable ten-fold serial dilutions of the sample are prepared and ten replicate 0.025 ml drops of each dilution placed on the agar plate. The plates are incubated at 22° C. for 24-48 hours. Only those dilutions where colonies may be clearly counted are used to calculate the viable count.

The viable count is used as the basis for mixing the vaccine. The actual count is not critical and no set criterion is applied. However, normal counts are within the range 0.3-1.5×10/ml for both strains MT004 and MT423. The absolute criterion is not appropriate for several reasons. First, considering that the medium used is of biological origin, there is inevitably a variation in the degree to which a specific batch will support growth.

Second, the frequency of sampling for optical density is restricted to 45 minute intervals due to the need to re-sterilize the sampling port. Consequently, the precise harvest time may allow the culture to be maintained in the stationary phase for a short period of time, during which a reduction in optical density may be observed.

Protease Test

The protease test is carried out on a sample of material taken immediately following the inactivation period, but before the addition of sodium thiosulphate. With the improved control of the culture's conditions, no release of protease has been observed. However, because it is possible to sample the culture from the final fermentor at intervals of no less than 45 minutes, there is the possibility that some cells will die, and consequently lysis may occur prior to inactivation. This test provides the reassurance that any protease that may be released is completely inactivated.

Protease Assay.

3 ml of inactivated culture is added to 20 mg of SKY BLUE powder suspended in 2.5 ml of PBS and incubated for 15 minutes at ambient temperature. A positive control in which 20 mg of trypsin replaces the test samples is also incubated. The SKY BLUE powder is insoluble in PBS, but if protease activity is present, the material degrades and blue dye is released into the solution. The positive control must show a blue color while negative controls must remain colorless. To be acceptable, the test samples must not exhibit any protease activity. Positive samples must show a blue coloration.

Inactivation Test

A specific test for inactivation of the culture is carried out following neutralization of the residual inactivator. A subsequent test for continuous and complete inactivation is carried out on the mixed aqueous phase of the vaccine. The test confirms the complete, satisfactory inactivation of all viable organisms.

Inactivation Assay:

1 ml of inactivated culture is inoculated in each of six tubes containing 9 ml of TSB. Two of these inoculated tubes are inoculated with 0.1 ml of positive control culture with *Aeromonas salmonicida* of the same strains as the sample being tested, inoculating with a designated concentration of between 1 and 10 organisms. Two further inoculated tubes are additionally inoculated with 0.1 ml using the same positive control culture diluted 1 in 10. Also 0.1 ml of both positive control preparations are inoculated in two tubes, each containing 9.9 ml of TSB and another two tubes of TSB medium are kept only as negative controls. Therefore, duplicates of the following tubes are prepared (a total of 12 tubes in all):

Inoculated with 1 ml of test sample

Inoculated with 1 ml of test sample+0.1 ml positive control

Inoculated with 1 ml of test sample+0.1 ml positive control (diluted 1/10)

Inoculated with 0.1 ml positive control

Inoculated with 0.1 ml positive control diluted 1/10

Not inoculated

All of the above tubes are incubated for 48 hours at 22° C. At the end of this time, any tube in which growth cannot be seen is subcultivated. Subcultivation is carried out by spreading 1 ml of the medium onto each of two plates of tryptone soya agar. The medium is left to absorb into the agar for 1 hour at ambient temperature and the plates are incubated (inverted) for 48 hours at 22° C. The original tubes are also incubated for 48 hours at 22° C.

At the end of this time, growth (or absence of growth) is recorded in all cultures. The criterion of being acceptable is that all the tubes inoculated with the test sample only and all plates inoculated from these must not show any growth. In addition, all tubes inoculated with the highest concentration of organisms of the positive control and/or all plates inoculated from these must show growth of the control organism. If the tubes inoculated exclusively with the lowest dilution of the positive control culture and/or the plates inoculated from these show growth, similar results must be observed for the tubes and plates inoculated with the test sample plus the diluted positive control. The control mediums must remain negative.

Test for IROMPS

This test only applies to the material of strain MT004 and applies to a sample of final bulk antigen following inactivation and neutralization but, prior to distributing the material between the storage containers. The test is a qualitative method for confirming the presence of typical iron-restricted proteins in the preparation.

SDS-PAGE electrophoresis is performed on the sample. The SDS-PAGE gels are electroblotted to PVDF membranes that are then incubated with a rat monoclonal antibody against IROMP. Coupling of the monoclonal antibody is detected by a conjugate of goat anti-rat alkaline phosphatase and displayed using a NBT-BCIP substrate. A positive control preparation of *Aeromonas salmonicida* IROMP is spread on the same gel together with the molecular weight markers. The method is qualitative, but the acceptance criterion requires that the samples exhibit bands consistent with those of the control preparation. More particularly, protein bands must be detected at about 70, 72, 77 and 82 kilodaltons.

Sterility

The sterility of each container of final bulk antigen is confirmed using a specific sterility test although the inactivation test also provides additional evidence of sterility of the bulk product prior to distribution. The test provides the assurance that each container of bulk antigen is sterile.

The method used is that indicated in the Ph. Eur. Using direct inoculation thioglycollate and soya broths are incubated at 32° C. and 22° C. respectively, and both are subcultivated after 14 days of incubation. The subcultures are incubated for 7 days, while the original cultures are incubated for a total of 21 days. The method includes positive control cultures specified in the Ph. Eur.

To be acceptable the samples being tested must be sterile. The positive control cultures must show profuse early growth (within 3 days).

TABLE 14

SEQUENCES

| SEQ ID NO.: | DESCRIPTION |
|---|---|
| 1 | Nucleotide sequence encoding the genomic 1057 ORF 1 gene. |
| 2 | Amino acid sequence expressed by the ORF 1 gene [$^{Ps}p_1 90$]. |
| 3 | Nucleotide sequence encoding the genomic 1057 ORF 2 gene. |
| 4 | Amino acid sequence expressed by the ORF 2 gene [$^{Ps}p_2 90$]. |
| 5 | Nucleotide sequence encoding the PEGT1 ORF 1 gene. |
| 6 | Nucleotide sequence encoding the PEGT1 ORF 2 gene. |
| 7 | Amino acid sequence of the 45 kDa protein. |
| 8 | Amino acid sequence of the 45 kDa protein minus the signal peptide. |
| 9 | Amino acid sequence of an AMP binding enzyme homolog. |
| 10 | Amino acid sequence of ORF A. |
| 11 | Amino acid sequence of ORF B. |
| 12 | Amino acid sequence of a DDE endonuclease homolog. |
| 13 | Amino acid sequence of a transposase homolog. |
| 14 | Amino acid sequence of an HlyD homolog. |
| 15 | Amino acid sequence of an AcrB/AcrD/AcrF homolog. |
| 16 | 2,092 nucleotide nucleotide sequence comprising the coding sequence of the 45 kDa protein. |

What is claimed is:

1. A polypeptide that has an amino acid sequence comprising the amino acid sequence of SEQ ID NO: 2;

wherein said polypeptide is in a form selected from the group consisting of isolated, recombinant, or both isolated and recombinant.

2. A chimeric polypeptide that comprises a polypeptide; wherein said polypeptide comprises the amino acid sequence of SEQ ID NO: 2.

3. A vaccine that comprises a polypeptide; wherein said polypeptide comprises the amino acid sequence of SEQ ID NO: 2.

4. The vaccine of claim 3 that further comprises a $^{Ps}$45 protein or antigenic fragment thereof.

5. The vaccine of claim 3 that further comprises an antigen obtained from an Infectious Pancreatic Necrosis (IPN) virus.

6. The vaccine of claim 5 wherein the antigen is selected from the group consisting of the VP2 var protein and the VP3 protein.

7. The vaccine of claim 3 further comprising both the VP2 var protein and the VP3 protein from Infectious Pancreatic Necrosis (IPN) virus.

8. The vaccine of claim 3 that further comprises an antigen obtained from *Aeromonas salmonicida*.

* * * * *